United States Patent
Thomas et al.

(10) Patent No.: US 6,514,971 B1
(45) Date of Patent: Feb. 4, 2003

(54) CINNOLINE DERIVATIVES AND USE AS MEDICINE

(75) Inventors: Andrew Peter Thomas, Macclesfield (GB); Laurent Francois Andre Hennequin, Chemin de Vrilly (FR)

(73) Assignees: Zeneca Limited, London (GB); Zeneca Pharma S.A., Cergy Cedex (FR)

(*) Notice: Subject to any disclaimer, the term of this patent is extended or adjusted under 35 U.S.C. 154(b) by 0 days.

(21) Appl. No.: 09/142,839

(22) PCT Filed: Mar. 11, 1997

(86) PCT No.: PCT/GB97/00650

§ 371 (c)(1), (2), (4) Date: Apr. 13, 1999

(87) PCT Pub. No.: WO97/34876

PCT Pub. Date: Sep. 25, 1997

(30) Foreign Application Priority Data

Mar. 15, 1996 (EP) ............................. 96400533

(51) Int. Cl.[7] .................. A61K 31/502; C07D 237/28; C07D 403/12; C07D 413/12; C07D 417/12

(52) U.S. Cl. .............................. 514/234.5; 514/228.2; 514/248; 544/62; 544/116; 544/119; 544/235

(58) Field of Search ................. 544/235, 116, 544/119, 62; 514/248, 234.5, 228.2

(56) References Cited

U.S. PATENT DOCUMENTS

| | | | |
|---|---|---|---|
| 4,957,925 A | 9/1990 | Gubin et al. | 514/299 |
| 4,994,474 A | 2/1991 | Gubin et al. | 514/339 |
| 5,017,579 A | 5/1991 | Gubin et al. | 514/299 |
| 5,145,843 A * | 9/1992 | Arnold et al. | 514/63 |
| 5,147,878 A | 9/1992 | Gubin et al. | 514/299 |
| 5,182,291 A | 1/1993 | Gubin et al. | 514/300 |
| 5,215,988 A | 6/1993 | Gubin et al. | 514/233.2 |

FOREIGN PATENT DOCUMENTS

| | | |
|---|---|---|
| EP | 0326330 | 8/1989 |
| EP | 0302793 | 9/1989 |

OTHER PUBLICATIONS

Barber et al., A New Cinnoline Synthesis. Part VI.[1] 4–Mercaptocinnolines, J. Chem. Soc., vol. 9, 1968, pp. 1156–1158.

Castle et al., Cinnoline Chemistry. I. Some Condensation Reactions of 4–Chlorocinnoine, J. Org. Chem., vol. 17, 1952, pp. 1571–1575.

Castle et al., Cinnoline Chemistry. II. The Condensation of 4–Methylcinnoline with Aldehydes, J. Org. Chem., vol. 18, 1953, pp. 1706–1708.

Castle et al., Cinnoline Chemistry. III. Substituted 4–Cinnolyl–Acetonitriles, J. Org. Chem., vol. 19, 1954, pp. 1117–1123.

Castle et al., Cinnoline Chemistry IV, Infrared Spectra, Journal of the American Pharmceutical Association, vol. 48, 1959, pp. 135–139 (including Abstract, 3–Electronic Phenomena, 1959, cols. 8809–8810.

Castle et al., Cinnoline Chemistry. V. 4–Mercaptocinnolines and Related Compounds, J. Org. Chem., vol. 25, 1960, pp. 570–572.

(List continued on next page.)

Primary Examiner—Emily Bernhardt
(74) Attorney, Agent, or Firm—Morgan, Lewis & Bockius LLP

(57) ABSTRACT

The invention relates to the use of cinnoline derivatives of formula (I)

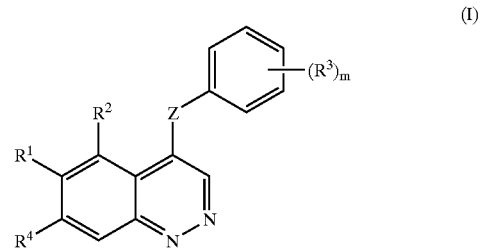

wherein Z represents —O—, —NH—, —S— or —CH$_2$—; m is an integer from 1 to 5; $R^1$ represents hydrogen, hydroxy, halogeno, nitro, cyano, trifluoromethyl, C$p_{1-3}$alkyl, C$_{1-3}$alkoxy, C$_{1-3}$alkylthio or NR$^6$R$^7$ (wherein R$^6$ and R$^7$, which may be the same or different, each represents hydrogen or C$_{1-3}$alkyl); $R^2$ represents hydrogen, hydroxy, auoro, chioro, methoxy, amino or nitro; $R^3$ represents hydroxy, halogeno, C$_{1-3}$alkyl, C$_{1-3}$alkoxy, C$_{1-3}$alkanoyloxy, trifluoromethyl, cyano, amino or nitro; $R^4$ represents hydrogen, hydroxy, halogeno, cyano, nitro, amino, trifluoromethyl, C$_{1-3}$alkyl or a group $R^5$—X$^1$ (wherein X$^1$ represents —O—, —CH$_2$—, —S—, —SO—, —SO$_2$—, —NR$^8$CO—, —CONR$^9$—, —SO$_2$NR$^{10}$—, —NR$^{11}$SO$_2$— or NR$_{12}$— (wherein R$^8$, R$^9$, R$^{10}$, R$^{11}$ and R$^{12}$ each independently represents hydrogen, C$_{1-3}$alkyl or C$_{1-3}$alkoxy C$_{2-3}$alkyl) and $R^5$ is an optionally substituted alkyl, carbocylic or heterocylic group which may be saturated or unsaturated and may be directly linked to the cinnoline ring or be linked via a carbon chain which may have heteroatom linking groups within it and salts thereof, in the manufacture of a medicament for use in the production of an anti angiogenic and/or vascular permeability reducing effect in a warmn-blooded animal such as a human being, processes for the preparation of such derivatives, pharmnaceutical compositions containing a compound of formula (I) or a pharmnaceutically acceptable salt thereof as active ingredient and compounds of formula (I). The compounds of formula (I) and the pharmaceutically acceptable salts thereof inhibit the effects of VEGF, a property of value in the treatment of a number of disease states including cancer and rheumatoid arthritis.

13 Claims, No Drawings

OTHER PUBLICATIONS

Castle et al., Cinnoline Chemistry. IX. 5–, 6–, 7–and 8–Halogen Substituted 4–Mercaptocinnolines and Related Compounds (1). J. Het. Chem., vol. 1, 1964, pp. 98–106.

Castle et al., Cinnoline Chemistry. XII. The Synthesis of 6–Fluoro–4–methylcinnoline and other Cinnolines as Potential Antitumor Agents (1), J. Het. Chem., vol. 2, 1965, pp. 459–462.

Hayashi et al., Cinnoline . . . 4–(Methylsulfonyl)–cinnoline . . . Cinnolines. II. [1)] On the Reaction of 4–(Methylsulfonyl)–cinnoline with Nucleophiles, Yakagaku Zasshi, vol. 88(1), 1968, pp. 94–97.

Kaushal et al., Studies in Cinnolinobenzothiazine Derivatives: . . . 7H–Cinnolino[4,3–b]–I,4–benzothiazines & Their Derivatives, Indian J. Chem. vol. 6, Jul. 1968, pp. 350–352.

Lunt et al., A New Cinnoline Synthesis. Part V. 4–Substituted Amino–cinnolines as Potential Antiprotozoal Agents. J. Chem. Soc., vol. 9, 1968, pp. 1152–1555.

Rewcastle et al., Tyrosine Kinase Inhibitors. 5. Synthesis and Structure– . . . Domain of the Epidermal Growth Factor Receptor, J. Med. Chem. vol. 38, 1995, pp. 3482–3487.

Yarnal et al., Studies in Cinnoline Chemistry. I. The Synthesis of Substituted Phenyl Cinnolyl Sulfides, J. Med. Chem., vol. 11, 1968, p. 1270.

Yarnal et al., Studies in Cinnoline Chemistry: Part III–Synthesis of Substituted Phenyl Cinnolyl Sulphides, Sulphone–N–oxides & Sulphones, Indian Journal of Chemistry, vol. 11, Mar. 1973, pp. 211–213.

Yarnal et al., Studies in Cinnoline Chemistry–IV The Synthesis of Substituted Phenyl Cinnolyl Ethers, Journal of the Karnatak University–Science, Dharwar–3, India, vol. 18, 1973, pp. 25–30.

Yarnal et al., Studies in Cinnoline Chemistry–V The Synthesis of Substituted Arylamino Cinnolines. Karnatak University, Dharwad, Sci., vol. 29, 1984, pp. 82–86.

Yarnal et al., Synthese von substituierten Phenylcinnolyl-–Sulfiden und Sulfonen, Arch. Pharm. (Weinheim), vol. 303(7), 1970, pp. 560–562.

* cited by examiner

CINNOLINE DERIVATIVES AND USE AS MEDICINE

This application is the national phase of international application PCT/GB97/00650 filed Mar. 11, 1997 which designated the U.S.

The present invention relates to the use of cinnoline derivatives in the manufacture of medicaments for use in the production of antiangiogenic and/or vascular permeability reducing effects in warm-blooded animals such as humans, to a method for the treatment of disease states associated with angiogenesis and/or increased vascular permeability, to certain such cinnoline derivatives for use in medicine and to certain cinnoline derivatives per se, processes for their preparation and pharmaceutical compositions containing them as active ingredient.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57–66; Folkman, 1995, Nature Medicine 1: 27–31). Alteration of vascular permeability is thought to play a role in both normal and pathological physiological processes (Cullinan-Bove et al, 1993, Endocrinology 133: 829–837; Senger et al, 1993, Cancer and Metastasis Reviews, 12: 303–324). Several polypeptides with in vitro endothelial cell growth promoting activity have been identified including, acidic and basic fibroblast growth factors (aFGF & bFGF) and vascular endothelial growth factor (VEGF). By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848–859; Kolch et al, 1995, Breast Cancer Research and Treatment, 36:139–155) and vascular permeability (Connolly et al, 1989, J. Biol. Chem. 264: 20017–20024). Antagonism of VEGF action by sequestration of VEGF with antibody can result in inhibition of tumour growth (Kim et al, 1993. Nature 362: 841–844).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt or Flt1, the kinase insert domain-containing receptor, KDR (also referred to as Flk-1), and another fms-like tyrosine kinase receptor, Flt4. Two of these related RTKs, Flt and KDR, have been shown to bind VEGF with high affinity (De Vries et al. 1992, Science 255: 989–991; Terman et al. 1992, Biochem. Biophys. Res. Comm. 1992, 187: 1579–1586). Binding of VEGF to these receptors expressed in heterologous cells has been associated with chances in the tyrosine phosphorylation status of cellular proteins and calcium fluxes.

European Patent Publication No. 0326330 discloses certain quinoline, quinazoline and cinnoline plant fungicides. Certain of these plant fungicides are also stated to possess insecticidal and miticidal activity. There is however no disclosure or any suggestion that any of the compounds disclosed may be used for any purpose in animals such as humans. In particular, the European Patent Publication contains no teaching whatsoever concerning angiogenesis and/or increased vascular permeability mediated by growth factors such as VEGF.

A number of further documents described hereinafter disclose certain cinnoline derivatives, but none of these documents contain any teaching whatsoever concerning angiogenesis and/or increased vascular permeabilty mediated by growth factors such as VEGF. Thus J. Med Chem. (1995), 38(18), 3482–7 discloses 4-(3-bromoanilino) cinnoline. J. Chem. Soc. C (1968), (9), 1152–5 discloses 6-chloro-4-phenoxycinnoline. J. Karnatak Univ., Sci. (1984), 29, 82–6 discloses certain 4-anilinocinnolines and Indian J. Chem (1973), 11(3), 211–13 discloses certain 4-phenylthiocinnolines. All of these disclosed compounds were tested for physiological activity, but all except the two specifically named compounds below were found to be inactive in the tests employed, J. Karnatak Univ., (1973), 18, 25–30 discloses certain 4-phenoxycinnolines some of which showed a little antimicrobial activity but none of which showed analgesic or antihistaminic activity, J. Karnatak Univ., Sci. (1984),29, 82–6 discloses two compounds: 4-(4-methoxyanilino)-6,7-dimethoxycinnoline and 4-(3-chloroanilino)-6,7-dimethoxycinnoline which were tested and were found to have some anti-inflammatory and anti-arthritic activity. The papers and patents listed below describe the synthesis of certain cinnolines with a phenyl ring linked via a group selected from —O—, —S—, —NH— and —CH$_2$— at the 4-position: U.S. Pat. No. 5,017,579, U.S. Pat. No. 4,957,925, U.S. Pat. No. 4,994,474, EP 0302793 A2, Arch Pharm (Weinheim) (1970), 303(7), 560–2, J. Med. Chem. (1968), 11, 1270, Indian J. Chem. (1968), 6(7), 350–2, J. Chem. Soc. C (1968), (9), 1156–8, Yakugaku Zasshi (1968), 88(1), 94–7, J. Org. Chem. (1960), 25, 570, J. Org. Chem. (1952), 17, 1571–5, J. Org. Chem. (1953), 18, 1706–8, J. Org. Chem. (1954), 19. 1117–23 and J. Am. Pharm. Assoc. (1959), 48, 135–9, but none of these papers and patents disclose any utility at all for the cinnolines they describe.

The present invention is based on the discovery of compounds that surprisingly inhibit the effects of VEGF, a property of value in the treatment of disease states associated with angiogenesis and/or increased vascular permeability such as cancer, diabetes, psoriasis, rheumatoid arthritis, Kaposi's sarcoma, haemangioma, acute and chronic nephropathies, atheroma, arterial restenosis, autoimmune diseases, acute inflammation and ocular diseases with retinal vessel proliferation. Compounds of the present invention possess good activity against VEGF receptor tyrosine kinase whilst possessing some activity against epidermal growth factor (EGF) receptor tyrosine kinase. Furthermore, compounds of the present invention, possess substantially higher potency against VEGF receptor tyrosine kinase than against EGF receptor tyrosine kinase or FGF Ri receptor tyrosine kinase. Thus compounds of the invention which have been tested possess activity against VEGF receptor tyrosine kinase such that they may be used in an amount sufficient to inhibit VEGF receptor tyrosine kinase whilst demonstrating no significant activity against EGF receptor tyrosine kinase or FGF R1 receptor tyrosine kinase.

According to one aspect of the present invention there is provided the use of a compound of the formula I:

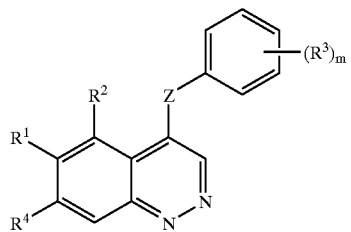

(I)

[wherein:

Z represents —O—, —NH—, —S— or —CH$_2$—;

m is an integer from 1 to 5;

R$^1$ represents hydrogen, hydroxy, halogeno, nitro, cyano, trifluoromethyl, C$_{1-3}$alkyl, C$_{1-3}$alkoxy, C$_{1-3}$alkylthio or NR$^6$R$^7$ (wherein R$^6$ and R$^7$, which may be the same or different, each represents hydrogen or C$_{1-3}$alkyl);

R$^2$ represents hydrogen, hydroxy, fluoro, chloro, methoxy, amino or nitro;

R$^3$ represents hydroxy, halogeno, C$_{1-3}$alkyl, C$_{1-3}$alkoxy, C$_{1-3}$alkanoyloxy, trifluoromethyl, cyano, amino or nitro;

R$^4$ represents hydrogen, hydroxy, halogeno, cyano, nitro, amino, trifluoromethyl, C$_{1-3}$alklyl or a group R$^5$—X$^1$ (wherein X$^1$ represents —O—, —CH$_2$—, —S—, —SO—, —SO$_2$—, —NR$^8$CO—, —CONR$^9$—, —SO$_2$NR$^{10}$—, —NR$^{11}$SO$_2$— or —NR$^{12}$— (wherein R$^8$, R$^9$, R$^{10}$, R$^{11}$ and R$^{12}$ each independently represents hydrogen, C$_{1-3}$alkyl or C$_{1-3}$alkoxyC$_{2-3}$alkyl) and R$^5$ is selected from one of the following fourteen groups:

1) C$_{1-5}$alkyl, C$_{1-5}$hydroxyalkyl, C$_{1-5}$fluoroalkyl, C$_{1-5}$aminoalkyl;

2) C$_{1-5}$alkylX$^2$COR$^{13}$ (wherein X$^2$ represents —O— or NR$^{14}$ (in which R$^{14}$ represents hydrogen, C$_{1-3}$alkyl or C$_{1-3}$ alkoxyC$_{2-3}$alkyl) and R$^{13}$ represents C$_{1-3}$alkyl, NR$^{15}$R$^{16}$ or OR$^{17}$ (wherein R$^{15}$, R$^{16}$ and R$^{17}$ which may be the same or different are each hydrogen, C$_{1-3}$alkyl or C$_{1-3}$alkoxyC$_{2-3}$alkyl), with the proviso that when X$^2$ is —O—, R$^{13}$ is not OR$^{17}$);

3) C$_{1-5}$alkylX$^3$R$^{18}$ (wherein X$^3$ represents —O—, —S—, —SO—, —SO$_2$—, —OCO—, —NR$^{19}$CO—, —CONR$^{20}$—, —SO$_2$NR$^{21}$—, —NR$^{22}$SO$_2$— or —NR$^{23}$— (wherein R$^{19}$, R$^{20}$, R$^{21}$, R$^{22}$ and R$^{23}$ each independently represents hydrogen, C$_{1-3}$alkyl or C$_{1-3}$alkoxyC$_{2-3}$alkyl) and R$^{18}$ represents hydrogen, C$_{1-3}$alkyl, cyclopentyl, cyclohexyl or a 5 or 6 membered saturated heterocyclic group with one or two heteroatoms, selected independently from O, S and N, which C$_{1-3}$alkyl group may bear one or two substituents selected from oxo, hydroxy, halogeno and C$_{1-4}$alkoxy and which cyclic group may bear one or two substituents selected from oxo, hydroxy, halogeno, C$_{1-4}$alkyl, C$_{1-4}$hydroxyalkyl and C$_{1-4}$alkoxy);

4) C$_{1-5}$alkylX$^4$C$_{1-5}$alkylX$^5$R$^{24}$ (wherein X$^4$ and X$^5$ which may be the same or different are each —O—, —S—, —SO—, —SO$_2$—, —NR$^{25}$CO—, —CONR$^{26}$—, —SONR$^{27}$—, —NR$^{28}$SO$_2$— or —NR$^{29}$— (wherein R$^{25}$, R$^{26}$, R$^{27}$, R$^{28}$ and R$^{29}$ each independently represents hydrogen, C$_{1-3}$alkyl or C$_{1-3}$alkoxyC$_{2-3}$alkyl) and R$^{24}$ represents hydrogen or C$_{1-3}$alkyl);

5) C$_{1-5}$alkylR$^{30}$ (wherein R$^{30}$ is a 5 or 6 membered saturated heterocyclic group with one or two heteroatoms, selected independently from O, S and N, which heterocyclic group may bear one or two substituents selected from oxo, hydroxy, halogeno, C$_{1-4}$alkyl, C$_{1-4}$hydroxyalkyl and C$_{1-4}$alkoxy);

6) C$_{2-5}$alkenylR$^{30}$ (wherein R$^{30}$ is as defined hereinbefore);

7) C$_{2-5}$alkynylR$^{30}$ (wherein R$^{30}$ is as defined hereinbefore);

8) (CH$_2$)$_n$R$^{31}$ (wherein n is an integer from 0 to 5 and R$^{31}$ is a phenyl group, a pyridone group or a 5 or 6 membered aromatic heterocyclic group with 1 to 3 heteroatoms selected from O, N and S, which phenyl, pyridone or aromatic heterocyclic group may carry up to 5 substituents selected from hydroxy, halogeno, C$_{1-4}$alkyl, C$_{1-4}$alkoxy, C$_{1-4}$hydroxyalkyl, C$_{1-4}$hydroxyalkoxy, carboxy, cyano, CONR$^{32}$R$^{33}$ and NR$^{34}$COR$^{35}$ (wherein R$^{32}$, R$^{33}$, R$^{34}$ and R$^{35}$, which may be the same or different, each represents hydrogen, C$_{1-4}$alkyl or C$_{1-3}$alkoxyC$_{2-3}$alkyl);

9) C$_{2-5}$calkenylR$^{31}$ (wherein R$^{31}$ is as defined hereinbefore);

10) C$_{2-5}$alkynylR$^{31}$ (wherein R$^{31}$ is as defined hereinbefore);

11) C$_{1-5}$alkylX$^6$R$^{31}$ (wherein X$^6$ represents —O—, —S—, —SO—, —SO$_2$—, —NR$^{36}$CO—, —CONR$^{37}$—, —SO$_2$NR$^{38}$—, —NR$^{39}$SO$_2$— or —NR$^{40}$— (wherein R$^{36}$, R$^{37}$, R$^{38}$, R$^{39}$ and R$^{40}$ each represents hydrogen, C$_{1-3}$alkyl or C$_{1-3}$alkoxyC$_{2-3}$alkyl) and R$^{31}$ is as defined hereinbefore);

12) C$_{2-5}$alkenyX$^7$R$^{31}$ (wherein X$^7$ represents —O—, —S—, —SO—, —SO$_2$—, —NR$^{41}$CO—, —CONR$^{42}$—, —SO$_2$NR$^{43}$—, —NR$^{44}$SO$_2$— or —NR$^{45}$— (wherein R$^{41}$, R$^{42}$, R$^{43}$, R$^{44}$ and R$^{45}$ each independently represents hydrogen, C$_{1-3}$alkyl or C$_{1-3}$alkoxyC$_{2-3}$alkyl) and R$^{31}$ is as defined hereinbefore);

13) C$_{2-5}$alkynylX$^8$R$^{31}$ (wherein X$^8$ represents —O—, —S—, —SO—, —SO$_2$—, —NR$^{46}$CO—, —CONR$^{47}$—, —SO$_2$NR$^{48}$—, —NR$^{49}$SO$_2$— or —NR$^{50}$— (wherein R$^{46}$, R$^{47}$, R$^{48}$, R$^{49}$ and R$^{50}$ each independently represents hydrogen, C$_{1-3}$alkyl or C$_{1-3}$alkoxyC$_{2-3}$alkyl) and R$^{31}$ is as defined hereinbefore);

14) C$_{1-3}$alkylX$^9$C$_{1-3}$alkylR$^{31}$ (wherein X$^9$ represents —O—, —S—, —SO—, —SO$_2$—, —NR$^{51}$CO—, —CONR$^{52}$—, —SO$_2$NR$^{53}$—, —NR$^{54}$SO$_2$— or —NR$^{55}$— (wherein R$^{51}$, R$^{52}$, R$^{53}$, R$^{54}$ and R$^{55}$ each independently represents hydrogen, C$_{1-3}$alkyl or C$_{1-3}$alkoxyC$_{2-3}$alkyl) and R$^{31}$ is as defined hereinbefore))]; and salts thereof, in the manufacture of a medicament for use in the production of an antiangiogenic and/or vascular permeability reducing effect in a warm-blooded animal such as a human being.

According to a further aspect of the present invention there is provided a method for producing an antiangiogenic and/or vascular permeability reducing effect in a warm-blooded animal in need of such treatment which comprises administering to said animal an effective amount of a compound of formula I, as defined hereinbefore, or a pharmaceutically acceptable salt thereof.

Z is advantageously —S—, preferably —O—, but especially —NH—.

m is advantageously an integer from 2 to 5, preferably 2 or 3, especially 3.

R$^1$ is advantageously hydrogen, hydroxy, C$_{1-3}$alkyl, C$_{1-3}$alkoxy, amino, cyano, nitro or trifluoromethyl.

$R^2$ is preferably hydrogen, hydroxy, methyl, ethyl, methoxy or ethoxy, more preferably hydrogen, hydroxy, methyl or methoxy but especially methoxy.

$R^2$ is advantageously hydrogen, hydroxy, fluoro, methoxy, amino or nitro.

$R^2$ is preferably hydrogen, amino or nitro, but especially hydrogen.

In one embodiment of the present invention $R^3$ represents hydroxy, halogeno, $C_{1-3}$alkyl, $C_{1-3}$alkoxy, trifluoromethyl, cyano, amino or nitro.

Advantageously in another embodiment of the present invention one $R^3$ substituent is meta-hydroxy and the other one or more are each selected from halogeno, methyl and methoxy.

In another embodiment of the invention the phenyl group bearing $(R^3)_m$ is preferably of the formula II:

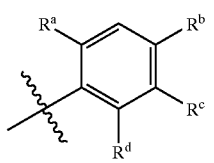

(II)

wherein:
$R^a$ represents hydrogen, methyl, fluoro or chloro, preferably hydrogen, fluoro or chloro, especially fluoro;
$R^b$ represents hydrogen, methyl, methoxy, bromo, fluoro or chloro;
$R^c$ represents hydrogen or hydroxy, especially hydroxy;
$R^d$ represents hydrogen, fluoro or chloro, more preferably hydrogen or fluoro, especially fluoro, Preferably in another embodiment of the invention two $R^3$ substituents are halogeno. especially ortho, ortho'-difluoro, and the other one or more are each selected from halogeno, hydroxy and methyl, more preferably from halogeno and methyl.

More preferably in another embodiment of the invention the phenyl group bearing $(R^3)_m$ carries at least two substituents of which one is fluoro, especiallyortho-fluoro.

In a particular aspect of the present invention, the phenyl group bearing $(R^3)_m$ is the 2-fluoro-5-hydroxy-4-methylphenyl group, the 4-chloro-2-fluoro-5-hydroxyphenyl group, the 4-bromo-2,6-difluorophenyl group, the 4-chloro-2,6-difluorophenyl group, the 4-chloro-2-fluorophenyl group, the 4-chloro-3-hydroxyphenyl group, the 4-bromo-3-hydroxyphenyl group, the 3-hydroxy-4-methyl group or the 4-bromo-2-fluoro-5-hydroxyphenyl group.

In a particularly preferred aspect of the invention the phenyl group bearing $(R^3)_m$ is the 2-fluoro-5-hydroxy-4-methylphenyl group, the 4-chloro-2-fluoro-5-hydroxyphenyl group, the 4-chloro-3-hydroxyphenyl group, the 4-bromo-3-hydroxyphenyl group, the 3-hydroxy-4-methyl group or the 4-bromo-2-fluoro-5-hydroxyphenyl group.

Conveniently $X^1$ represents —O—, —S—, —CH$_2$—, —NR$^8$CO—, —CONR$^9$—, —NR$^{11}$SO$_2$— or —NR$^{12}$— (wherein $R^8$, $R^9$, $R^{11}$ and $R^{12}$ each independently represents hydrogen, $C_{1-3}$alkyl or $C_{1-2}$alkoxyethyl).

Advantageously $X^1$ represents —O—, —S—, —NR$^8$CO—, —NR$^{11}$SO$_2$— or —NR$^{12}$— (wherein $R^8$, $R^{11}$ and $R^{12}$ each independently represents hydrogen, $C_{1-3}$alkyl or $C_{1-2}$alkoxyethyl).

Preferably $X^1$ represents —O—, —S—, —NR$^8$CO— (wherein $R^8$ represents hydrogen or methyl) or NH.

More preferably $X^1$ represents —O— or —NHCO—, especially —O—.

Advantageously $X^2$ represents —O— or —NR$^{14}$— (wherein $R^{14}$ represents hydrogen, $C_{1-3}$alkyl or $C_{1-2}$alkoxyethyl).

Advantageously $X^3$ represents —O—, —S—, —SO—, —SO$_2$—, —NR$^{19}$CO—, —NR$^{22}$SO$_2$— or —NR$^{23}$— (wherein $R^{19}$, $R^{22}$ and $R^{23}$ each independently represents hydrogen, $C_{1-3}$alkyl or $C_{1-2}$alkoxyethyl).

Preferably $X^3$ represents —O—, —S—, —SO—, —SO$_2$— or —NR$^{23}$— (wherein $R^{23}$ represents hydrogen, $C_{1-3}$alkyl or $C_{1-2}$alkoxyethyl).

More preferably $X^3$ represents —O—, —S—, —SO—, —SO$_2$— or —NR$^{23}$— (wherein $R^{23}$ represents hydrogen, $C_{1-2}$alkyl or $C_{1-2}$alkoxyethyl), especially —O— or —NR$^{23}$— (wherein $R^{23}$ represents hydrogen or $C_{1-2}$alkyl).

Advantageously $X^4$ and $X^5$ which may be the same or different each represents —O—, —S—, —SO—, —SO$_2$— or —NR$^{29}$— (wherein $R^{29}$ represents hydrogen, $C_{1-3}$alkyl or $C_{1-2}$alkoxyethyl).

Preferably $X^4$ and $X^5$ which may be the same or different each represents —O—, —S— or —NR$^{29}$— (wherein $R^{29}$ represents hydrogen, $C_{1-3}$alkyl or $C_{1-2}$alkoxyethyl).

More preferably $X^4$ and $X^5$ which may be the same or different each represents —O—, —S— or —NR$^{29}$— (wherein $R^{29}$ represents hydrogen or $C_{1-3}$alkyl), especially —O— or —NH—, Advantageously $X^6$ represents —O—, —S— or —NR$^{40}$— (wherein $R^{40}$ represents hydrogen, $C_{1-2}$alkyl or $C_{1-2}$alkoxyethyl).

Preferably $X^7$ represents —O— or —NR$^{40}$— (wherein $R^{40}$ represents hydrogen or $C_{1-2}$alkyl).

Advantageously $X^7$ represents —O—, —S— or —NR$^{45}$— (wherein $R^{45}$ represents hydrogen, $C_{1-2}$alkyl or $C_{1-2}$alkoxyethyl).

Preferably $X^8$ represents —O— or —NR$^{45}$— (wherein $R^{40}$ represents hydrogen or $C_{1-2}$alkyl).

Advantageously $X^8$ represents —O—, —S— or —NR$^{50}$— (wherein $R^{50}$ represents hydrogen, $C_{1-2}$alkyl or $C_{1-2}$alkoxyethyl).

Preferably $X^8$ represents —O— or —NR$^{50}$— (wherein $R^{50}$ represents hydrogen or $C_{1-2}$alkyl).

Advantageously $X^9$ represents —O—, —S— or —NR$^{55}$— (wherein $R^{55}$ represents hydrogen, $C_{1-2}$alkyl or $C_{1-2}$alkoxyethyl).

Preferably $X^9$ represents —O— or —NR$^{55}$— (wherein $R^{55}$ represents hydrogen or $C_{1-2}$alkyl).

Conveniently $R^4$ is hydroxy, halogeno, nitro, trifluoromethyl, $C_{1-3}$alkyl, cyano, amino or a group $R^5$—$X^1$ (wherein $X^1$ is as defined hereinbefore and $R^5$ is selected from one of the following fourteen groups:

1) $C_{1-5}$alkyl, $C_{2-5}$hydroxyalkyl, $C_{1-5}$fluoroalkyl, $C_{2-5}$aminoalkyl;

2) $C_{2-3}$alkylX$^2$COR$^{13}$ (wherein $X^2$ is as defined hereinbefore and $R^{13}$ represents $C_{1-3}$alkyl. NR$^{15}$R$^{16}$ or OR$^{17}$ (wherein $R^{15}$, $R^{16}$ and $R^{17}$ which may be the same or different are each $C_{1-2}$alkyl or $C_{1-2}$alkoxyethyl) with the proviso that when $X^2$ is —O—, $R^{13}$ is not OR$^{17}$);

3) $C_{2-4}$alkylX$^3$R$^{18}$ (wherein $X^3$ is as defined hereinbefore and $R^{18}$ represents hydrogen, $C_{1-3}$alkyl, cyclopentyl, cyclohexyl or a 5 or 6 membered saturated heterocyclic group with one or two heteroatoms, selected independently from O, S and N, which $C_{1-3}$alkyl group may bear one or two substituents selected from oxo hydroxy, halogeno and $C_{1-3}$alkoxy and which cyclic group may bear one or two substituents selected from oxo, hydroxy, halogeno, $C_{1-3}$alkyl, $C_{1-3}$hydroxyalkyl and $C_{1-3}$alkoxy);

4) $C_{2-3}$alkyl$X^4C_{2-3}$alkyl$X^5R^{24}$ (wherein $X^4$ and $X^5$ are as defined hereinbtefore and $R^{24}$ represents hydrogen or $C_{1-3}$alkyl);

5) $C_{1-5}$alkyl$R^{56}$ (wherein $R^{56}$ is a 5 or 6 membered saturated heterocyclic group with one or two heteroatoms, selected independently from O, S and N, which heterocyclic group is linked to $C_{1-5}$alkyl through a carbon atom and which heterocyclic group may bear one or two substituents selected from oxo, hydroxy, halogeno, $C_{1-4}$alkyl, $C_{1-4}$hydroxyalkyl and $C_{1-4}$alkoxy) or $C_{2-5}$alkyl$R^{57}$ (wherein $R^{57}$ is a 5 or 6 membered saturated heterocyclic group with one or two heteroatoms of which one is N and the other is selected independently from O, S and N, which heterocyclic group is linked to $C_{2-5}$alkyl through a nitrogen atom and which heterocyclic group may bear one or two substituents selected from oxo, hydroxy, halogeno, $C_{1-4}$alkyl, $C_{1-4}$hydroxyalkyl and $C_{1-4}$alkoxy);

6) $C_{3-4}$alkenyl$R^{58}$ (wherein $R^{58}$ represents $R^{56}$ or $R^{57}$ as defined hereinbefore);

7) $C_{3-4}$alkynyl$R^{58}$ (wherein $R^{58}$ represents $R^{56}$ or $R^{57}$ as defined hereinbefore);

8) $(CH_2)_nR^{31}$ (wherein n is an integer from 0 to 4 and $R^{31}$ is a phenyl group, a pyridone group or a 5 or 6 membered aromatic heterocyclic group with 1 to 3 heteroatoms selected from O, N and S, which phenyl, pyridone or aromatic heterocyclic group may be substituted as hereinbefore defined, advantageously substituted with up to 2 substituents as hereinbefore defined, more preferably substituted with one substituent selected from the group of substituents as hereinbefore defined);

9) 1-$R^{31}$prop-1-en-3-yl or 1-$R^{31}$but-2-en-4-yl (wherein $R^{31}$ is as defined hereinbefore);

10) 1-$R^{31}$ prop-1-yn-3-yl or 1-$R^{31}$but-2-yn-4-yl (wherein $R^{31}$ is as defined hereinbefore);

11) $C_{1-5}$alkyl$X^6R^{31}$ (wherein $X^6$ and $R^{31}$ are as defined hereinbefore);

12) 1-($R^{31}X^7$)but-2-en4-yl (wherein $X^7$ and $R^{31}$ are as defined hereinbefore);

13) 1-($R^{31}X^8$)but-2-yn-4-yl (wherein $X^1$ and $R^{31}$ are as defined hereinbefore);

14) $C_{2-3}$alkyl$X^9C_{1-2}$alkyl$R^{31}$ (wherein $X^9$ and $R^{31}$ are as defined hereinbefore)).

Advantageously $R^4$ is hydroxy, halogeno, nitro, trifluoromethyl, $C_{1-3}$alkyl, cyano, amino or a group $R^5$—$X^1$ (wherein $X^1$ is as defined hereinbefore and $R^5$ is selected from one of the following fourteen groups:

1) $C_{1-4}$alkyl, $C_{2-4}$hydroxyalkyl, $C_{1-4}$fluoroalkyl, $C_{2-4}$aminoalkyl;

2) $C_{2-3}$alkyl$X^2COR^{13}$ (wherein $X^2$ is as defined hereinbefore and $R^{13}$ represents $C_{1-3}$alkyl, $NR^{15}R^{16}$ or $OR^{17}$ (wherein $R^{15}$, $R^{16}$ and $R^{17}$ which may be the same or different are each $C_{1-2}$alkyl or $C_{1-2}$alkoxyethyl) with the proviso that when $X^2$ is —O—, $R^{13}$ is not $OR^{17}$);

3) $C_{2-4}$alkyl$X^3R^{18}$ (wherein $X^3$ is as defined hereinbefore and $R^{18}$ represents $C_{1-3}$alkyl, cyclopentyl, cyclohexyl, pyrrolidinyl and piperidinyl which group is linked to $X^3$ through a carbon atom and which $C_{1-3}$alkyl group may bear one or two substituents selected from oxo, hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);

4) $C_{2-3}$alkyl$X^4C_{2-3}$alkyl$X^5R^{24}$ (wherein $X^4$ and $X^5$ are as defined hereinbefore and $R^{24}$ represents hydrogen or $C_{1-3}$alkyl);

5) $C_{1-4}$alkyl$R^{59}$ (wherein $R^{59}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-4}$alkyl through a carbon atom and which group may carry one or two substituents selected from oxo, hydroxy, halogeno, $C_{1-2}$alkyl, $C_{1-2}$hydroxyalkyl and $C_{1-2}$alkoxy) or $C_{2-4}$alkyl$R^{60}$ (wherein $R^{60}$ is a group selected from morpholino, thiomorpholino, pyrrolidin-1-yl, piperazin-1-yl and piperidino which group may carry one or two substituents selected from oxo, hydroxy, halogeno, $C_{1-2}$alkyl, $C_{1-2}$hydroxyalkyl and $C_{1-2}$alkoxy);

6) $C_{3-4}$alkenyl$R^{61}$ (wherein $R^{61}$ represents $R^{59}$ or $R^{60}$ as defined hereinbefore);

7) $C_{3-4}$alkynyl$R^{61}$ (wherein $R^{61}$ represents $R^{59}$ or $R^{60}$ as defined hereinbefore);

8) $(CH_2)_nR^{31}$ (wherein n is an integer from 1 to 3 and $R^{31}$ is a pyridone croup or a 5 or 6 membered aromatic heterocyclic group with 1 or 2 heteroatoms selected from O, N and S, of which preferably one is N which pyridone or aromatic heterocyclic group may be substituted as hereinbefore defined, preferably substituted with one substituent selected from halogeno, $C_{1-2}$alkyl, $C_{1-2}$alkoxy, $C_{1-2}$hydroxyalkyl, $C_{1-2}$hydroxyalkoxy, carboxy, cyano, $CONR^{32}R^{33}$ and $NR^{34}COR^{35}$ (wherein $R^{32}$, $R^{33}$, $R^{34}$ and $R^{35}$, which may be the same or different, each represents hydrogen, $C_{1-2}$alkyl or $C_{1-2}$alkoxyethyl));

9) 1-$R^{31}$but-2-en4-yl (wherein $R^{31}$ is as defined hereinbefore);

10) 1-$R^{31}$but-2-yn-4-yl (wherein $R^{31}$ is as defined hereinbefore); 11) $C_{1-5}$alkyl$X^6R^{31}$ (wherein $X^6$ and $R^{31}$ are as defined hereinbefore);

12) 1-($R^{31}$)but-2-en-4-yl (wherein $X^7$ and $R^{31}$ are as defined hereinbefore);

13) 1-($R^{31}X^8$)but-2-yn-4-yl (wherein $X^8$ and $R^{31}$ are as defined hereinbefore);

14) $C_{2-3}$alkyl$X^9C_{1-2}$alkyl$R^{31}$ (wherein $X^9$ and $R^{31}$ are as defined hereinbefore)).

Preferably $R^4$ is hydroxy, halogeno nitro, trifluoromethyl, $C_{1-3}$alkyl, cyano, amino or a group $R^5$—$X^1$ (wherein $X^1$ is as defined hereinbefore and $R^5$ is selected from one of the following eight groups:

1) $C_{1-3}$alkyl, $C_{2-3}$hydroxyalkyl, $C_{1-3}$fluoroalkyl, $C_{1-3}$aminoalkyl;

2) 2-(3,3-dimethylureido)ethyl, 3-(3,3-dimethylureido)propyl, 2-(3-methylureido)ethyl, 3-(3-methylureido)propyl, 2-ureidoethyl, 3-ureidopropyl, 2-(N,N-dimethylcarbamoyloxy)ethyl, 3-(N,N-dimethylcarbamoyloxy)propyl, 2-(N-methylcarbamoyloxy)ethyl, 3-(N-methylcarbamoyloxy)propyl, 2-(carbamoyloxy)ethyl, 3-(carbamoyloxy)propyl;

3) $C_{2-3}$alkyl$X^3R^{18}$ (wherein $X^3$ is as defined hereinbefore and $R^{18}$ represents $C_{1-2}$alkyl, cyclopentyl, cyclohexyl, pyrrolidinyl or piperidinyl which group is linked to $X^3$ through a carbon atom and which $C_{1-2}$alkyl group may bear one or two substituents selected from hydroxy, halogeno and $C_{1-2}$alkoxy and which cyclopentyl, cyclohexyl, pyrrolidinyl or piperidinyl group may carry one substituent selected from oxo, hydroxy, halogeno, $C_{1-2}$alkyl, $C_{1-2}$hydroxyalkyl and $C_{1-2}$alkoxy);

4) $C_{2-3}$alkyl$X^4C_{2-3}$alkyl$X^5R^{24}$ (wherein $X^4$ and $X^5$ are as defined hereinbefore and $R^{24}$ represents hydrogen or $C_{1-2}$alkyl);

5) $C_{1-2}$alkyv$R^{62}$ (wherein $R^{62}$ is a group selected from pyrrolidinyl, piperazinyl, piperidinyl, 1,3-dioxolan-2-yl, 1,3-dioxan-2-yl, 1,3-dithiolan-2-yl and 1,3-dithian-2-yl, which group is linked to $C_{1-2}$alkyl through a carbon atom and which group may carry one substituent selected from oxo, hydroxy, halogeno, $C_{1-2}$alkyl, $C_{1-2}$hydroxyalkyl and $C_{1-2}$alkoxy) or $C_{2-3}$alkyl$R^{63}$ (wherein $R^{63}$ is a group selected from morpholino, thiomorpholino, piperidino, piperazin-1-yl and pyrrolidin-1-yl which group may carry one substituent selected from oxo, hydroxy, halogeno, $C_{1-2}$alkyl, $C_{1-2}$hydroxyalkyl and $C_{1-2}$alkoxy);

6) $(CH_2)_nR^{31}$ (wherein n is an integer from 1 to 3 and $R^{31}$ is selected from a pyridone, pyridyl, imidazolyl, thiazolyl, thienyl, pyridazinyl and triazolyl group preferably from a pyridone, pyridyl, imidazolyl, thiazolyl and triazolyl group, more preferably from a pyridone, pyridyl, imidazolyl and triazolyl group and $R^{31}$ may be substituted with one substituent selected from halogeno, $C_{1-2}$alkyl, $C_{1-2}$alkoxy, $C_{1-2}$hydroxyalkyl, $C_{1-2}$hydroxyalkoxy, carboxy, cyano, $CONR^{32}R^{33}$ and $NR^{34}COR^{35}$ (wherein $R^{32}$, $R^{33}$, $R^{34}$ and $R^{35}$, which may be the same or different, each represents hydrogen, $C_{1-2}$alkyl or $C_{1-3}$alkoxy$C_{2-3}$alkyl), more preferably substituted with one substituent selected from halogeno, $C_{1-2}$alkyl, $C_{1-2}$alkoxy and cyano, especially substituted with one substituent selected from halogeno, $C_{1-2}$alkyl and cyano, more especially substituted with one substituent selected from chloro, fluoro, methyl and ethyl);

7) $C_{1-5}$alkyl$X^6R^{31}$ (wherein $X^6$ and $R^{31}$ are as defined hereinbefore);

8) ethyl$X^9$methyl$R^{31}$ (wherein $X^9$ and $R^{31}$ are as defined hereinbefore)).

More preferably $R^4$ represents hydroxy, $C_{1-3}$alkyl, amino, or a group $R^5$—$X^1$ (wherein $X^1$ is as defined hereinbefore and $R^5$ is methyl, ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyl)ethyl, 2-(N-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl, 2-(4-pyridyloxy)ethyl, 2-(4-pyridylamino)ethyl, 2-(4-oxo-1,4-dihydro-1-pyridyl)ethyl or 2-thiomorpholinoethyl, 3-thiomorpholinopropyl, 2-(2-methoxyethoxy)ethyl, 2-(4-methylpiperazin-1-yl)ethyl or 3-(4-methylpiperazin-1-yl)propyl).

According to another aspect of the present invention there is provided a compound of the formula I as defined hereinbefore with the proviso that where m is 1, $R^3$ is meta-hydroxy and with the further proviso that the compound of formula I is not 4-(2,6-dimethylphenoxy)-6,7-dimethoxycinnoline; and salts thereof, for use as a medicament.

As indicated above for a compound of formula I, as defined hereinbefore, and salts thereof, for use as a medicament:

m is advantageously an integer from 2 to 5, preferably 2 or 3, especially 3;

Z is preferably —NH—; and preferably $R^4$ represents hydroxy, $C_{1-3}$alkyl, amino, or a group $R^5$—$X^1$ (wherein $X^1$ is as defined hereinbefore and $R^5$ is methyl, ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyl)ethyl, 2-(N-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl,²-(piperazin-1-yl)ethyl, 3-(piperazin-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(1,2,3-triazol-1-yl)ethyl, 2-(1,2,3-triazol-2-yl)ethyl, 2-(1,2,4-triazool-1-yl)ethyl, 2-(1,2,4-triazol-4-yl)ethyl, 4-pyridylmethyl, 2-(4-pyridyl)ethyl, 3-(4-pyridyl)propyl, 2-(4-pyridyloxy)ethyl, 2-(4-pyridylamino)ethyl, 2-(4-oxo-1,4-dihydro-1-pyridyl)ethyl or 2-thiomorpholinoethyl, 3-thiomorpholinopropyl, 2-(2-methoxyethoxy)ethyl, 2-(4-methylpiperazin-1-yl)ethyl or 3-(4-methylpiperazin-1-yl)propyl).

According to a further aspect of the present invention there is provided a compound of the formula I as defined hereinbefore with the proviso that where m is 1, $R^3$ is meta-hydroxy and with the further proviso that the phenyl group bearing $(R^3)_m$ is not 3,4-dimethyiphenyl and that when the phenyl group bearing $(R^3)_m$ is 2,5-dichlorophenyl, 3,5-dichlorophenyl, 2,3-dichlorophenyl, 2,4-dichlorophenyl, 3,4-dichlorophenyl, 2,6-dichlorophenyl, 2,6-dimethylphenyl, 2-bromo-4-chlorophenyl, 4-bromo-2-chlorophenyl, 2-bromo-4-methylphenyl, 2-chloro-4-methylphenyl, 2-chloro-4-hydroxyphenyl, 3-chloro-4-hydroxyphenyl, 3,5-dichloro-4-hydroxyphenyl, 2,5-dichloro-4-hydroxyphenyl or 5-chloro-2-methylphenyl, Z is —NH—; and salts thereof.

According to a further aspect of the present invention there is provided a compound of the formula I as defined hereinbefore with the proviso that where m is 1, $R^3$ is meta-hydroxy and with the further proviso that the phenyl group bearing $(R^3)_m$ is not 3,4-dimethylphenyl and that when the phenyl group bearing $(R^3)_m$ is 2,5-dichlorophenvi, 3,5-dichlorophenyl, 2,3-dichlorophenyl, 2,4-dichlorophenyl, 3,4-dichlorophenyl, 2,6-dichlorophenyl, 2,6-dimethylphenyl, 3,4-dimethoxyphenyl, 2-bromo-4-chlorophenyl, 4-bromo-2-chlorophenyl, 2-bromo-4-methylphenyl, 2-chloro-4-methylphenyl, 2-chloro-4-hydroxyphenyl, 3-chloro-4-hydroxyphenyl, 3,5-dichloro-4-hydroxyphenyl, 2,5-dichloro-4-hydroxyphenyl or 5-chloro-2-methylphenyl, Z is —NH—; and salts thereof.

As indicated above for a compound of formula I, as defined hereinbefore, and salts thereof:

m is advantageously an integer from 2 to 5, preferably 2 or 3, especially 3;

Z is preferably —NH—; and preferably $R^4$ represents hydroxy, $C_{1-3}$alkyl, amino, or a group $R^5$—$X^1$ (wherein $X^1$ is as defined hereinbefore and $R^5$ is methyl, ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl 2-(methylsulphonyl)ethyl, 2-(N,N-dimethylsulphamoyl)ethyl, 2-(N-methylsulphamoyl)ethyl, 2-sulphamoylethyl, 2-(N,N-dimethylamino)ethyl, 3-(N-dimethylamino)propyl, 2-morpholinoethyl, 3-morpholinoptopyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino)propyl, 2-methylthiazol-4-ylmethyl, 2-acetamidothiazol-4-ylmethyl, 1-methylimidazol-2-ylmethyl, 2-(imidazol-1-yl)ethyl, 2-(1,2,3-triazol-1-yl)ethyl, 2-(1,2,3-triazol-2-yl)ethyl, 2-(1,2,4-triazol-1-yl)ethyl, 2-(1,2,4-triazol-4-yl)ethyl, 4-pyridylmethyl, 2-(4-pyridyl)ethyl, 3-(4-pyridyl)propyl 2-(4-pyridyloxy)ethyl, 2-(4-pyridylamino)ethyl, 2-(4-oxo-1,4-dihydro-1-pyridyl)ethyl or 2-thiomorpholinoethyl, 3-thiomorpholinopropyl, 2-(2-methoxyethoxy)ethyl, 2-(4-methylpiperazin-1-yl)ethyl or 3-(4-methylpiperazin-1-yl)propyl).

In a particular embodiment of the present invention there is provided the use of a compound of the formula Ia:

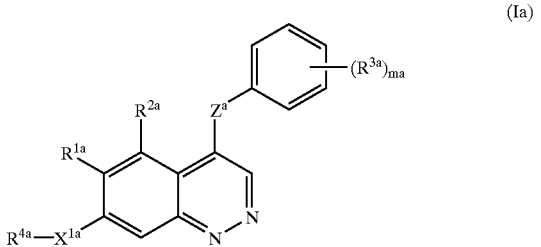

(Ia)

[(wherein:

$Z^a$ represents —O—, —NH—, —S— or —CH$_2$—;

ma is an integer from 1 to 5;

$R^{1a}$ represents hydrogen, hydroxy, halogeno, $C_{1-3}$alkyl, $C_{1-3}$alkoxy, $C_{1-3}$alkylthio or $NR^{5a}R^{6a}$ (wherein $R^{5a}$ and $R^{6a}$, which may be the same or different, each represents hydrogen or $C_{1-3}$alkyl);

$R^{2a}$ represents hydrogen, hydroxy, fluoro, methoxy, amino or nitro;

$R^{3a}$ represents hydroxy, halogeno, $C_{1-3}$alkyl, $C_{1-3}$alkoxy, $C_{1-3}$alkanoyloxy, trifluoromethyl, cyano, amino or nitro;

$X^{1a}$ represents —O—, —CH$_2$—, —S— or $NR^{7a}$ (wherein $R^{7a}$ represents hydrogen or $C_{1-3}$ alkyl);

$R^{4a}$ is selected from the following:

1) $C_{1-5}$alkyl, $C_{1-5}$hydroalkyl, $C_{1-5}$aminoalkyl;

2) $C_{1-5}$alkyl$X^{2a}COR^{9a}$ (wherein $X^{2a}$ represents —O— or $NR^{8a}$ (in which $R^{8a}$ represents hydrogen, $C_{1-3}$alkyl or $C_{1-3}$ alkoxy$C_{2-3}$alkyl) and $R^{9a}$ represents $NR^{10a}R^{11a}$ or $OR^{12a}$ (wherein $R^{10a}$, $R^{11a}$ and $R^{12a}$ which may be the same or different are each hydrogen, $C_{1-3}$alkyl or $C_{1-3}$alkoxy$C_{2-3}$alkyl) with the proviso that when $X^{2a}$ is —O—, $R^{9a}$ is not $OR^{12a}$);

3) $C_{1-5}$alkyl$X^{3a}R^{14a}$ (wherein $X^{3a}$ represents —O—, —S—, —SO—, —SO$_2$— or $NR^{13a}$ (wherein $R^{13a}$ is hydrogen, $C_{1-3}$alkyl or $C_{1-3}$alkoxy$C_{2-3}$alkyl) and $R^{14a}$ represents $C_{1-3}$alkyl, cyclopentyl or cyclohexyl);

4) $C_{1-5}$alkyl$X^{4a}C_{1-5}$alkyl$X^{5a}R^{15a}$ (wherein $X^{4a}$ and $X^{5a}$ which may be the same or different are each —O—, —S—, or $NR^{16a}$ (wherein $R^{16a}$ is hydrogen or $C_{1-3}$alkyl) and $R^{15a}$ represents hydrogen or $C_{1-3}$alkyl);

5) $C_{1-5}$alkylsulphonyl$NR^{17a}R^{18a}$ (wherein $R^{17a}$ and $R^{18a}$ which may be the same or different are each hydrogen, $C_{1-3}$ alkyl or $C_{1-3}$alkoxy$C_{2-3}$alkyl);

6) $C_{1-5}$alkyl$R^{19a}$ (wherein $R^{19a}$ is a 5 or 6 membered saturated heterocyclic group with one or two heteroatoms, selected independently from O, S and N, which heterocyclic group may bear one or two substituents selected from halogeno, $C_{1-4}$alkyl, $C_{1-4}$hydroxyalkyl and $C_{1-4}$alkoxy); and 7) $(CH_2)_{na}R^{20a}$ (wherein na is an integer from 0 to 5 and $R^{20a}$ is a phenyl group or a 5 or 6 membered aromatic heterocyclic group with 1 to 3 heteroatoms selected from O, N and S, which phenyl or aromatic heterocyclic group may carry up to 5 substituents selected from halogeno, $C_{1-4}$alkyl, $C_{1-4}$alkoxy, $C_{1-4}$hydroxyalkyl, $C_{1-4}$hydroxyalkoxy, carboxy, cyano. $CONR^{21a}R^{22a}$ and $NR^{23a}COR^{24a}$ (wherein $R^{21a}$, $R^{22a}$, $R^{23a}$ and $R^{24a}$, which may be the same or different, each represents hydrogen or $C_{1-4}$alkyl)];

and salts thereof in the manufacture of a medicament for use in the production of an antiangiogenic and/or vascular permeability reducing effect in a warm-blooded animal such as a human being.

In a particular embodiment of the present invention there is provided a method for producing an antiangiogenic and/or vascular permeability reducing effect in a warm-blooded animal in need of such treatment which comprises administering to said animal an effective amount of a compound of formula Ia, as defined hereinbefore, or a pharmaceutically acceptable salt thereof.

$Z^a$ is advantageously —S—, preferably —O—, but especially —NH—.

ma is advantageously an integer from 2 to 5, preferably 2 or 3, especially 3.

$R^{1a}$ is advantageously hydrogen, hydroxy, $C_{1-3}$alkyl, $C_{1-3}$alkoxy or amino.

$R^{1a}$ is preferably hydrogen, hydroxy, methyl, ethyl, methoxy or ethoxy, more preferably hydrogen, hydroxy, methyl or methoxy but especially methoxy.

$R^{2a}$ is preferably hydrogen, amino or nitro, but especially hydrogen.

In one embodiment of the present invention $R^{3a}$ represents hydroxy, halogeno. $C_{1-3}$alkyl, $C_{1-3}$alkoxy, trifluoromethyl, cyano, amino or nitro.

Advantageously in another embodiment of the present invention one $R^{3a}$ substituent is meta-hydroxy and the other one or more are each selected from halogeno, methyl and methoxy.

In another embodiment of the invention the phenyl group bearing $(R^{3a})_{ma}$ is preferably of the formula IIaa:

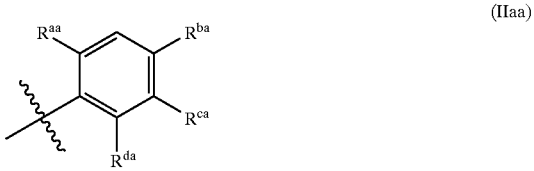

(IIaa)

wherein:

$R^{aa}$ represents hydrogen, methyl, fluoro or chloro, preferably hydrogen, fluoro or chloro, especially fluoro;

$R^{ba}$ represents hydrogen, methyl, methoxy, bromo, fluoro or chloro;

$R^{ca}$ represents hydrogen or hydroxy, especially hydroxy;

$R^{da}$ represents hydrogen, fluoro or chloro, especially fluoro.

Preferably in another embodiment of the invention two $R^{3a}$ substituents are halogeno, especially ortho, ortho'-difluoro, and the other one or more are each selected from halogeno and methyl.

In a particular aspect of the present invention, the phenyl group bearing $(R^{3a})_{ma}$ is the 2-fluoro-5-hydroxy-4-methylphenyl group, the 4-chloro-2-fluoro-5-hydroxyphenyl group, the 4-bromo-2,6-difluorophenyl group, the 4-chloro-2,6-difluorophenyl group or the 4-chloro-2-fluorophenyl group.

$X^{1a}$ is preferably —O—.

Conveniently $R^{4a}$ is selected from one of the following seven groups:

1) $C_{1-5}$alkyl, $C_{2-5}$hydroxyalkyl, $C_{1-5}$fluoroalkyl, $C_{2-5}$aminoalkyl;

2) $C_{2-3}$alkyl$X^{2a}COR^{9a}$ (wherein $X^{2a}$ represents —O— or $NR^{8a}$ (wherein $R^{8a}$ represents hydrogen, $C_{1-3}$alkyl or $C_{1-2}$alkoxyethyl) and $R^{9a}$ represents $NR^{10a}R^{11a}$ or $OR^{12a}$ (wherein $R^{10a}$, $R^{11a}$ and $R^{12a}$ which may be the same or different are each $C_{1-2}$alkyl or $C_{1-2}$alkoxyethyl) with the proviso that when $X^{2a}$ is —O—, $R^{9a}$ is not $OR^{12a}$);

3) $C_{2-4}$alkyl$X^{3a}R^{14a}$ (wherein $X^{3a}$ represents —O—, —S—, —SO—, —SO$_2$— or $NR^{13a}$ (wherein $R^{13a}$ is hydrogen, $C_{1-3}$alkyl or $C_{1-2}$alkoxyethyl) and $R^{14a}$ represents $C_{1-3}$alkyl, cyclopentyl or cyclohexyl);

4) $C_{2-3}$alkyl$X^{4a}C_{2-3}$alkyl$X^{5a}R^{15a}$ (wherein $X^{4a}$ and $X^{5a}$ which may be the same or different are each —O—, —S—, or $NR^{16a}$ (wherein $R^{16a}$ is hydrogen or $C_{1-3}$alkyl) and $R^{15a}$ represents hydrogen or $C_{1-3}$alkyl);

5) $C_{1-4}$alkylsulphonyl$NR^{17a}R^{18a}$ (wherein $R^{17a}$ and $R^{18a}$ which may be the same or different are each hydrogen, $C_{1-3}$alkyl or $C_{1-2}$alkoxyethyl);

6) $C_{1-5}$alkyl$R^{25a}$ (wherein $R^{25a}$ is a 5 or 6 membered saturated heterocyclic group with one or two heteroatoms, selected independently from O, S and N, which heterocyclic group is linked to $C_{1-5}$alkyl through a carbon atom and which heterocyclic group may bear one or two substituents selected from halogeno, $C_{1-4}$alkyl, $C_{1-4}$hydroxyalkyl and $C_{1-4}$alkoxy) or $C_{2-5}$alkyyl$R^{26a}$ (wherein $R^{26a}$ is a 5 or 6 membered saturated heterocyclic group with one or two heteroatoms of which one is N and the other is selected independently from O, S and N, which heterocyclic group is linked to $C_{2-5}$alkyl through a nitrogen atom and which heterocyclic group may bear one or two substituents selected from halogeno, $C_{1-4}$alkyl, $C_{1-4}$hydroxyalkyl and $C_{1-4}$alkoxy); and 7) $(CH_2)_{na}R^{20a}$ (wherein na is an integer from 0 to 4 and $R^{20a}$ is a phenyl group or a 5 or 6 membered aromatic heterocyclic group with 1 to 3 heteroatoms selected from O, N and S, of which preferably one is N, which phenyl or aromatic heterocyclic group may be substituted as hereinbefore defined, advantageously substituted with up to 2 substituents as hereinbefore defined, more preferably substituted with one substituent selected from the group of substituents as hereinbefore defined).

Advantageously $R^{4a}$ is selected from one of the following seven groups:

1) $C_{1-4}$alkyl, $C_{2-4}$hydroxyalkyl, $C_{1-4}$fluoroalkyl, $C_{2-4}$aminoalkyl;

2) $C_{2-3}$alkyl$X^{2a}COR^{9a}$ (wherein $X^{2a}$ represents —O— or $NR^{8a}$ (wherein $R^{8a}$ represents hydrogen, $C_{1-3}$alkyl or $C_{1-2}$alkoxyethyl) and $R^{9a}$ represents $NR^{10a}R^{11a}$ or $OR^{12a}$ (wherein $R^{10a}$, $R^{11a}$ and $R^{12a}$ which may be the same or different are each $C_{1-2}$alkyl or $C_{1-2}$alkoxyethyl) with the proviso that when $X^{2a}$ is —O—, $R^{9a}$ is not $OR^{12a}$);

3) $C_{2-4}$alkyl$X^{3a}R^{14a}$ (wherein $X^{3a}$ represents —O—, —S—, —SO—, —SO$_2$— or $NR^{13a}$ (wherein $R^{13a}$ is hydrogen, $C_{1-3}$alkyl or $C_{1-2}$alkoxyethyl) and $R^{14a}$ represents $C_{1-3}$alkyl, cyclopentyl or cyclohexyl);

4) $C_{2-3}$alkyl$X^{4a}C_{2-3}$alkyl$X^{5a}R^{15a}$ (wherein $X^{4a}$ and $X^{5a}$ which may be the same or different are each —O—, —S—, or $NR^{16a}$ (wherein $R^{16a}$ is hydrogen or $C_{1-3}$alkyl) and $R^{15a}$ represents hydrogen or $C_{1-3}$alkyl);

5) $C_{1-4}$alkylsulphonyl$NR^{17a}R^{18a}$ (wherein $R^{17a}$ and $R^{18a}$ which may be the same or different are each hydrogen, $C_{1-3}$alkyl or $C_{1-2}$alkoxyethyl);

6) $C_{1-4}$alkyl$R^{25a}$ (wherein $R^{25a}$ is selected from pyrrolidinyl, piperazinyl, piperidyl, 1,3-dioxolan-2-yl, 1,3-dioxan-2-yl, 1,3-dithiolan-2-yl and 1,3-dithian-2-yl, such that $R^{25a}$ is linked to $C_{1-4}$alkyl through a carbon atom) or $C_{2-4}$alkyl$R^{26a}$ (wherein $R^{26a}$ is selected from morpholino, pyrrolidin-1-yl, piperazin-1-yl and piperidino); and 7) $(CH_2)_{na}R^{20a}$ (wherein na is an integer from 1 to 3 and $R^{20a}$ is a 5 or 6 membered aromatic heterocyclic group with 1 to 2 heteroatoms selected from O, N and S, of which preferably one is N, which aromatic heterocyclic group may be substituted as hereinbefore defined, preferably substituted with one substituent selected from halogeno, $C_{1-2}$alkyl, $C_{1-2}$alkoxy, $C_{1-2}$hydroxyalkyl, $C_{1-2}$hydroxyalkoxy, carboxy, cyano, $CONR^{21a}R^{22a}$ and $NR^{23a}COR^{24a}$ (wherein $R^{21a}$, $R^{22a}$, $R^{23a}$ and $R^{24a}$, which may be the same or different, each represents hydrogen or $C_{1-2}$alkyl)).

Preferably $R^{4a}$ is selected from one of the following seven groups:

1) $C_{1-3}$alkyl, $C_{2-3}$hydroxyalkyl, $C_{1-3}$fluoroalkyl, $C_{2-3}$aminoalkyl;

2) 2-(3,3-dimethylureido)ethyl, 3-(3,3dimethylureido) propyl, 2-(3-methylureido)ethyl, 3-methylureido) propyl, 2-ureidoethyl, 3-ureidopropyl, 2-(N,N-dimethylcarbamoyloxy)ethyl, 3-(N,N-dimethylcarbamoyloxy)propyl, 2-(N-methylcarbarnoyloxy)ethyl, 3-(N-methylcarbamoyloxy)propyl, 2-(carbamoyloxy)ethyl, 3-(carbamoyloxy)propyl;

3) $C_{2-3}$alkyl$X^{3a}R^{14a}$ (wherein $X^{3a}$ represents —O—, —S—, —SO—, —SO$_2$— or $NR^{13a}$ (wherein $R^{13a}$ is hydrogen, $C_{1-2}$alkyl or $C_{1-2}$alkoxyethyl) and $R^{14a}$ represents $C_{1-2}$alkyl, cyclopentyl or cyclohexyl);

4) $C_{2-3}$alkyl$X^{4a}C_{2-3}$alkyl$X^{5a}R^{15a}$ (wherein $X^{4a}$ and $X^{5a}$ which may be the same or different are each —O—, or —NH— and $R^{15a}$ represents hydrogen or $C_{1-2}$alkyl);

5) $C_{1-3}$alkylsulphonyl$NR^{17a}R^{18a}$ (wherein $R^{17a}$ and $R^{18a}$ which may be the same or different are each hydrogen or methyl);

6) $C_{1-2}$alkyl$R^{25a}$ (wherein $R^{25a}$ is selected from pyrrolidinyl, piperazinyl, piperidyl, 1,3-dioxolan-2-yl, 1,3-dioxan-2-yl, 1,3-dithiolan-2-yl and 1,3-dithian-2-yl, such that $R^{25a}$ is linked to $C_{1-2}$alkyl through a carbon atom) or $C_{2-3}$alkyl$R^{26a}$ (wherein $R^{26a}$ is selected from morpholino, piperidino, piperazin-1-yl and pyrrolidin-1-yl); and 7) $(CH_2)_{na}R^{20a}$ (wherein na is an integer from 1 to 3 and $R^{20a}$ is selected from pyridyl, imidazolyl, thiazolyl, thienyl and pyridazinyl, preferably from pyridyl, imidazolyl and thiazolyl and $R^{20a}$ may be substituted with one substituent selected from halogeno, $C_{1-2}$alkyl, $C_{1-2}$alkoxy, $C_{1-2}$hydroxyalkyl, $C_{1-2}$hydroxyalkoxy, carboxy, cyano, $CONR^{21a}R^{22a}$ and $NR^{23a}COR^{24a}$ (wherein $R^{21a}$, $R^{22a}$, $R^{23a}$ and $R^{24a}$, which may be the same or different, each represents hydrogen or $C_{1-2}$alkyl), more preferably substituted with one substituent selected from halogeno, $C_{1-2}$alkyl and cyano, especially substituted with one substituent selected from chloro, fluoro, methyl and ethyl).

More preferably $R^{4a}$ represents methyl, ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyl)ethyl, 2-(N-methylsulphamoyl) ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yi)propyl, 2-(pyrrolidin-1-yl)ethyl, 3-(pyrrolidin-1-yl)propyl, (1,3-dioxolan-2-yl)methyl, 2-(1,3-dioxolan-2-yl)ethyl, 2-(2-methoxyethylamino)ethyl, 2-(2-hydroxyethylamino)ethyl, 3-(2-methoxyethylamino)propyl, 3-(2-hydroxyethylamino) propyl, 2-methylthiazol-4-ylmethyl, 1-methylimidazol-2-ylmethyl, 4-pyridylmethyl, 2-(4-pyridyl)ethyl or 3-(4-pyridyl)propyl.

In a further embodiment of the present invention there is provided a compound of the formula Ia as defined hereinbefore with the proviso that where ma is 1, $R^{3a}$ is meta-hydroxy and with the further proviso that the compound of formula Ia is not 4-(2,6-dimethylphenoxy)-6,7-dimethoxycinnoline; and salts thereof, for use as a medicament.

As indicated above for a compound of formula Ia, as defined hereinbefore, and salts thereof, for use as a medicament:

ma is advantageously an integer from 2 to 5, preferably 2 or 3, especially 3;

$Z^a$ is preferably —NH—;

$X^{1a}$ is preferably —O—; and preferably $R^{4a}$ represents methyl, ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyi)ethyl, 2-(N-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl,3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, (1,3-dioxolan-2-yl) methyl, 2-(1,3-dioxolan-2-yl)ethyl, 2-(2-methoxyethylamino)ethyl, 2-(2-hydroxyethylamino) ethyl, 3-(2-methoxyethylamino)propyl, 3-(2-hydroxyethylamino)propyl, 2-methylthiazol-4-ylmethyl, 1-methylimidazol-2-ylmethyl, 4-pyridylmethyl, 2-(4-pyridyl)ethyl or 3-(4-pyridyl) propyl.

In a further embodiment of the present invention there is provided a compound of the formula Ia as defined hereinbefore with the proviso that where ma is 1, $R^{3a}$ is meta-hydroxy and with the further proviso that the phenyl group bearing $(R^{3a})_{ma}$ is not 3,4-dimethyiphenyl and that when the phenyl group bearing $(R^{3a})_{ma}$ is 2,5-dichlorophenyl, 3,5-dichlorophenyl, 2,3-dichlorophenyl, 2,4-dichlorophenyl, 3,4-dichlorophenyl, 2,6-dichlorophenyl, 2,6-dimethylphenyl, 2-bromo-4-chlorophenyl, 4-bromo-2-chlorophenyl, 2-bromo-4-methylphenyl, 2-chloro-4-methylphenyl, 2-chloro-4-hydroxyphenyl, 3-chloro-4-hydroxyphenyl, 3,5-dichloro-4-hydroxyphenyl, 2,5-dichloro-4-hydroxyphenyl or 5-chloro-2-methylphenyl, $Z^a$ is —NH—; and salts thereof.

In a further embodiment of the present invention there is provided a compound of the formula Ia as defined hereinbefore with the proviso that where ma is 1, $R^{3a}$ is meta-hydroxy and with the further proviso that the phenyl group bearing $(R^{3a})_{ma}$ is not 3,4-dimethylphenyl and that when the phenyl group bearing $(R^{3a})_{ma}$ is 2,5-dichlorophenyl, 3,5-dichlorophenyl, 2,3-dichlorophenyl, 2,4-dichlorophenyl, 3,4-dichlorophenyl, 2,6-dichlorophenyl, 2,6-dimethylphenyl, 3,4-dimethoxyphenyl, 2-bromo-4-chlorophenyl, 4-bromo-2chlorophenyl, 2-bromo-4-methylphenyl, 2-chloro-4-methylphenyl, 2-chloro-4-hydroxyphenyl, 3-chloro-4-hydroxyphenyl, 3,5-dichloro-4-hydroxyphenyl, 2,5-dichloro-4-hydroxyphenyl or 5-chloro-2-methylphenyl, $Z^a$ is —NH—; and salts thereof.

As indicated above for a compound of formula Ia, as defined hereinbefore, and salts thereof:

ma is advantageously an integer from 2 to 5, preferably 2 or 3, especially 3;

$Z^a$ is preferably —NH—;

$X^{1a}$ is preferably —O—; and preferably $R^{4a}$ represents methylh ethyl, trifluoromethyl, 2,2,2-trifluoroethyl, 2-hydroxyethyl, 3-hydroxypropyl, 2-methoxyethyl, 3-methoxypropyl, 2-(methylsulphinyl)ethyl, 2-(methylsulphonyl)ethyl, 2-(N,N-dimethylsulphamoyl)ethyl, 2-(-methylsulphamoyl)ethyl, 2-sulphamoylethyl, 2-(N,N-dimethylamino)ethyl, 3-(N,N-dimethylamino)propyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl) ethyl, 3-(pyrrolidin-1-yl)propyl, (1,3-dioxolan-2-yl) methyl, 2-(1,3-dioxolan-2-yl)ethyl, 2-(2-methoxyethylamino)ethyl, 2-(2-hydroxyethylamino) ethyl, 3-(2-methoxyethylamino)propyl, 3-(2-hydroxyethylamino)propyl. 2-methylthiazol-4-ylmethyl, 1-methylimidazol-2-ylmethyl, 4-pyridylmethyl, 2-(4-pyridyl)ethyl or 3-(4-pyridyl) propyl.

In a further particular embodiment of the current invention there is provided a compound of the formula Ib:

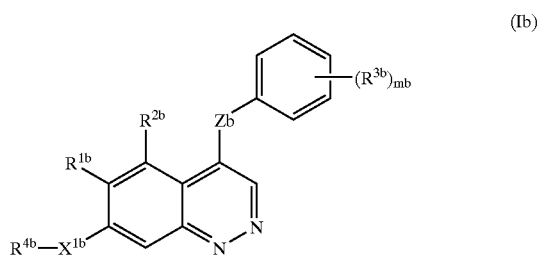

(Ib)

[wherein $R^{1b}$ is hydrogen, $C_{1-3}$alkoxy, preferably methoxy, or halogeno, preferably chloro;

$R^{2b}$ is hydrogen;

$X^{1b}$ is —O—;

$R^{4b}$ is $C_{1-3}$alkyl, 2-($C_{1-3}$alkoxy)ethyl, benzyl, 4-pyridyl ($C_{1-3}$alkyl), morpholino($C_{1-3}$alkyl), pyrrolidino($C_{1-3}$alkyl), 2-methylthiazol-4-yl($C_{1-3}$alkyl), 1-methylimidazol-2-yl($C_{1-3}$alkyl) and 2-(($C_{1-3}$alkoxy)($C_{1-3}$alkoxy))ethyl;

$Z^b$ is —NH— or —O—;

mb is 2 or 3; and the phenyl group bearing $(R^{3b})_{mb}$ is selected from: 3-hydroxy-4-methylphenyl, 4-chloro-2-fluorophenyl, 4-bromo-2-fluorophenyl, 4-chloro-2-fluoro-5-hydroxyphenyl, 5-acetoxy-4-chloro-2-fluorophenyl, 2-fluoro-5-hydroxy-4-methylphenyl and 4-bromo-2-fluoro-5-20 hydroxyphenyl]; and salts thereof.

Particularly preferred compounds of the present invention by virtue of their good activity against VEGF receptor tyrosine kinase activity and their lack of significant activity against epidermal growth factor (EGF) receptor tyrosine kinase include:

4-(4-chloro-2-fluoro-5-hydroxyanilino)-6-methoxy-7(2-methoxyethoxy)cinnoline, 4-(4-bromo-2-fluoro-5-hydroxyanilino)-6-methoxy-7-(2-methoxyethoxy)cinnoline, 4-(2-fluoro-5-hydroxy-4-methylanilino)-6-methoxy-7-(2-methoxyethoxy)cinnoline, 4-(2-fluoro-5-hydroxy-4-methylanilino)-6-methoxy-7-(3-morpholinopropoxy)cinnoline, 4-(2-fluoro-5-hydroxy-4-methylanilino)-6-methoxy-7-[(2-methylthiazol-4-yl)methoxy]cinnoline, 4-(2-fluoro-5-hydroxy-4-methylanilino)-6-methoxy-7-[(1-methylimidazol-2-yl)methoxy]cinnoline, and especially the salts thereof, particularly the hydrochloride salts thereof.

Another particularly preferred compound is 4-(2-fluoro-5-hydroxy-4-methylanilino)-6-methoxy-7-(3-pyrrolidinopropoxy)cinnoline especially the salts thereof, particularly the hydrochloride salts thereof.

Especially preferred compounds are:

4-(4-chloro-2-fluoro-5-hydroxyanifino)-6-methoxy-7-(2-methoxyethoxy)cinoline, 4-(4-bromo-2-fluoro-5-hydroxyanilino)-6-methoxy-7-(2-methoxyethoxy)cinnoline, 4-(2-fluoro-5-hydroxy-4-methylanilino)-6-methoxy-7-(2-methoxyethoxy)cinnoline, 4-(2-fluoro-5-hydroxy-4-methylanilino)-6-methoxy-7-(3-morpholinopropoxy)cinnoline, 4-(2-fluoro-5-hydroxy-4-methylanilino)-6-methoxy-7-[(2-methylthiazol-4-yl)methoxy]cinnoline, 4-(2-fluoro-5-hydroxy-4-methylanilino)-6-methoxy-7-(3-pyrrolidinopropoxy)cinnoline and especially the salts thereof, particularly the hydrochloride salts thereof.

For the avoidance of doubt it is to be understood that where in this specification a group is qualified by 'hereinbefore defined' or 'defined hereinbefore' the said group encompasses the first occurring and broadest definition as well as each and all of the preferred definitions for that group.

In this specification unless stated otherwise the term "alkyl" includes both straight and branched chain alkyl groups but references to individual alkyl groups such as "propyl" are specific for the straight chain version only. An analogous convention applies to other generic terms. Unless otherwise stated the term "alkyl" advantageously refers to chains with 1–6 carbon atoms, preferably 1–4 carbon atoms. The term "alkoxy" as used herein, unless stated otherwise includes "alkyl" —O— groups in which "alkyl" is as hereinbefore defined. The term "aryl" as used herein unless stated otherwise includes reference to a $C_{6-10}$aryl group which may, if desired, carry one or more substituents selected from halogeno, alkyl, alkoxy, nitro, trifluoromethyl and cyano, (wherein alkyl and alkoxy are as hereinbefore defined). The term "aryloxy" as used herein unless otherwise stated includes "aryl" —O— groups in which "aryl" is as hereinbefore defined. The term "sulphonyloxy" as used herein refers to alkylsulphonyloxy and aryisulphonyloxy groups in which "alkyl" and "aryl" are as hereinbefore defined. The term "alkanoyl" as used herein unless otherwise stated includes alkyl C=O groups in which "alkyl" is as defined hereinbefore for example ethanoyl refers to $CH_3C=O$. In this specification unless stated otherwise the term "alkenyl" includes both straight and branched chain alkenyl groups but references to individual alkenyl groups such as 2-butenyl are specific for the straight chain version only. Unless otherwise stated the term "alkenyl" advantageously refers to chains with 2–5 carbon atoms, preferably 3–4 carbon atoms. In this specification unless stated otherwise the term "alkynyl" includes both straight and branched chain alkynyl groups but references to individual alkynyl groups such as 2-butynyl are specific for the straight chain version only. Unless otherwise stated the term "alkynyl" advantageously refers to chains with 2–5 carbon atoms, preferably 3–4 carbon atoms.

In formula I, as hereinbefore defined, hydrogen will be present at positions 3 and 8 of the cinnoline group.

Within the present invention it is to be understood that a cinnoline of the formula I or a salt thereof may exhibit the phenomenon of tautomerism and that the formulae drawings within this specification can represent only one of the possible tautomeric forms. It is to be understood that the invention encompasses any tautomeric form which inhibits VEGF receptor tyrosine kinase activity and is not to be limited merely to any one tautomeric form utilised within the formulae drawings.

It is also to be understood that certain cinnolines of the formula I and salts thereof can exist in solvated as well as unsolvated forms such as, for example, hydrated forms. It is to be understood that the invention encompasses all such solvated forms which inhibit VEGF receptor tyrosine kinase activity.

For the avoidance of any doubt, it is to be understood that when $X^1$ is, for example, a group of formula —$NR^8CO$—, it is the nitrogen atom bearing the $R^8$ group which is attached to the cinnoline ring and the carbonyl (CO) group is attached to $R^5$, whereas when $X^1$ is, for example, a group of formula —$CONR^9$—, it is the carbonyl group which is attached to the cinnoline ring and the nitrogen atom bearing the $R^9$ group is attached to $R^5$. A similar convention applies to the other two atom $X^1$ linking groups such as —$NR^{11}SO_2$— and —$SO_2NR^{10}$—. When $X^1$ is —$NR^{12}$— it is the nitrogen atom bearing the $R^{12}$ group which is linked to the cinnoline ring and to $R^5$. An analogous convention applies to other groups. It is further to be understood that when $X^1$ represents —$NR^{12}$— and $R^{12}$ is $C_{1-3}$alkoxy$C_{2-3}$alkyl it is the $C_{2-3}$alkyl moiety which is linked to the nitrogen atom of $X^1$ and an analogous convention applies to other groups.

For the avoidance of any doubt, it is to be understood that in a compound of the formula I when $R^4$ is a group $R^5$—$X^1$ and $R^5$ is, for example, a group of formula $(CH_2)_nR^{31}$, it is the tenninal $(CH_2)_n$ moiety which is bound to $X^1$, similarly when $R^5$ is, for example, a group of formula $C_{2-5}$alkenyl$R^{31}$ it is the $C_{2-5}$alkenyl moiety which is bound to $X^1$ and an analogous convention applies to other groups. When $R^5$ is a group 1-$R^{31}$prop-1-en-3-yl it is the first carbon to which the group $R^{31}$ is attached and it is the third carbon which is linked to $X^1$ and an analogous convention applies to other groups.

The present invention relates to the compounds of formula I as hereinbefore defined as well as to the salts thereof. Salts for use in pharmaceutical compositions will be pharmaceutically acceptable salts, but other salts may be useful in the production of the compounds of formula I and their pharmaceutically acceptable salts. Pharmaceutically acceptable salts of the invention may, for example, include acid addition salts of the compounds of formula I as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. In addition where the compounds of formula I are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

A compound of the formula I, or salt thereof, and other compounds of the invention (as hereinafter defined) may be prepared by any process known to be applicable to the preparation of chemically-related compounds. Such processes include, for example, those illustrated in European Patent Applications Publication Nos, 0520722, 0566226, 0602851 and 0635498. Such processes, are provided as a further feature of the invention and are as described hereinafter. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

Thus the following processes (a) to (g) and (i) to (v) constitute further features of the present invention.

Synthesis of Compounds of Formula I (a) Compounds of the formula I and salts thereof may be prepared by the reaction of a compound of the formula III:

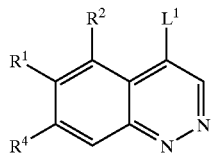

(III)

(wherein $R^1$, $R^2$ and $R^4$ are as defined hereinbefore and $L^1$ is a displaceable moiety), with a compound of the formula IV:

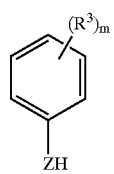

(IV)

(wherein Z, $R^3$ and m are as defined hereinbefore) whereby to obtain compounds of the formula I and salts thereof. A convenient displaceable moiety $L^1$ is, for example, a halogeno, alkoxy (preferably $C_{1-4}$alkoxy), aryloxy or sulphonyloxy group, for example a chloro, bromo, methoxy, phenoxy, methanesulphonyloxy or toluene-4-sulphonyloxy group.

The reaction is advantageously effected in the presence of either an acid or a base. Such an acid is, for example, an anhydrous inorganic acid such as hydrogen chloride. Such a base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or for example, an alkali metal or alkaline earth metal carbonate or hydroxide, for example sodium carbonate, potassium carbonate, calcium carbonate, sodium hydroxide or potassium hydroxide. Alternatively such a base is, for example, an alkali metal hydride, for example sodium hydride, or an alkali metal or alkaline earth metal amide, for example sodium amide or sodium bis(trimethylsilyl)amide. The reaction is preferably effected in the presence of an inert solvent or diluent, for example an alkanol or ester such as methanol, ethanol, isopropanol or ethyl acetate, a halogenated solvent such as methylene chloride, trichloromethane or carbon tetrachloride, an ether such as tetrahydrofuran or 1,4-dioxan, an aromatic hydrocarbon solvent such as toluene, or a dipolar aprotic solvent such as N,N-dimethylformamide, N,N-dimethylacetamide, N-methylpyrrolidin-2-one or dimethylsulphoxide. The reaction is conveniently effected at a temperature in the range, for example, 10 to 150° C., preferably in the range 20 to 80° C.

The compound of the invention may be obtained from this process in the form of the free base or alternatively it may be obtained in the form of a salt with the acid of the formula H-$L^1$ wherein $L^1$ has the meaning defined hereinbefore. When it is desired to obtain the free base from the salt, the salt may be treated with a base as defined hereinbefore using a conventional procedure.

(b) Where the group of formula IIa:

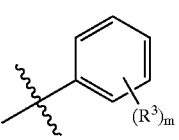

(IIa)

(wherein $R^3$ and m are as hereinbefore defined) represents a phenyl group carrying one or more hydroxy groups, a compound of the formula I and salts thereof can be prepared by the deprotection of a compound of formula V:

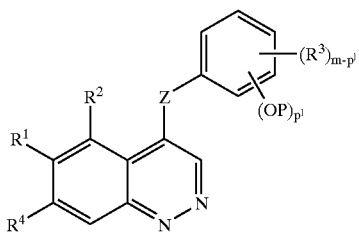

(V)

(wherein m, $R^1$, $R^2$, $R^3$, $R^4$ and Z are as hereinbefore defined. P represents a phenolic hydroxy protecting group and p is an integer from 1 to 5 equal to the number of protected hydroxy groups and such that m-p¹ is equal to the number of $R^3$ substituents which are not protected hydroxy). The choice of phenolic hydroxy protecting group P is within the standard knowledge of an organic chemist, for example those included in standard texts such as "Protective Groups in Organic Synthesis" T. W. Greene and R. G. M. Wuts, 2nd Ed. Wiley 1991, including ethers (for example, methyl, methoxymethyl, allyl and benzyl), silyl ethers (for example, t-butyldiphenylsilyl and t-butyldimethylsilyl), esters (for example, acetate and benzoate) and carbonates (for example, methyl and benzyl). The removal of such a phenolic hydroxy protecting group may be effected by any of the procedures known for such a transformation, including those reaction conditions indicated in standard texts such as that indicated hereinbefore, or by a related procedure. The reaction conditions preferably being such that the hydroxy derivative is produced without unwanted reactions at other sites within the starting or product compounds. For example, where the protecting group P is acetate, the transformation may conveniently be effected by treatment of the cinnoline derivative with a base as defined hereinbefore and including ammonia, and its mono and di-alkylated derivatives, preferably in the presence of a protic solvent or co-solvent such as water or an alcohol, for example methanol or ethanol. Such a reaction can be effected in the presence of an additional inert solvent or diluent as defined hereinbefore and at a temperature in the range 0 to 50° C., conveniently at about 20° C.

(c) Production of those compounds of formula I and salts thereof wherein the substituent $R^4$ represents $R^5$—$X^1$ and $X^1$ is —O—, —S— or —NR$^{12}$— (wherein $R^{12}$ is as hereinbefore defined) can be achieved by the reaction, conveniently in the presence of a base as defined hereinbefore, of a compound of the formula VI:

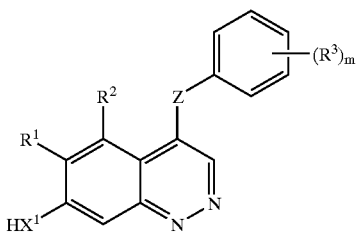

(VI)

(wherein m, $X^1$, $R^1$, $R^2$, $R^3$, and Z are as hereinbefore defined) with a compound of formula VII:

$R^5$—$L^1$ (VII)

(wherein $R^5$ and $L^1$ are as hereinbefore defined); $L^1$ is a displaceable moiety for example a halogeno or sulphonyloxy group such as a bromo or methanesulphonyloxy group.

The reaction is preferably effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 50° C.

(d) Compounds of the formula I and salts thereof wherein the substituent $R^4$ represents $R^5$—$X^1$ may be prepared by the reaction of a compound of the formula VII:

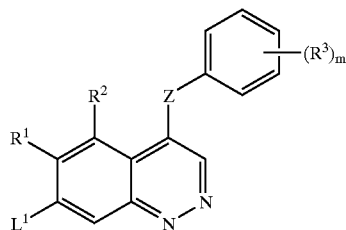

(VIII)

with a compound of the formula IX:

$R^5$—$X^1$—H (IX)

(wherein $L^1$, $R^1$, $R^2$, $R^3$, $R^5$, Z, m and $X^1$ are all as hereinbefore defined). The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

(e) Compounds of the formula I and salts thereof wherein $R^4$ represents $R^5$—$X^1$ and $R^5$ is $C_{1-5}$alkyl$R^{64}$, [wherein $R^{64}$ is selected from one of the following four groups:

1) $X^{10}C_{1-3}$alkyl (wherein $X^{10}$ represents —O—, —S—, —SO$_2$—, NR$^{65}$CO, NR$^{66}$SO$_2$ or NR$^{67}$ (wherein $R^{65}$, $R^{66}$ and $R^{67}$ each independently represents hydrogen, $C_{1-3}$alkyl or $C_{1-3}$alkoxy$C_{2-3}$alkyl));

2) NR$^{68}$R$^{69}$ (wherein $R^{68}$ and $R^{69}$ which may be the same or different are each hydrogen. $C_{1-3}$alkyl or $C_{1-3}$alkoxy$C_{2-3}$alkyl);

3) $X^{11}C_{1-5}$alkyl$X^5R^{24}$ (wherein $X^{11}$ is —O—, —S—, —SO$_2$—, NR$^{70}$CO, NR$^{71}$SO$_2$ or NR$^{72}$ (wherein $R^{70}$, $R^{71}$ and $R^{72}$ each independently represents hydrogen, $C_{1-3}$alkyl or $C_{1-3}$alkoxy$C_{2-3}$alkyl) and $X^5$ and $R^{24}$ are as defined hereinbefore); and 4) an aromatic heterocyclic group selected from pyrrolyl, imidazolyl pyrazolyl and triazolyl (which aromatic heterocyclic group is linked to the $C_{1-5}$alkyl moiety via a nitrogen atom of the heterocyclic ring and which aromatic heterocyclic group may carry up to 4 substituents selected from halogeno, $C_{1-4}$alkyl, $C_{1-4}$alkoxy, $C_{1-4}$hydroxyalkyl, $C_{1-4}$hydroxyalkoxy, carboxy, cyano, CONR$^{73}$R$^{74}$ and NR$^{75}$COR$^{76}$ (wherein $R^{73}$, $R^{74}$, $R^{75}$ and $R^{76}$, which may be the same or different, each represents hydrogen or $C_{1-4}$alkyl)), or a 5 or 6 membered saturated heterocyclic group with one or two heteroatoms, of which one is nitrogen and the other one may be selected independently from O, S and N, (which heterocyclic group is linked to the $C_{1-5}$alkyl moiety via a nitrogen atom of the heterocyclic group and which heterocyclic group may bear one or two substituents selected from halogeno, $C_{1-4}$alkyl, $C_{1-4}$hydroxyalkyl and $C_{1-4}$alkoxy)], may be prepared by reacting a compound of the formula X:

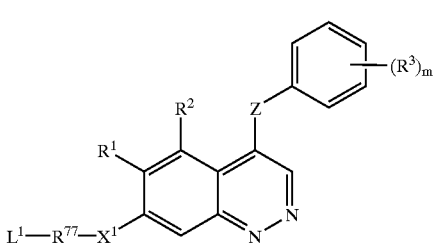

(X)

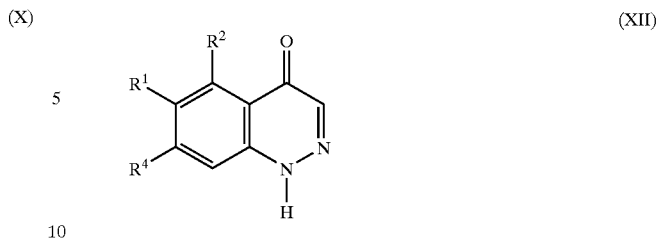

(XII)

(wherein $L^1$, $X^1$, $R^1$, $R^2$, $R^3$, Z and m are as hereinbefore defined and $R^{77}$ is $C_{1-5}$alkyl) with a compound of the formula XI:

 (XI)

(wherein $R^{64}$ is as defined hereinbefore) to give a compound of the formula I. The reaction may conveniently be effected in the presence of a base (as defined hereinbefore in process (a)) and advantageously in the presence of an inert solvent or diluent (as defined hereinbefore in process (a)), and at a temperature in the range, for example 0 to 150° C., conveniently at about 50° C.

(f) The production of those compounds of the formula I and salts thereof wherein the substituent $R^1$ is represented by $NR^6R^7$, where one or both of $R^6$ and $R^7$ are $C_{1-3}$alkyl, may be effected by the reaction of compounds of formula I wherein the substituent $R^1$ is an amino group and an alkylating agent, preferably in the presence of a base as defined hereinbefore. Such alkylating agents are $C_{1-3}$alkyl moieties bearing a displaceable moiety as defined hereinbefore such as $C_{1-3}$alkyl halides for example $C_{1-3}$alkyl chloride, bromide or iodide. The reaction is preferably effected in the presence of an inert solvent or diluent (as defined hereinbefore in process (a)) and at a temperature in the range, for example, 10 to 100° C. conveniently at about ambient temperature. This process can also be used for preparing compounds in which $R^5$—$X^1$ is an alkylamino or dialkylamino group.

(g) The production of compounds of formula I and salts thereof wherein one or more of the substituents $R^1$, $R^2$ or $R^3$ is an amino group or where $R^5$—$X^1$ is amino may be effected by the reduction of a corresponding compound of formula I wherein the substituent(s) at the corresponding position(s) of the cinnoline and/or phenyl ring is/are a nitro group(s). The reduction may conveniently be effected as described in process (i) hereinafter. The production of a compound of formula I and salts thereof wherein the substituent(s) at the corresponding position(s) of the cinnoline and/or phenyl ring is/are a nitro group(s) may be effected by the processes described hereinbefore and hereinafter in processes (a–e) and (i–v) using a cinnoline compound selected from the compounds of the formulae (I–XXVIII) in which the substituent(s) at the corresponding position(s) of the cinnoline and/or phenyl ring is/are a nitro group(s).

Synthesis of Intermediates (i) The compounds of formula III and salts thereof, constitute a further feature of the present invention. Such compounds in which $L^1$ is halogeno may for example be prepared by halogenating a compound of the formula XII:

(wherein $R^1$, $R^2$ and $R^4$ are as hereinbefore defined).

Convenient halogenating agents include inorganic acid halides, for example thionyl chloride, phosphorus(III) chloride, phosphorus(V)oxychloride and phosphorus(V) chloride. The halogenation reaction is conveniently effected in the presence of an inert solvent or diluent such as for example a halogenated solvent such as methylene chloride, trichloromethane or carbon tetrachloride, or an aromatic hydrocarbon solvent such as benzene or toluene. The reaction is conveniently effected at a temperature in the range, for example 10 to 150° C., preferably in the range 40 to 100° C.

The compounds of formula XII and salts thereof which constitute a further feature of the present invention may for example be prepared by reacting a compound of the formula XIII:

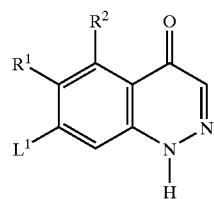

(XIII)

(wherein $R^1$, $R^2$ and $L^1$ are as hereinbefore defined) with a compound of the formula IX as hereinbefore defined. The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

The compounds of formula XII and salts thereof may also be prepared by cyclising a compound of the formula XIV:

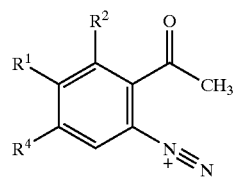

(XIV)

(wherein $R^1$, $R^2$ and $R^4$ are as hereinbefore defined) whereby to form a compound of formula XII or salt thereof. The cyclisation may be conveniently effected in the presence of a mineral or organic acid, for example sulphuric acid, hydrochloric acid or acetic acid or a mixture thereof, preferably at a temperature in the range 20° C. to 100° C., especially 50–80° C. or if desired under pH-controlled conditions, advantageously at a pH of 4.0 to 8.5. Preferably the pH of the solution is maintained within the range of 6.5 to 8.0. The desired pH is conveniently obtained by the use of an inert base or by the use of an aqueous solution of such a base. Bases which may be used include alkali metal bicarbonates, carbonates or hydroxides or organic amines such as for example pyridine or tertiary amines such as triethylamine, diisopropylethylamine, 2,6-lutidine, collidine, 4-dimethylaminopyridine or methylmorpholine, [for example as described in U.S. Pat. No. 4,620,000 (L. R. Denes) or DD 258809 (Hirsch et al.]

The compounds of formula XIV and salts thereof, which constitute a further feature of the present invention, may for example be prepared by diazotisation of a compound of the formula XV:

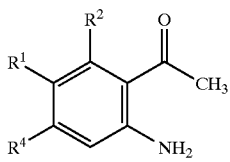

(XV)

(wherein $R^1$, $R^2$ and $R^4$ are as hereinbefore defined). The diazotisation is conveniently effected by the use of an alkali metal nitrite, such as sodium nitrite, in the presence of a mineral acid such as hydrochloric or sulphuric acid or in the presence of an organic acid such as acetic acid or in the presence of a mixture of such acids. The diazotisation is advantageously effected at a temperature in the range between the freezing point of the reaction mixture and 20° C., preferably from 0 to 20° C.

Preferably the compounds of formula XII are prepared by diazotisation and in situ cyclisation of the resulting compound of formula XIV for example as described by Borsch W. and Herbert A. Annalen der Chemie. Volume 546, p293–303.

Compounds of formula XV and salts thereof, which constitute a further feature of the present invention, may for example be prepared by reduction of the nitro group in a compound of formula XVI:

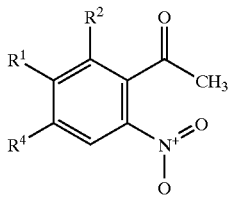

(XVI)

(wherein $R^1$, $R^2$ and $R^4$ are as hereinbefore defined) to yield a compound of formula XV as hereinbefore defined or salt thereof. The reduction of the nitro group may conveniently be effected by any of the procedures known for such a transformation. The reduction may be carried out, for example, by hydrogenation of a solution of the nitro compound in the presence of an inert solvent or diluent as defined hereinbefore preferably in the presence of a metal hydrogenation catalyst such as palladium or platinum. A further reducing agent is, for example, an activated metal such as activated iron (produced for example by washing iron powder with a dilute solution of an acid such as hydrochloric acid). Thus, for example, the reduction may be effected by heating a mixture of the nitro compound and the activated metal in the presence of a solvent or diluent such as a mixture of water and alcohol, for example methanol or ethanol, to a temperature in the range, for example, 50 to 150° C., conveniently at about 70° C.

Where the reduction is effected in the presence of activated irons this is advantageously produced in situ, conveniently by the use of iron, generally iron powder, in the presence of acetic acid/water and preferably at about 100° C.

The compounds of formula XVI and salts thereof which constitute a further feature of the present invention may for example be produced by reacting a compound of formula XVII:

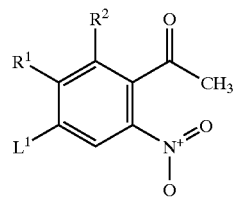

(XVII)

(wherein $R^1$, $R^2$ and $L^1$ are as hereinbefore defined) with a compound of formula IX as hereinbefore defined to yield a compound of formula XVI as hereinbefore defined or salt thereof. The reaction of the compounds of formula XVII and IX is conveniently effected under conditions as described for process (d) hereinbefore.

Compounds of formula XVII and salts thereof may for example be prepared by nitration of a compound of the formula XVIII:

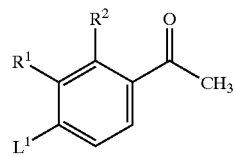

(XVIII)

(wherein $R^1$, $R^2$ and $L^1$ are as hereinbefore defined) whereby to form a compound of formula XVIII as hereinbefore defined or a salt thereof. The nitration is conveniently effected in the presence of nitric acid which may be dilute or concentrated, but is preferably about 70% nitric acid. The nitration is conveniently effected at a temperature in the range 0 to 20° C. The nitration may also be effected in the presence of a Lewis acid catalyst such as tin(IV)chloride. Where a Lewis acid catalyst is used the reaction is advantageously effected at a lower temperature, conveniently in the range −50 to 0° C., preferably at about −30° C., preferably in the presence of methylene chloride.

The compounds of formula XVI, as defined hereinbefore, and salts thereof may for example be prepared by nitration of compounds of the formula XVIII in which the $L^1$ moiety is replaced by $R^4$. The nitration is conveniently effected as described hereinbefore.

The compounds of formula XIII, as defined hereinbefore, and salts thereof may for example be prepared from compounds of the formulae XIV and XV, in which the $R^4$ group is replaced by the moiety $L^1$, the reactions may be effected by processes as described above for the preparation of compounds of formula XII from compounds of formulae XIV and XV. Compounds of the formula XV in which the $R^4$ group is replaced by the moiety $L^1$ may be prepared by the reduction of the nitro group in compounds of the formula XVII, the reduction may be effected as defined hereinbefore.

The compounds of formula III and salts thereof wherein $R^4$ represents $R^5$—$X^1$ may also be prepared for example by reacting a compound of the formula XIX:

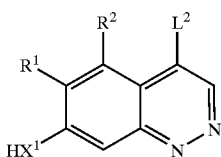

(XIX)

(wherein $R^1$, $R^2$ and $X^1$ are as hereinbefore defined and $L^2$ represents a displaceable protecting moiety) with a compound of the formula VII as hereinbefore defined whereby to obtain a compound of formula III in which $L^1$ is represented by $L^2$.

A compound of formula XIX is conveniently used in which $L^2$ represents a phenoxy group which may if desired carry up to 5 substituents, preferably up to 2 substituents, selected from halogeno, nitro and cyano. More preferably $L^2$ is chloro. The reaction may be conveniently effected under conditions as described for process (c) hereinbefore.

The compounds of formula XIX and salts thereof as hereinbefore defined may for example be prepared by deprotecting a compound of formula XX:

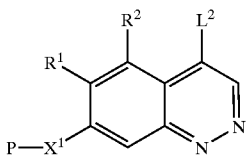

(XX)

(wherein $R^1$, $R^2$, P, $X^1$ and $L^2$ are as hereinbefore defined). Deprotection may be effected by techniques well known in the literature, for example where P represents a benzyl group deprotection may be effected by hydrogenolysis, or by treatment with trifluoroacetic acid.

One compound of formula III may if desired be converted into another compound of formula III in which the moiety $L^1$ is different. Thus for example a compound of formula III in which $L^1$ is other than halogeno, for example optionally substituted phenoxy, may be converted to a compound of formula III in which $L^1$ is halogeno by hydrolysis of a compound of formula III (in which $L^1$ is other than halogeno) to yield a compound of formula XII as hereinbefore defined, followed by introduction of halide to the compound of formula XII, thus obtained as hereinbefore defined, to yield a compound of formula III in which $L^1$ represents halogen.

(ii) The compounds of formula V and salts thereof, constitute a further feature of the present invention, and may for example be prepared by the reaction of a compound of formula III as hereinbefore defined with a compound of the formula XXI:

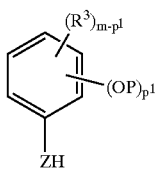

(XXI)

(wherein $R^3$, m, $p^1$, P and Z are as hereinbefore defined), whereby to form a compound of formula V as hereinbefore defined or a salt thereof. The reaction may for example be effected as described for process (a) hereinbefore.

The compounds of formula V and salts thereof wherein $R^4$ represents $R^5$—$X^1$ may also be prepared by reacting a compound of formula XXII:

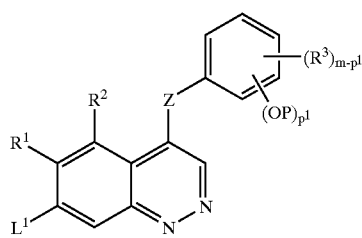

(XXII)

(wherein $R^1$, $R^2$, $L^1$, Z, $R^3$, m, $p^1$ and P are as hereinbefore defined) with a compound of formula IX as hereinbefore defined, whereby to form a compound of formula V as hereinbefore defined or a salt thereof. The reaction may for example be effected as described for process (d) above.

The compounds of formula V and salts thereof wherein $R^4$ represents $R^5$—$X^1$ may also be prepared by reacting a compound of formula XXIII:

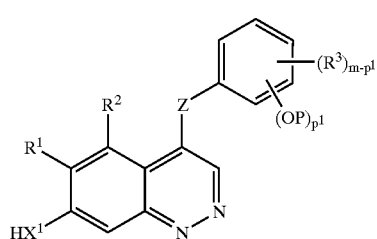

(XXIII)

(wherein $R^1$, $R^2$, $R^3$, $X^1$, Z, P, $p^1$ and m are as hereinbefore defined) with a compound of the formula VII as hereinbefore defined, whereby to form a compound of formula V as hereinbefore defined or a salt thereof. The reaction may for example be effected as described for process (c) hereinbefore.

The compounds of formula XXII and salts thereof, which constitute a further feature of the present invention, may for example be prepared by reaction of a compound of formula XXIV:

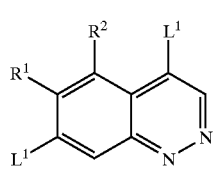

(XXIV)

(wherein $R^1$, $R^2$, and $L^1$ are as hereinbefore defined, and $L^1$ in the 4- and 7-positions may be the same or different) with a compound of the formula XXI as hereinbefore defined whereby to form a compound of formula XXII as hereinbefore defined or a salt thereof. The reaction may be effected for example by a process as described in (a) above.

Compounds of the formulae XX and XXIV may be prepared by any convenient known method, but may for example be prepared by introducing the moiety $L^2$ or $L^1$ as hereinbefore defined into a compound corresponding to a compound of formula XII but in which the group $R^4$ is replaced by the moiety P—$X^1$ or $L^1$. The reaction may be effected for example by a process as described for the preparation of compounds of formula III from compounds of formula XII as described in (i) above.

Compounds of the formula XXIII and salts thereof, which constitute a further feature of the present invention, may be made by deprotecting a compound of formula XXV:

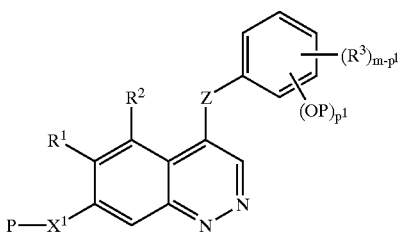

(XXV)

(wherein $R^1$, $R^2$, $R^3$, P, Z, $X^1$, $p^1$ and m are as hereinbefore defined) whereby to form a compound of formula XXIII or salt thereof. Deprotection of the compound of formula XXV may for example be effected as described in (i) above.

The compounds of formula XXV and salts thereof constitute a further feature of the present invention and may be prepared, for example, by reacting a compound of formula XX as hereinbefore defined with a compound of formula XXI as hereinbefore defined. The reaction may for example be effected as described in process (a).

Compounds of the formula V, as hereinbefore defined, and salts thereof wherein $R^4$ represents $R^5$—$X^1$ and $R^5$ is $C_{1-5}$alkyl$R^{64}$, wherein $R^{64}$ is as hereinbefore defined, may also be prepared by the reaction of a compound of formula XXVI:

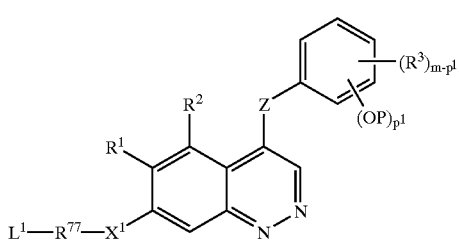

(XXVI)

(wherein $L^1$, $R^{77}$, $X^1$, $R^1$, $R^2$, $R^3$, Z, P, m and $p^1$ are as defined hereinbefore) with a compound of the formula XI as defined hereinbefore, under the conditions described in (e) above.

Compounds of the formula XXVI and salts thereof, which constitute a further feature of the present invention, may be made for example by reacting compounds of the formulae XXIII as defined hereinbefore, with a compound of the formula XXVII:

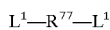

$L^1$—$R^{77}$—$L^1$ (XXVII)

(wherein $L^1$ and $R^{77}$ are as hereinbefore defined) under the conditions described in (c) above.

(iii) Compounds of the formula VI, as hereinbefore defined, and salts thereof constitute a further feature of the present invention and may be prepared by deprotecting the compound of formula XXVIII:

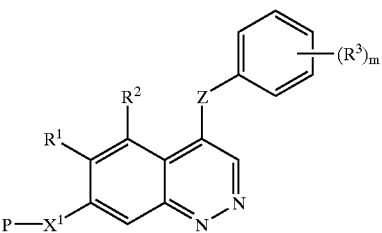

(XXVIII)

(wherein $R^1$, $R^2$, $R^3$, P, Z, $X^1$ and m are as hereinbefore defined) for example by a process as described in (i) above.

Compounds of the formula XXVIII and salts thereof, which constitute a further feature of the present invention, may for example be prepared by reacting compounds of the formulae XX and IV as hereinbefore defined, advantageously under the conditions described in (a) hereinbefore, to give a compound of the formula XXVIII as hereinbefore defined or salt thereof.

(iv) Compounds of the formula VIII as hereinbefore defined and salts thereof which constitute a further feature of the present invention may for example be prepared by reacting compounds of the formulae XXIV and IV as hereinbefore defined, the reaction may for example be effected by a process as described in (a) above.

(v) Compounds of the formula X as defined hereinbefore and salts thereof constitute a further feature of the present invention and may for example be made by reacting compounds of the formulae VI and XXVII as defined hereinbefore, the reaction may be effected for example by a process as described in (c) above.

Compounds of the formula X and salts thereof may also be made for example by deprotecting a compound of the formula XXVI, as hereinbefore defined, by a process for example as described in (b) above.

When a pharmaceutically acceptable salt of a compound of the formula I is required, it may be obtained, for example, by reaction of said compound with, for example, an acid using a conventional procedure, the acid having a pharmaceutically acceptable anion.

Many of the intermediates defined herein are novel, for example, those of the formulae III, V, VI, X, XII, XIV, XV, XVI, XXII, XXIII, XXV, XXVI and XXVIII and these are provided as a further feature of the invention.

The identification of compounds which potently inhibit the tyrosine kinase activity associated with the VEGF receptors such as Flt and/or KDR and which inhibit angiogenesis and/or increased vascular permeability is desirable and is the subject of the present invention. These properties may be assessed, for example, using one or more of the procedures set out below:

(a) In Vitro Receptor Tyrosine Kinase Inhibition Test

This assay determines the ability of a test compound to inhibit tyrosine kinase activity. DNA encoding VEGF or epidermal growth factor (EGF) receptor cytoplasmic domains may be obtained by total gene synthesis (Edwards M, International Biotechnology Lab 5(3), 19–25, 1987) or by cloning. These may then be expressed in a suitable expression system to obtain polypeptide with tyrosine kinase activity. For example VEGF and EGF receptor cytoplasmic domains, which were obtained by expression of recombinant protein in insect cells. were found to display intrinsic tyrosine kinase activity. In the case of the VEGF receptor Flt (Genbank accession number X51602), a 1.7 kb DNA fragment encoding most of the cytoplasmic domain, commencing with methionine 783 and including the termination codon, described by Shibuya et al (Oncogene, 1990, 5: 519–524), was isolated from cDNA and cloned into a baculovirus transplacement vector (for example pAcYM1 (see The Baculovirus Expression System: A Laboratory Guide, L. A. King and R. D. Possee, Chapman and Hall, 1992) or pAc360 or pBlueBacHis (available from Invitrogen Corporation)). This recombinant construct was co-transfected into insect cells (for example *Spodoptera frugiperda* 21 (Sf21)) with viral DNA (eg Pharmingen BaculoGold) to prepare recombinant baculovirus. (Details of the methods for the assembly of recombinant DNA molecules and the preparation and use of recombinant baculovirus can be found in standard texts for example Sambrook et al, 1989. Molecular cloning—A Laboratory Manual, 2nd edition, Cold Spring Harbour Laboratory Press and O'Reilly et al, 1992, Baculovirus Expression Vectors—A Laboratory Manual. W. H. Freeman and Co. New York). For other tyrosine kinases for use in assays, cytoplasmic fragments starting from methionine 806 (KDR, Genbank accession number L04947) and methionine 668 (EGF receptor, Genbank accession number X00588) may be cloned and expressed in a similar manner.

For expression of cFlt tyrosine kinase activity, Sf21 cells were infected with plaque-pure cFlt recombinant virus at a multiplicity of infection of 3 and harvested 48 hours later. Harvested cells were washed with ice cold phosphate buffered saline solution (PBS) (10 mM sodium phosphate pH7.4, 138 mM NaCl, 2.7 mM KCl) then resuspended in ice cold HNTG/PMSF (20 mM Hepes pH7.5, 150 mM NaCl, 10% v/v glycerol, 1% v/v Triton X100. 1.5 mM $MgCl_2$, 1 mM ethylene glycol-bis(βaminoethyl ether) N,N,N',N'-tetraacetic acid (EGTA), 1 mM PMSF (phenylmethylsulphonyl fluoride); the PMSF is added just before use from a freshly-prepared 100 mM solution in methanol) using 1 ml HNTG/PMSF per 10 million cells. The suspension was centrifuged for 10 minutes at 13.000 rpm at 4° C., the supernatant (enzyme stock) was removed and stored in aliquots at −70° C. Each new batch of stock enzyme was titrated in the assay by dilution with enzyme diluent (100 mM Hepes pH 7.4, 0.2 mM $Na_3VO_4$, 0.1% v/v Triton X100, 0.2 mM dithiothreitol). For a typical batch, stock enzyme is diluted 1 in 2000 with enzyme diluent and 50 μl of dilute enzyme is used for each assay well.

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 μl of diluted substrate solution was dispensed into all wells of assay plates (Nunc maxisorp 96-well immunoplates) which were sealed and left overnight at 4° C.

On the day of the assay the substrate solution was discarded and the assay plate wells were washed once with PBST (PBS containing 0.05% v/v Tween 20) and once with 50 mM Hepes pH7.4.

Test compounds were diluted with 10% dimethylsulphoxide (DMSO) and 25 μl of diluted compound was transferred to wells in the washed assay plates. "Total" control wells contained 10% DMSO instead of compound. Twenty five microliters of 40 mM $MnCl_2$ containing 8 μM adenosine-5'-triphosphate (ATP) was added to all test wells except "blank" control wells which contained $MnCl_2$ without ATP. To start the reactions 50 μl of freshly diluted enzyme was added to each well and the plates were incubated at room temperature for 20 minutes. The liquid was then discarded and the wells were washed twice with PBST. One hundred microliters of mouse IgG anti-phosphotyrosine antibody (Upstate Biotechnology Inc. product 05-321), diluted 1 in 6000 with PBST containing 0.5% w/v bovine serum albumin (BSA), was added to each well and the plates were incubated for 1 hour at room temperature before discarding the liquid and washing the wells twice with PBST. One hundred microliters of horse radish peroxidase (HRP)-linked sheep anti-mouse Ig antibody (Amersham product NXA 931), diluted 1 in 500 with PBST containing 0.5% w/v BSA, was added and the plates were incubated for 1 hour at room temperature before discarding the liquid and washing the wells twice with PBST. One hundred microliters of 2,2'-azino-bis(3-ethylbenzthiazoline-6-sulphonic acid) (ABTS) solution, freshly prepared using one 50 mg ABTS tablet (Boehringer 1204 521) in 50 ml freshly prepared 50 mM phosphate-citrate buffer pH5.0+0.03% sodium perborate (made with 1 phosphate citrate buffer with sodium perborate (PCSB) capsule (Sigma P4922) per 100 ml distilled water), was added to each well. Plates were then incubated for 20–60 minutes at room temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibtion of enzyme activity.

(b) In Vitro HUVEC Proliferation Assay

This assay determines the ability of a test compound to inhibit the growth factor-stimulated proliferation of human umbilical vein endothelial cells (HUVEC).

HUVEC cells were isolated in MCDB 131 (Gibco BRL)+ 7.5% v/v foetal calf serum (FCS) and were plated out (at passage 2 to 8), in MCDB 131+2% v/v FCS+3 μg/ml heparin+1 μg/ml hydrocortisone, at a concentration of 1000 cells/well in 96 well plates. After a minimum of 4 hours they were dosed with the appropriate growth factor (i.e. VEGF 3 ng/ml, EGF 3 ng/ml or b-FGF 0.3 ng/ml) and compound. The cultures were then incubated for 4 days at 37° C. with 7.5% $CO_2$. On day 4 the cultures were pulsed with 1 μCi/well of tritiated-thymidine (Amersham product TRA 61) and incubated for 4 hours. The cells were harvested using a 96-well plate harvester (Tomtek) and then assayed for incorporation of tritium with a Beta plate counter. Incorporation of radioactivity into cells, expressed as cpm, was used to measure inhibition of growth factor-stimulated cell proliferation by compounds.

(c) In Vivo Rat Uterine Oedema Assay

This test measures the capacity of compounds to reduce the acute increase in uterine weight in rats which occurs in the first 4–6 hours following oestrogen stimulation. This early increase in uterine weight has long been known to be due to oedema caused by increased permeability of the uterine vasculature and recently Cullinan-Bove and Koos (Endocrinology, 1993,133:829–837) demonstrated a close temporal relationship with increased expression of VEGF mRNA in the uterus. We have found that prior treatment of the rats with a neutralising monoclonal antibody to VEGF significantly reduces the acute increase in uterine weight confirming that the increase in weight is substantially mediated by VEGF.

Groups of 20 to 22-day old rats were treated with a single subcutaneous dose of oestradiol benzoate (2.5 μg/rat) in a solvent, or solvent only. The latter served as unstimulated controls. Test compounds were orally administered at various times prior to the administration of oestradiol benzoate. Five hours after the administration of oestradiol benzoate the rats were humanely sacrificed and their uteri were dissected, blotted and weighed. The increase in uterine weight in groups treated with test compound and oestradiol benzoate and with oestradiol benzoate alone was compared using a Student T test. Inhibition of the effect of oestradiol benzoate was considered significant when p<0.05.

According to a further aspect of the invention there is provided a pharmaceutical composition which comprises a compound of the formula I as defined hereinbefore or a pharmaceutically acceptable salt thereof, in association with a pharmaceutically acceptable excipient or carrier.

The composition may be in a form suitable for oral administration, for example as a tablet or capsule, for parenteral injection (including intravenous, subcutaneous, intramuscular intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5–5000 mg per square meter body area of the animal, i.e. approximately 0.1–100 mg/kg. A unit dose in the range, for example, 1–100 mg/kg, preferably 1–50 mg/kg is envisaged and this normally provides a therapeutically-effective dose. A unit dose form such as a tablet or capsule will usually contain, for example 1–250 mg of active ingredient.

According to a further aspect of the present invention there is provided a compound of the formula I or a pharmaceutically acceptable salt thereof as defined hereinbefore for use in a method of treatment of the human or animal body by therapy.

We have found that compounds of the present invention inhibit VEGF receptor tyrosine kinase activity and are therefore of interest for their antiangiogenic effects and/or their ability to cause a reduction in vascular permeability.

Thus according to a further aspect of the invention there is provided the use of a compound of the formula I, or a pharmaceutically acceptable salt thereof in the manufacture of a medicament for use in the production of an antiangiogenic and/or vascular permeability reducing effect in a warm-blooded animal such as a human being.

According to a further feature of the invention there is provided a method for producing an antiangiogenic and/or vascular permeability reducing effect in a warm-blooded animal, such as a human being, in need of such treatment which comprises administering to said animal an effective amount of a compound of formula I or a pharmaceutically acceptable salt thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

The antiangiogenic and/or vascular permeability reducing treatment defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic and/or vascular permeability reducing treatment defined hereinbefore may be: surgery, radiotherapy or chemotherapy. Such chemotherapy may cover three main categories of therapeutic agent:

(i) other antiangiogenic agents that work by different mechanisms from those defined hereinbefore (for example linomide, inhibitors of integrin αvβ3 function, angiostatin, razoxin, thalidomide);

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan).

As stated above the compounds defined in the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, acute and chronic nephropathies, atheroma, arterial restenosis, autoimmune diseases, acute inflammation and ocular diseases with retinal vessel proliferation. In particular such compounds of the invention are expected to slow advantageously the growth of primary and recurrent solid tumours of, for example, the colon, breast, prostate, lungs and skin. More particularly such compounds of the invention are expected to inhibit the growth of those primary and recurrent solid tumours which are associated with VEGF, especially those tumours which are significantly dependent on VEGF for their growth and spread, including for example, certain tumours of the colon, breast, prostate, lung, vulva and skin.

In addition to their use in therapeutic medicine, the compounds of formula I and their pharmaceutically acceptable salts are also useful as pharmacological tools in the development and standardisation of in vitro and in vivo test systems for the evaluation of the effects of inhibitors of VEGF receptor tyrosine kinase activity in laboratory animals such as cats, dogs, rabbits, monkeys, rats and mice, as part of the search for new therapeutic agents.

It is to be understood that where the term "ether" is used anywhere in this specification it refers to diethyl ether.

The invention will now be illustrated in the following non-limiting Examples in which, unless otherwise stated:

[(i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon;

(iii) column chromatography (by the flash procedure) and medium pressure liquid chromatography (MPLC) were performed on Merck Kieselgel silica (Art, 9385) or Merck Lichroprep RP-18 (Art, 9303) reversed-phase silica obtained from E. Merck, Darmstadt, Germany;

(iv) yields are given for illustration only and are not necessarily the maximum attainable;

(v) melting points are uncorrected and were determined using a Mettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet;

(vii) intermediates were not generally fully characterised and purity was assessed by thin layer chromatography (TLC), high-performance liquid chromatography (HPLC), infra-red (IR) or NMR analysis;

(viii) petroleum ether refers to that fraction boiling between 40–60° C.

(ix) the following abbreviations have been used:

| DMF | N,N-dimethylformamide |
|---|---|
| DMSO | dimethylsulphoxide |
| TFA | trifluoroacetic acid.] |

EXAMPLE 1

A solution of 4-chloro-6,7-dimethoxycinnnoline hydrochloride (0.6 g, 2.3 mmol), 3-hydroxy-4-methylaniline (0.425 g, 2.5 mmol) and triethylamine (800 μl, 6 mmol) in DMF (10 ml) was refluxed for 1 hour. The solution was cooled and poured directly onto a Diaion (trade mark of Mitsubishi) HP20SS column and elution was performed with acetonitrile/water (4/6) to give, after evaporation of the solvent, 4-(3-hydroxy-4-methylanilino)-6,7-dimethoxycinnoline (220 mg, 31%) as a cream solid.

m.p. 240–244° C.; $^1$H NMR Spectrum: (DMSOd$_6$) 2.15 (s, 3H); 3.97 (s, 3H); 3.99 (s, 3H); 6.73 (d, 1H); 6.85 (s, 1H); 7.14 (d, 1H); 7.52 (s, 1H); 7.69 (s, 1H); 8.73 (s, 1H); 8.81 (s, 1H); 9.6 (s, 1H); MS–ESI: 312 [MH]$^+$; Elemental analysis: Found C, 62.2; H, 5.8; N, 13.1; $C_{17}H_{17}N_3O_3$ 0.9H$_2$O Requires C, 62.3; H, 5.8; N, 12.8%.

The starting material, 4-chloro-6,7-dimethoxycinnoline hydrochloride was obtained by heating a solution of 4-hydroxy-6,7-dimethoxycinnoline (1 g, 4.8 mmol) in thionyl chloride (20 ml) containing DMF (2drops) at reflux for 3 hours. After cooling and evaporating the excess thionyl chloride, the solid was triturated with ether and filtered to give 4-chloro-6,7-dimethoxycinnoline hydrochloride (1.2 g, quantitative).

The starting material, 4-hydroxy-6,7-dimethoxycinnoline was obtained by adding a solution of sodium nitrite (1.9 g, 27 mmol) to a solution of 2-amino-4,5-dimethoxyacetophenone (5 g, 0.025 mol) in acetic acid (90 ml) and sulphuric acid (15 ml) at a rate to maintain the temperature below 20° C. The mixture was heated at 80° C. for 90 minutes. After cooling and concentrating the solution to half its original volume, the residue was poured into ether (800 ml). The solid was collected by filtration and suspended in water (200 ml). After adjusting to pH7 with sodium hydroxide the solid was filtered, washed with water, methanol and methylene chloride to give 4-hydroxy-6,7-dimethoxycinnoline (4.5 g, 87%).

EXAMPLE 2

A solution of 4-chloro-6-methoxy-7-(2-methoxyethoxy) cinnoline (0.4 g, 1.5 mmol) and 3-hydroxy-4-methylaniline (0.2 g, 1.6 mmol) in DMF (5 ml) was heated at 150° C. for 20 minutes. After cooling, isopropanol (15 ml) was added and the resulting solid filtered off, washed with isopropanol and dried under vacuum to give 4-(3-hydroxy-4-methylanilino)-6-methoxy-7-(2-methoxyethoxy)cinnoline as the hydrochloride salt (yellow solid, 537 mg 91%).

$^1$H NMR Spectrum: (DMSOd$_6$; CF$_3$COOD) 2.38 (s, 3H), 3.55 (s, 3H); 3.95 (t, 2H); 4.2 (s, 3H); 4.5 (t, 2H); 7.05 (d, 1H); 7.1 (s, 1H); 7.4 (d, 1H); 7.52 (s, 1H); 8.2 (s, 1 H); 8.55 (d, 1H); MS–ESI: 356 [MH]$^+$; Elemental analysis: Found C, 58.4; H, 5.9; N, 10.9; $C_{19}H_{21}N_3O_4$ 1HCl Requires C, 58.2; H, 5.7; N, 10.7%.

The starting material 4-chloro-6-methoxy-7-(2-methoxyethoxy)cinnoline was obtained by heating a solution of 4-hydroxy-6-methoxy-7-(2-methoxyethoxy) cinnoline (7.8 g, 0.031 mol) in thionyl chloride (130 ml) containing DMF (0.8 ml) at 80° C. for 2 hours. After dilution with toluene, the mixture was evaporated to dryness. The resulting solid was filtered off, washed with ether, and then dissolved in ethyl acetate. The ethyl acetate solution was washed with saturated aqueous sodium hydrogen carbonate solution and then brine, dried (MgSO$_4$) and the solvent evaporated. The residue was purified by flash chromatography using methylene chloride/ethyl acetate (1/9) as eluent to give 4-chloro-6-methoxy-7-(2-methoxyethoxy)cinnoline (6.2 g, 74%).

m.p. 171–173° C.

The starting material 4-hydroxy-6-methoxy-7-(2-methoxyethoxy)cinnoline was obtained by adding a solution of sodium nitrite (3.9 g, 0.056 mol) in water (5 ml), dropwise, to a solution of 2-amino-4-(2-methoxyethoxy)-5-methoxyacetophenone (12.18 g, 0.05 mol) in acetic acid (180 ml) and sulphuric acid (30 ml). After stirring for 90 minutes at 80° C. the solution was concentrated to half its original volume and poured into ether (800 ml). The solid was collected by filtration and suspended in water (400 ml). After adjusting to pH7.6 with 2M aqueous sodium hydroxide solution the resulting solid was filtered off and washed with ether to give 4-hydroxy-6-methoxy-7-(2-methoxyethoxy)cinnoline (8 g, 62%).

m.p. 232–234° C.

The starting material, 2-amino-4-(2-methoxyethoxy)-5-methoxyacetophenone was obtained by adding iron powder (10 g, 0.18 mol), in portions, to a solution of 2-nitro-4-(2-methoxyethoxy)-5-methoxyacetophenone (17.3 g, 0.064 mol) in acetic acid (80 ml) heated at 100° C. After stirring for 30 minutes at 100° C., the mixture was cooled and water (20 ml) was added. The mixture was extracted with ethyl acetate, the combined extracts were washed with water, saturated sodium carbonate solution and brine and then dried (MgSO$_4$) and the solvent evaporated. The residue was purified by flash chromatography using methylene chloride/ethyl acetate (8/2 followed by 75/25) as eluent to give 2-amino-4-(2-methoxyethoxy)-5-methoxy-acetophenone (12.52 g, 81%).

m.p. 99–101° C.

The starting material, 2-nitro-4-(2-methoxyethoxy)-5-methoxyacetophenone, was obtained by adding 3-methoxy-4-(2-methoxyethoxy)acetophenone (18.1 g, 0.08 mol) in portions over 50 minutes to a solution of 69.5% nitric acid (163 ml) cooled to 2° C. After stirring for 2 hours at ambient temperature, the reaction mixture was poured onto ice and extracted with ethyl acetate. The organic layer was washed with water and brine, dried (MgSO$_4$) and the solvent evaporated. The residue was purified by flash chromatography using methylene chloride/ethyl acetate (95/5) as eluent to give 2-nitro-4-(2-methoxyethoxy)-5-methoxyacetophenone (17.4 g, 80%) as a pale yellow solid.

m.p. 120–124° C.

The starting material, 3-methoxy-4-(2-methoxyethoxy) acetophenone, was obtained by heating a solution of 4-hydroxy-3-methoxyacetophenone (20 g, 0.12 mol) and, bromomethyl methyl ether (12.4 ml, 0.13 mol) in DMF (400 ml) containing potassium carbonate (49.8 g, 0.36 mol) at 50° C. overnight. After cooling, the reaction mixture was diluted with water and adjusted to pH2. After extraction with ethyl acetate, the organic layer was washed with brine, dried (MgSO$_4$) and evaporated. The residue was purified by flash chromatography using petroleum ether/ethyl acetate (6/4 followed by 1/1) as eluent to give 3-methoxy-4-(2-methoxyethoxy)acetophenone (21.8 g, 81%).

m.p. 84–86° C.

EXAMPLE 3

A solution of 4-chloro-6-methoxy-7-(2-methoxyethoxy) cinnoline (0.4 g, 1.5 mmol), (prepared as described for the starting material in Example 2), and 4-chloro-2-fluoroaniline (282 μl, 2.5 mmol) in DMF (5 ml) was treated as described in Example 2, to give 4-(4-chloro-2-fluoroanilino)-6-methoxy-7-(2-methoxyethoxy)cinnoline as the hydrochloride salt (450 mg, 72%).

m.p. 279–281° C.; $^1$H NMR Spectrum: (DMSOd$_6$; CF$_3$COOD) 3.35 (s, 3H); 3.8 (t, 2H); 4.05 (s, 3H); 4.4 (t, 2H); 7.4 (s, 1H); 7.5 (d, 1H); 7.7 (t, 1H); 7.75 (d, 1H); 8.05 (s, 1H); 8.3 (s, 1H); MS–ESI: 378 [MH]$^+$;

| Elemental analysis: | Found | C 52.1 | H 4.5 | N 10.2 |
|---|---|---|---|---|
| C$_{18}$H$_{17}$N$_3$O$_3$ClF 1 HCl | Requires | C 52.2 | H 4.4 | N 10.1% |

EXAMPLE 4

4-Chloro-6-methoxy-7-(2-methoxyethoxy)cinnoline (0.3 g, 1.1 mmol), (prepared as described for the starting material in Example 2), was added to a solution of 2,4-dihydroxytoluene (1 g, 8 mmol) and potassium hydroxide (72 mg, 1.3 mmol) heated at 150° C. After stirring for 10 minutes at 150° C., the mixture was allowed to cool and then partitioned between ethyl acetate and water. The pH was adjusted to 6 and the organic layer was washed with water and brine and dried (MgSO$_4$) and evaporated. The solid was filtered off, washed with ether and dried under vacuum to give a 1/1 mixture of 4-(3-hydroxy-4-methylphenoxy)-6-methoxy-7-(2-methoxyethoxy)cinnoline and 4-(3-hydroxy-2-methylphenoxy)-6-methoxy-7-(2-methoxyethoxy) cinnoline (150 mg, 38%).

$^1$H NMR Spectrum: (DMSOd$_6$; CD$_3$COOD) 2.05 and 2.1 (s×2, 3H); 3.35 (s, 3H); 3.8 (t, 2H); 4.1 and 4.15 (s×2, 3H); 4.45 (t, 2H); 6.75 (m, 1H); 6.85 (m, 1H); 7.25 (d, 1H); 8.25 (d, 1H); 7.7–7.8 (m, 2H); 8.52 and 8.65 (s×2, 1H); MS–ESI: 357 [MH]$^+$ 379 [MNa]$^+$;

| Elemental analysis: | Found | C 64.2 | H 5.9 | N 7.7 |
|---|---|---|---|---|
| C$_{19}$H$_{20}$N$_2$O$_5$ | Requires | C 64.0 | H 5.7 | N 7.9% |

The starting material 2,4-dihydroxytoluene was prepared by adding boron tribromide (3.1 ml, 3.2 mmol) to a solution of 2,4-dimethoxytoluene (1 g, 6.5 mmol) in pentane (10 ml) at −70° C. The reaction mixture was allowed to warm to ambient temperature and the mixture stirred for a further 2 hours. Ice water and ethyl acetate were then added and the aqueous layer basified to pH9.5 with 2M aqueous sodium hydroxide solution. After stirring for 10 minutes, the organic layer was separated and the aqueous layer extracted with ethyl acetate. The combined organic extract was washed with brine, dried (MgSO$_4$) and the solvent removed by evaporation. The residue was purified by flash chromatography eluting with methylene chloride/ethyl acetate (9/1) to give 2,4-dihydroxytoluene (759 mg, 94%) as a white solid.

EXAMPLE 5

A solution of 4-chloro-6-methoxy-7-(2-methoxyethoxy) cinnoline (0.2 g, 0.74 mmol), (prepared as described for the starting material in Example 2), and 4-bromo-2-fluoroaniline (155 mg, 0.82 mmol) in DMF (2.5 ml) was heated at 150° C. for 45 minutes. After cooling to ambient temperature the mixture was treated as described in Example 3 to give 4-(4-bromo-2-fluoroanilino)-6-methoxy-7-(2-methoxyethoxy)cinnoline as the hydrochloride salt (150 mg, 44%).

m.p. 278–281° C.; $^1$H NMR Spectrum: (DMSOd$_6$; CF$_3$COOD) 3.38 (s, 3H); 3.85 (t, 2H); 4.1 (s, 3H); 4.4 (t, 2H); 7.45 (s, 1H); 7.65 (dd, 1H); 7.65 (s, 1H); 7.9 (d, 1H); 8.1 (s, 1H); 8.35 (s, 1H); MS–ESI: 422 [MH]$^+$;

| Elemental analysis: | Found | C 47.3 | H 4.1 | N 8.9 |
|---|---|---|---|---|
| C$_{18}$H$_{17}$N$_3$O$_3$BrF 1 HCl | Requires | C 47.1 | H 4.0 | N 9.2% |

EXAMPLE 6

A solution of 7-benzyloxy-4-chloro-6-methoxycinnoline hydrochloride (3.4 g, 10 mmol) and 4-chloro-2-fluoro-5-hydroxyaniline, (prepared as described in EP 061741 A2), (1.84 g, 11 mmol) in DMF (42 ml) was heated at 130° C. for 20 minutes. The resulting solid was filtered off, washed with isopropanol, ether and dried under vacuum to give 7-benzyloxy-4-(4-chloro-2-fluoro-5-hydroxyanilino)-6-methoxycinnoline as the hydrochloride salt (yellow solid, 3.5 g, 75%).

m.p. 280–284° C.; $^1$H NMR Spectrum: (DMSOd$_6$) 4.05 (s, 3H); 5.4 (s, 2H); 7.2 (d, 1H); 7.4–7.5 (m, 3H); 7.5–7.55 (m, 3H); 7.68 (d, 1H); 8.2 (s, 1H); 8.35 (s, 1H); MS–ESI: 426 [MH]$^+$;

| Elemental analysis: | Found | C 57.4 | H 4.2 | N 9.5 |
|---|---|---|---|---|
| C$_{22}$H$_{17}$N$_3$O$_3$ClF 1 HCl | Requires | C 57.2 | H 3.9 | N 9.1% |

The starting material, 7-benzyloxy-4-chloro-6-methoxycinnoline hydrochloride, was obtained by heating a solution of 7-benzyloxy-4-hydroxy-6-methoxycinnoline (11 g, 39 mmol) in thionyl chloride (180 ml) containing DMF (1 ml) at reflux for 1 hour. After cooling, excess thionyl chloride was removed by evaporation and azeotroped with toluene. The residue was triturated with ether, filtered off, washed with ether and dried under vacuum to give 7-benzyloxy-4-chloro-6-methoxycinnoline hydrochloride as a cream solid (13.6 g, quantitative).

The starting material 7-benzyloxy-4-hydroxy-6-methoxycinnoline was obtained by dropwise addition of a solution of sodium nitrite (4.9 g, 0.072 mol) in water (10 ml) to a solution of 2-amino-4-benzyloxy-5-methoxyacetophenone (16.3 g 0.06 mol) in acetic acid (250 ml) and 70% sulphuric acid (7.3 ml). After stirring for 30 minutes, triethylamine (25 ml) was added and stirring was continued for 6 hours. After adjusting to pH3.2 with 2M aqueous sodium hydroxide solution, the solid was filtered off, washed with water, ether and dried under vacuum to give 7-benzyloxy-4-hydroxy-6-methoxycinnoline (12.76 g, 75%) as a brown solid.

m.p. 262–264° C.

The starting material 2-amino-4-benzyloxy-5-methoxyacetophenone was obtained by adding powdered iron (520 mg, 9.3 mmol) to a solution of 2-nitro-4-benzyloxy-5-methoxyacetophenone (1 g, 3.3 mmol) in acetic acid (5 ml) heated at 100° C. After 30 minutes. the reaction mixture was cooled to ambient temperature and diluted with water. After extraction with ethyl acetate the organic layer was washed with water, brine, dried (MgSO$_4$) and the solvent evaporated. The residue was purified by flash chromatography using petroleum ether/ethyl acetate (3/1) as eluent to give 2-amino-4-benzyloxy-5-methoxyacetophenone (629 mg, 70%) as a yellow solid.

m.p. 139–141° C.

The starting material 2-nitro-4-benzyloxy-5-methoxyacetophenone was obtained by, addition of a suspension of tin(IV)chloride (15.8 ml, 0.13 mol) and 69.5% nitric acid (9.1 ml, 0.2 mol) in methylene chloride (110 ml), dropwise over a period of 20 minutes, to a solution of 4-benzyloxy-3-methoxyacetophenone (28.9 g, 0.11 mol) in methylene chloride (400 ml) cooled at −35° C.

After stirring for 20 minutes at −25° C., the mixture was warmed to ambient temperature and poured onto ice/water (1 liter). After extraction with methylene chloride the organic layer was washed with brine, dried (MgSO$_4$) and the solvent evaporated. The residue was purified by flash chromatography using petroleum ether/ethyl acetate (7/3) as eluent to give 2-nitro-4-benzyloxy-5-methoxyacetophenone (27 g, 76%) as a yellow solid.

m.p. 134–136° C.

The starting material, 4-benzyloxy-3-methoxyacetophenone, was obtained by heating a solution of 4-hydroxy-3-methoxyacetophenone (20 g, 0.12 mol), benzyl bromide (15.7 ml, 0.13 mol) and potassium carbonate (49.8 g, 0.36 mol) in DMF (400 ml) at 40° C. overnight. After cooling, the mixture was diluted with water, acidified to approximately pH3 and extracted with ethyl acetate. The organic layer was washed with brine, dried (MgSO$_4$) and the solvent evaporated. The residue was purified by flash chromatography using petroleum ether/ethyl acetate (8/2 followed by 65/35) as eluent to give 4-benzyloxy-3-methoxyacetophenone (30.3 g, 99%).

m.p. 86–88° C.

EXAMPLE 7

Acetic anhydride (920 μl, 9.7 mmol) and 4-dimethylaminopyridine (80 mg, 0.65 mmol) were added to a suspension of 7-benzyloxy-4-(4-chloro-2-fluoro-5-hydroxyanilino)-6-methoxycinnoline (3 g, 6.5 mmol), (prepared as described in Example 6), in pyridine (50 ml). After heating at 110° C. for 25 minutes, the solid was filtered off, washed with water and ether and dried under vacuum. The solid was suspended in 2M ethereal hydrogen chloride and the volatiles removed by evaporation to give 4-(5-acetoxy-4-chloro-2-fluoroanilino)-7-benzyloxy-6-methoxycinnoline as the hydrochloride salt (yellow solid. 3.1 g, 94%).

m.p. 240–247° C.; $^1$H NMR Spectrum: (DMSOd$_6$) 2.35 (s, 3H); 4.05 (s, 3H); 5.4 (s, 2H); 7.35–7.5 (m, 3H); 7.55 (s, 1H); 7.55 (d, 1H); 7.6 (s, 1H); 7.7 (d, 1H); 7.95 (d, 1H); 8.25 (s, 1H); 8.4 (s, 1H); MS–ESI: 468 [MH]$^+$;

| Elemental analysis: | Found | C 56.8 | H 4.2 | N 8.2 |
|---|---|---|---|---|
| C$_{24}$H$_{19}$N$_3$O$_4$ClF 1 HCl | Requires | C 57.2 | H 4.0 | N 8.3% |

EXAMPLE 8

A solution of 4-chloro-6-methoxy-7-(2-methoxyethoxy)cinnoline (0.1 g, 0.74 mmol), (prepared as described for the starting material in Example 2), and 4-chloro-2-fluoro-5-hydroxyaniline (432 mg, 0.82 mmol), (prepared as described in EP 061741 A2), in DMF (2.5 ml) was heated at 140° C. for 45 minutes. The work up procedure was as described in Example 6 and gave 4-(4-chloro-2-fluoro-5-hydroxyanilino)-6-methoxy-7-(2-methoxyethoxy)cinnoline as the hydrochloride salt (yellow solid, 157 mg, 49%).

m.p. 296–299° C.; $^1$H NMR Spectrum: (DMSOd$_6$; CF$_3$COOD) 3.4 (s, 3H); 3.85 (t, 2H); 4.1 (s, 3H); 4.4 (t, 2H); 7.2 (d, 1H); 7.45 (s, 1H); 7.65 (d, 1H); 8.05 (s, 1H); 8.35 (d, 1H); MS–ESI: 394 [MH]$^+$;

| Elemental analysis: | Found | C 50.1 | H 4.4 | N 9.8 |
|---|---|---|---|---|
| C$_{18}$H$_{17}$N$_3$O$_4$ClF 1 HCl | Requires | C 50.3 | H 4.2 | N 9.8% |

EXAMPLE 9

A solution of 4-chloro-6-methoxy-7-(2-methoxyethoxy)cinnoline (0.1 g, 0.37 mmol), (prepared as described for the starting material in Example 2), and 4-bromo-2-fluoro-5-hydroxyaniline (84 mg, 0.4 mmol), (prepared as described in EP 061741 A2), in DMF (2 ml) was heated at 140° C. for 1 hour. The work up procedure was as described in Example 6 for the production of the final compound and gave in this example 4-(4-bromo-2-fluoro-5-hydroxyanihno)-6-methoxy-7-(2-methoxyethoxy)cinnoline as the hydrochloride salt (yellow solid, 127 mg, 72%).

m.p. 288–289° C.; $^1$H NMR Spectrum: (DMSOd$_6$; CF$_3$COOD) 3.4 (s, 3H); 3.85 (t, 2H); 4.1 (s, 3H); 4.4 (t, 2H); 7.2 (d, 1H); 7.45 (s, 1H); 7.75 (d, 1H); 8.1 (s, 1H); 8.35 (s, 1H); MS–ESI: 438 [MH]$^+$;

| Elemental analysis: | Found | C 45.8 | H 4.0 | N 8.9 |
|---|---|---|---|---|
| C$_{18}$H$_{17}$N$_3$O$_4$BrF 1 HCl | Requires | C 45.5 | H 3.8 | N 8.9% |

EXAMPLE 10

A suspension of 4-chloro-6-methoxy-7-(4-pyridylmethoxy)cinnoline hydrochloride (0.17 g, 0.45 mmol) and 4-chloro-2-fluoro-5-hydroxyaniline (102 mg, 0.63 mmol), (prepared as described in EP 061741 A2), in 2-pentanol (3.5 ml) was heated at reflux overnight. After cooling, isopropanol was added. The solid formed was filtered off, washed with isopropanol, ether and dried under vacuum to give 4-(4-chloro-2-fluoro-5-hydroxyanilino)-6-methoxy-7-(4-pyridylmethoxy)cinnoline as the hydrochloride salt (yellow solid, 194 mg, 86%).

m.p. 243–251° C.; $^1$H NMR Spectrum: (DMSOd$_6$) 4.12 (s, 3H); 5.7 (s, 2H); 7.25 (d, 1H); 7.55 (s, 1H); 7.7 (d, 1H); 7.9 (d, 2H); 8.3 (s, 1H); 8.4 (s, 1H); 8.9 (d, 2H); 10.85 (br s, 1H); 11.55 (br s, 1H); MS–ESI: 427 [MH]$^+$;

| Elemental analysis: | Found | C 49.6 | H 3.9 | N 10.8 |
|---|---|---|---|---|
| C$_{21}$H$_{16}$N$_4$O$_3$ClF 1.3 H$_2$O 1.65 HCl | Requires | C 49.4 | H 4.0 | N 11.0% |

The starting material, 4-chloro-6-methoxy-7-(4-pyridylmethoxy)cinnoline hydrochloride, was obtained by adding 4-chloro-7-hydroxy-6-methoxycinnoline (200 mg, 0.95 mmol), followed by 4-hydroxymethylpyridine (108 mg, 1 mmol) and 1,1'-(azodicarbonyl)dipiperidine (647 mg, 2.5 mmol), in portions, to a solution of tri(n-butyl)phosphine (640 µl, 2.5 mmol) in methylene chloride (6 ml). After stirring for 1 hour at ambient temperature, a solution of 7M hydrogen chloride in isopropanol (300 µl, 2.1 mmol) was added. The resulting solid was filtered off, washed with methylene chloride and ether to give 4-chloro-6-methoxy-7-(4-pyridylmethoxy)cinnoline hydrochloride as a solid (196 mg, 55%).

The starting material, 4-chloro-7-hydroxy-6-methoxycinnoline was obtained by heating a solution of 7-benzyloxy-4-chloro-6-methoxycinnoline hydrochloride (3.06 g, 9 mmol), (prepared as described for the starting material in Example 6), in TFA (30 ml) at reflux for 5 hours. After evaporation of the solvent, the residue was suspended in water and adjusted to pH7 with saturated aqueous sodium hydrogen carbonate solution. The resulting solid was filtered off, washed with water and ether and dried under vacuum to give 4-chloro-7-hydroxy-6-methoxycinnoline as a yellow solid (1.78 g, 94%).

EXAMPLE 11

A suspension of 4-chloro-6-methoxy-7-(2-methoxyethoxy)cinnoline (0.2 g, 0.74 mmol), (prepared as described for the starting material in Example 2), and 2-fluoro-5-hydroxy-4-methylaniline (126 mg 0.89 mmol) in 2-pentanol (2.5 ml) was heated at reflux for 7.5 hours. After cooling, isopropanol was added and the solid was filtered off, washed with isopropanol and ether, and dried under vacuum to give 4-(2-fluoro-5-hydroxy-4-methylanilino)-6-methoxy-7-(2-methoxyethoxy)cinnoline as the hydrochloride salt (yellow solid 196 mg, 64%).

m.p. 283–290° C.; $^1$H NMR Spectrum: (DMSOd$_6$) 2.2 (s, 3H); 3.4 (s, 3H); 3.8 (t, 2H); 4.1 (s, 3H): 6.95 (d, 1H); 7.25 (d, 1H), 7.45 (s, 1H); 8.2 (s, 1H); 8.22 (s, 1H); 9.95 (s, 1H); 11.2 (br s, 1H); MS–ESI: 374 [MH]$^+$;

| Elemental analysis: | Found | C 55.5 | H 5.5 | N 10.0 |
|---|---|---|---|---|
| C$_{19}$H$_{20}$N$_3$O$_4$F 0.1 H$_2$O 1 HCl | Requires | C 55.4 | H 5.2 | N 10.2% |

The starting material, 2-fluoro-5-hydroxy-4-methylaniline was obtained as follows:

Methyl chloroformate (6.8 ml, 88 mmol) was added over 30 minutes to a solution of 4-fluoro-2-methylphenol (10 g, 79 mmol) in 6% aqueous sodium hydroxide solution at 0° C. The mixture was stirred for 2 hours, then extracted with ethyl acetate (100 ml). The ethyl acetate extract was washed with water (100 ml) and dried (MgSO$_4$) and the solvent removed by evaporation to give 4-fluoro-2-methylphenyl methyl carbonate (11.4 g, 78%) as an oil.

$^1$H NMR Spectrum: (DMSOd$_6$) 2.14 (s, 3H), 3.81 (s, 3H); 7.05 (m, 1H); 7.1–7.5 (m, 2H).

A mixture of concentrated nitric acid (6 ml) and concentrated sulphuric acid (6 ml) was added slowly to a solution of 4-fluoro-2-methylphenyl methyl carbonate (11.34 g, 62 mmol) in concentrated sulphuric acid (6 ml) such that the temperature of the reaction mixture was kept below 50° C. The mixture was stirred for 2 hours, then ice/water was added and the precipitated product collected by filtration. The crude product was purified by chromatography on silica eluting with methylene chloride/hexane progressing through increasingly polar mixtures to methanol/methylene chloride (1/19) to give 4-fluoro-2-methyl-5-nitrophenol (2.5 g, 22%) as a solid.

$^1$HNMR Spectrum: (DMSOd$_6$; CD$_3$COOD) 2.31 (s, 3H); 7.38 (d, 1H); 7.58 (d, 1H); MS: 171 [MH]$^+$.

A mixture of 4-fluoro-2-methyl-5-nitrophenol (2.1 g, 13 mmol), iron powder (1 g, 18 mmol) and iron(II)sulphate (1.5 g, 10 mmol) in water (40 ml) was heated at reflux for 4 hours. The reaction mixture was allowed to cool, neutralised with 2M aqueous sodium hydroxide solution and extracted with ethyl acetate (100 ml). The ethyl acetate extract was dried (MgSO$_4$) and the solvent removed by evaporation to give 2-fluoro-5-hydroxy-4-methylaniline (0.8 g, 47%) as a solid.

$^1$H NMR Spectrum: (DMSOd$_6$) 1.94 (s, 3H); 4.67 (s, 2H); 6.22 (d, 1H); 6.65 (d, 1H); 8.68 (s, 1H); MS: 142 [MH]$^+$.

EXAMPLE 12

A solution of 4-chloro-6-methoxy-7-(3-morpholinopropoxy)cinnoline hydrochloride (83 mg, 0.2 mmol) and 4-chloro-2-fluoro-5-hydroxyaniline (42 mg, 0.26 mmol), (prepared as described in EP 061741 A2), in 2-pentanol (5 ml) containing DMF (0.5 ml) was heated at 120° C. for 2.5 hours. The work up procedure was identical to the synthesis of the final product in Example 11 and gave 4-(4-chloro-2-fluoro-5-hydroxyanilino)-6-methoxy-7-(3-morpholinopropoxy)cinnoline as the hydrochloride salt (70 mg 65%).

m.p. 218–225° C.; $^1$H NMR Spectrum: (DMSOd$_6$; CD$_3$COOD) 2.4 (m, 2H); 3.35 (m, 6H); 3.9 (m, 4H); 4.1 (s, 3H); 4.4 (t, 2H); 7.2 (d, 1H); 7.45 (s, 1H); 7.6 (d, 1H); 8.1 (s, 1H); 8.35 (s, 1H); MS–ESI: 463 [MH]+;

| Elemental analysis: | Found | C 46.1 | H 5.2 | N 9.5 |
| --- | --- | --- | --- | --- |
| $C_{22}H_{24}N_4O_4ClF$ 2 $H_2O$ 1.9 HCl | Requires | C 46.5 | H 5.3 | N 9.9% |

The starting material 4-chloro-6-methoxy-7-(3-morpholinopropoxy)cinnoline hydrochloride was obtained by adding 1-chloro-3-morpholinopropane (190 mg, 0.95 mmol), (prepared as described in U.S. Pat. No. 4,004,007), to a suspension of 4-chloro-7-hydroxy-6-methoxycirmoline (0.2 g, 0.95 mmol), (prepared as described for the starting material in Example 10), in DMF (5 ml) containing potassium carbonate (327 mg, 2.3 mmol) and potassium iodide (15 mg, 0.095 mmol). After heating at 80° C. for 2 hours, potassium carbonate (65 mg, 0.47 mmol) and more 1-chloro-3-morpholinopropane (95 mg, 0.47 mmol) were added. After stirring for 4 hours at 80° C., the reaction mixture was cooled and 7M hydrogen chloride in isopropanol (407 µl) was added. The solution was poured onto a Diaion (trade mark of Mitsubishi) HP20SS column, using water/methanol (100/0 to 0/100 as a gradient) to give 4-chloro-6-methoxy-7-(3-morpholinopropoxy)cinnoline as an hydrochloride salt (175 mg, 44%).

EXAMPLE 13

A solution of 4-chloro-6-methoxy-7-(3-pyrrolidinopropoxy)cinnoline hydrochloride (0.1 g, 0.25 mmol) and 4-chloro-2-fluoro-5-hydroxyaniline (57 mg, 0.35 mmol), (prepared as described in EP 061741 A2), in 2-pentanol (5ml) was heated at 120° C. for 2.5 hours. The solid was filtered off, washed with isopropanol and then ether and dried under vacuum to give 4-(4-chloro-2-fluoro-5-hydroxyanilino)-6-methoxy-7-(3-pyrrolidinopropoxy)cinnoline as the hydrochloride salt (yellow solid, 94 mg, 72%).

m.p. 240–245° C.; $^1$H NMR Spectru: (DMSOd$_6$; CF$_3$COOD) 1.9 (m, 2H); 2.1 (m, 2H); 2.3 (m, 2H); 3.1 (m, 2H); 3.35 (m, 2H); 3.65 (m, 2H); 4.1(s, 3H); 4.4 (t, 2H); 7.2 (d, 1H); 7.45 (s, 1H); 7.65 (d, 1H); 8.15 (s, 1H); 8.35 (s, 1H); MS–ESI: 447 [MH]+;

| Elemental analysis: | Found | C 49.9 | H 5.2 | N 10.5 |
| --- | --- | --- | --- | --- |
| $C_{22}H_{24}N_4O_3ClF$ 0.5 $H_2O$ 1.95 HCl | Requires | C 50.1 | H 5.2 | N 10.6% |

The starting material, 4-chloro-6-methoxy-7-(3-pyrrolidinopropoxy)cinnoline hydrochloride was obtained by adding 4-chloro-7-hydroxy-6-methoxycinnoline (0.3 g, 1.4 mmol), (prepared as described for the starting material in Example 10), to a solution of 3-pyrrolidinopropyl chloride (275 mg, 1.5 mmol), (prepared as described in J. Amer. Chem. Soc. 1955, 77, 2272), in DMF (5 ml) containing potassium carbonate (491 mg, 3.5 mmol) and potassium iodide (24 mg, 0.14 mmol). After stirring at 80° C. for 3 hours potassium carbonate (98 mg, 0.7 mmol) and 3-pyrrolidinopropyl chloride (137 mg, 0.7 mmol) were added. After 30 minutes, the mixture was cooled and 7M hydrogen chloride in isopropanol (407 µl) was added. The solution was poured onto a Diaion (trade mark of Mitsubishi) HP20SS TM column eluting with water/methanol (100/0 to 0/100 as a gradient). After evaporation of the solvent, the product was purified by preparative HPLC using a reverse phase C18 column eluting with water/methanol (100/0 to 80/20 as a gradient) to give after concentration, 4-chloro-6-methoxy-7-(3-pyrrolidinopropoxy)cinnoline hydrochloride (265 mg, 48%) as a yellow solid.

EXAMPLE 14

A suspension of 4-chloro-7-methoxycinnoline hydrochloride (196 mg, 0.85 mmol) and 3-hydroxy-4-methylaniline (123 mg, 1 mmol) in 2-pentanol (5 ml) was heated at reflux for 2 hours. After cooling, the solid was filtered off, washed with isopropanol, ether and dried under vacuum to give 4-(3-hydroxy-4-methylanilino)-7-methoxycinnoline as the hydrochloride salt (yellow solid, 215 mg, 80%).

m.p. 270–275° C.; $^1$H NMR Spectrum: (DMSOd$_6$) 2.18 (s, 3H); 4.0 (s, 3H); 6.88 (d, 1H); 6.93 (s, 1H); 7.25 (d, 1H); 7.35 (s, 1H); 7.52 (dd, 1H); 8.4 (s, 1H); 8.75(d, 1H); 9.98 (s, 1H); 11.65 (br s, 1H); MS–ESI: 281 [MH]+;

| Elemental analysis: | Found | C 59.7 | H 5.4 | N 13.0 |
| --- | --- | --- | --- | --- |
| $C_{16}H_{15}N_3O_2$ 0.14 $H_2O$ 1 HCl | Requires | C 60.0 | H 5.1 | N 13.1% |

The starting material 4-chloro-7-methoxycinnoline hydrochloride was obtained by heating a solution of 4-hydroxy-7-methoxycinnoline (352 mg, 2 mmol), (prepared as described in J. Chem. Soc. 1955, 2100), in thionyl chloride (3.5 ml) containing DMF (20 µl) at reflux, for 1 hour. After removing excess thionyl, chloride by evaporation and azeotroping with toluene. The residue was triturated with ether, filtered off and washed with ether to give 4-chloro-7-methoxycinnoline hydrochloride as a yellow solid (450 mg, 97%).

EXAMPLE 15

A solution of 4-chloro-6-methoxy-7-(3-morpholinopropoxy)cinnoline hydrochloro (132 mg, 0.33 mmol), (prepared as described for the starting material in Example 12), and 2-fluoro-5-hydroxy-4-methylaniline (56 mg, 0.39 mmol), (prepared as described for the starting material in Example 11), in 2-pentanol (2.5 ml) containing 7M hydrogen chloride in isopropanol (9 drops) was heated at reflux for 30 minutes. After cooling, the solid was filtered off, washed with isopropanol, ether and dried under vacuum to give 4-(2-fluoro-5-hydroxy-4-methylanilino)-6-metboxy-7-(3-morpholinopropoxy)cinnoline as an hydrochloride salt (yellow solid, 143 mg, 84%).

$^1$H NMR Spectrum: (DMSOd$_6$; CD$_3$COOD) 2.2 (s, 3H); 2.35(m, 2H); 3.3 (m, 6H); 3.9 (br s, 4H); 4.0 (s, 3H); 4.35 (t, 2H); 6.95 (d, 1H); 7.15 (d, 1H); 7.35 (s, 1H); 8.1 (s, 1H); 8.2 (s, 1H); MS–ESI 443 [MH]+;

| Elemental analysis: | Found | C 53.0 | H 6.0 | N 10.2 |
| --- | --- | --- | --- | --- |
| $C_{23}H_{27}N_4O_4F$ 0.5$H_2O$ 2.8HCl 0.2 isopropanol | Requires | C 53.6 | H 6.0 | N 10.6% |

EXAMPLE 16

A solution of 4-chloro-6-methoxy-7-(3-pyrrolidinopropoxy)cinnoline hydrochloride (158 mg, 0.4 mmol),(prepared as described for the starting material in Example 13), and 2-fluoro-5-hydroxy-4-methylaniline (67 mg, 0.48 mmol), (prepared as described for the starting material in Example 11), in 2-pentanol (5 ml) was heated at reflux for 1 hour. After cooling, the solid was filtered off, washed with isopropanol, ether and dried under vacuum to give 4-(2-fluoro-5-hydroxy-4-methylanilino)-methoxy-7 (3-pyrrolidinopropoxy)cinnoline as the hydrochloride salt (yellow solid, 55 mg, 27%).

m.p. 247–253° C.; $^1$H NMR Spectrum: (DMSOd$_6$; CD$_3$COOD) 2.05 (m, 4H); 2.25 (s, 3H); 2.35 (m, 2H); 3.25–3.5 (br s, 6H); 4.05 (s, 3H); 4.4 (br s, 2H); 7.0 (d, 1H); 7.22 (d, 1H); 7.45 (s, 1H); 8.15 (s, 1H); 8.25 (s, 1H); MS–ESI: 427 [MH]$^+$;

| Elemental analysis: | Found | C 53.6 | H 6.1 | N 10.4 |
|---|---|---|---|---|
| C$_{23}$H$_{27}$N$_4$O$_3$F 1H$_2$O 1.95HCl | Requires | C 53.6 | H 6.1 | N 10.9% |

EXAMPLE 17

A suspension of 4-chloro-6-methoxy-7-[(2-methylthiazol-4-yl)methoxy]cinnoline (150 mg, 0.46 mmol) and 2-fluoro-5-hydroxy-4-methylaniline (78 mg, 0.56 mmol), (prepared as described for the starting material in Example 11), in 2-pentanol (3 ml) and a 5M solution of hydrogen chloride in isopropanol (105 μl) was heated at reflux for 90 minutes. The solid obtained was filtered off, washed with isopropanol followed by ether to give 4-(2-fluoro-5-hydroxy-4-methylanilino)-6-methoxy-7-[(2-methylthiazol-4-yl)methoxy]cinnoline hydrochloride as a pale yellow solid (190 mg, 82%).

$^1$H NMR Spectrum: (DMSOd$_6$) 2.19 (s, 3H); 2.69 (s, 3H); 4.03 (s, 3H); 5.39 (s, 2H); 6.98 (d, 1H); 7.24 (d, 1H), 7.66 (s, 1H); 7.76 (s, 1H); 8.16 (d, 1H); 8.27 (s, 1H); 10.0 (br s, 1H); 11.32 (s, 1H); MS–ESI m/z: 427 [MH]$^+$;

| Elemental analysis: | Found | C 50.7 | H 4.4 | N 11.0 |
|---|---|---|---|---|
| C$_{21}$H$_{19}$N$_4$O$_3$SF 0.5H$_2$O 1.65HCl | Requires | C 50.9 | H 4.4 | N 11.3% |

The starting material 4-chloro-6-methoxy-7-[(2-methylthiazol-4-yl)methoxy]cinnoline was obtained by adding potassium carbonate (786 mg, 5.7 mmol) followed by 4-chloromethyl-2-methylthiazole (308 mg, 2 mmol) to a suspension of 4-chloro-7-hydroxy-6-methoxycinnoline (0.4 g, 1.9 mmol), (prepared as described for the starting material in Example 10), in DMF (10 ml). After stirring for 4.5 hours at 60° C., the reaction mixture was diluted with water and acidified to pH4 with 2M hydrochloric acid. After extraction with ethyl acetate, the organic layer was washed with water and then brine, dried (MgSO$_4$) and the solvent evaporated. The residue was purified by flash chromatography using methylene chloride/ethyl acetate (2/8) as eluent to give 4-chloro-6-methoxy-7-[(2-methylthiazol-4-yl)methoxy] cinnoline as a solid (293 mg, 48%).

EXAMPLE 18

A suspension of 4-chloro-6-methoxy-7-[(1-methylimidazol-2-yl)methoxy]cinnoline (109 mg, 0.35 mmol) and 2-fluoro-5-hydroxy-4-methylaniline (70 mg, 0.5mmol), (prepared as described for the starting material in Example 11), in 2-pentanol (3 ml), DMF (0.5 ml) and a 5M solution of hydrogen chloride in isopropanol (74 μl, 0.35 mmol) was heated at reflux for 3 hours. The solution was then cooled to 0° C. and the resulting solid filtered off and washed with ether to give 4-(2-fluoro-5-hydroxy-4-methylanilino)-6-methoxy-7-[(1-methylimidazol-2-yl) methoxy]cinnoline hydrochloride as a yellow solid (124 mg, 73%).

m.p. 215–221° C.; $^1$H NMR Spectrum: (DMSOd$_6$) 2,2 (s, 3H); 3.9 (s, 3H); 4.05 (s, 3H); 5.7 (s, 2H); 6.99 (d, 1H); 7.24 (d, 1H); 7.67 (s, 1H); 7.73 (s, 1H); 7.77 (s, 1H); 8.20 (d, 1H); 8.39 (s, 1H); 9.96 (s, 1H); 11.5 (s, 1H). MS–ESI m/z: 410 [MH]$^+$;

| Elemental analysis: | Found | C 51.3 | H 4.9 | N 13.7 |
|---|---|---|---|---|
| C$_{21}$H$_{20}$N$_5$O$_3$F 0.9H$_2$O 1.8HCl | Requires | C 51.3 | H 4.8 | N 14.3% |

The starting material, 4-chloro-6-methoxy-7-[(1-methylimidazol-2-yl)methoxy]-cinnoline was obtained by adding potassium carbonate (531 mg, 3.8 mmol) followed by 2-chloromethyl-1-methylimidazole (232 mg, 1.4 mmol) to a suspension of 4-chloro-7-hydroxy-6-methoxycinnoline (270 mg, 1.28 mmol), (prepared as described for the starting material in Example 10), in DMF (6 ml). After stirring overnight at 40° C. the mixture was diluted with water and adjusted to pH7. After extraction with ethyl acetate, the organic layer was washed with water and then brine, dried (MgSO$_4$) and the solvent evaporated. The residue was purified by flash chromatography using methylene chloride/methanol (98/2) as eluent to give 4-chloro-6-methoxy-7-[(1-methylimidazol-2-yl)methoxy]cinnoline (11 mg, 29%).

EXAMPLE 19

A solution of 4-chloro-6-methoxy-7-(4-pyridylmethoxy)cinnoline hydrochloride (268 mg, 0.71 mmol), (prepared as described for the starting material in Example 10), and 2-fluoro-5-hydroxy-4-methylaniline, (109 mg, 0.77 mmol), (prepared as described for the starting material in Example 11), in 2-pentanol (6 ml) was heated at reflux for 4 hours. After dilution with isopropanol, the solid was filtered off, washed with isopropanol followed by ether to give 4-(2-fluoro-5-hydroxy-4-methylanilino)-6-methoxy-7-(4-pyridylmethoxy)cinnoline hydrochloride (92 mg, 29%).

m.p. 244–252° C. $^1$H NMR Spectrum: (DMSOd$_6$; CD$_3$COOD) 2.2 (s, 3H); 4.1 (s, 3H); 5.68 (s, 2H); 7.0 (s, 1H); 7.25 (d, 1H); 7.5 (s, 1H); 7.9 (s, 2H); 8.25 (d, 2H); 8.85 (s, 2H); MS–ESI m/z: 407 [MH]$^+$;

| Elemental analysis: | Found | C 58.0 | H 4.8 | N 12.3 |
|---|---|---|---|---|
| C$_{22}$H$_{19}$N$_4$O$_3$F 0.4H$_2$O 1.1HCl | Requires | C 58.2 | H 4.6 | N 12.4% |

EXAMPLE 20

A solution of 4-(5-benzyloxy-2-fluoro-4-methylphenoxy)-6-methoxy-7-(2-methoxyethoxy)cinnoline (242 mg, 0.5 mmol) in a mixture of methanol (9 ml) and DMF (10.5 ml) containing 10% palladium-on-charcoal catalyst (100 mg) was stirred under hydrogen at 5 atmospheres pressure for 9 hours. The catalyst was removed by filtration and the solvent was evaporated. The residue was washed with methanol and ether and dried under vacuum to give 4-(2-fluoro-5-hydroxy-4-methylphenoxy)-6-methoxy-7-(2-methoxyethoxy)cinnoline as a white solid (87 mg, 44%).

m.p. 267–273° C.; $^1$H NMR Spectrum: (DMSOd$_6$; CD$_3$COOD) 2.18 (s, 3H); 3.37 (s, 3H); 3.80 (t, 2H); 4.04 (s, 3H); 4.39 (t, 2H); 6.8 (d, 1H); 7.2 (d, 1H); 7.49 (s, 1H); 7.79 (s, 1H); 8.49 (s, 1H); MS–ESI m/z: 375 [MH]+;

| Elemental analysis: | Found | C 58.9 | H 5.3 | N 7.5 |
|---|---|---|---|---|
| $C_{19}H_{19}N_2O_5F$ 0.7$H_2O$ 0.06DMF | Requires | C 58.9 | H 5.4 | N 7.4% |

The starting material, 4-(5-benzyloxy-2-fluoro-4-methylphenoxy)-6-methoxy-7-(2-methoxyethoxy)cinnoline was obtained by heating a solution of 5-benzyloxy-2-fluoro-4-methylphenol (314 mg, 1.3 mmol) and 4-chloro-6-methoxy-7-(2-methoxyethoxy)cinnoline (280 mg, 1 mmol), (prepared as described for the starting material in Example 2), in pyridine (6 ml), at reflux for 15 hours. After evaporation of the solvent, the residue was partitioned between ethyl acetate and water adjusted to pH7. The organic layer was separated, washed with water and then brine, dried ($MgSO_4$) and the solvent evaporated. The residue was purified by flash chromatography using methylene chloride/ether (4/6 followed by 3/7) as eluent to give 4-(5-benzyloxy-2-fluoro-4-methylphenoxy)-6-methoxy-7-(2-methoxyethoxy)cinnoline as a white solid (247 mg, 53%).
$^1$H NMR Spectrum: (DMSOd$_6$) 2.27 (s, 3H); 3.37 (s, 3H); 3.8 (t, 2H); 4.0 (s, 3H); 4.4 (t, 2H); 5.14 (s, 2H); 7.26 (d, 1H); 7.2–7.5 (m, 6H); 7.5 (s, 1H); 7.81 (s, 1H); 8.44 (s, 1H).

The starting material 5-benzyloxy-2-fluoro-4-methylphenol, was obtained by adding a solution of sodium nitrite (1.68 g, 24 mmol) in water (3.5 ml), dropwise, to a solution of 5-benzyloxy-2-fluoro-4-methylaniline (4.7 g, 20 mmol) in acetic acid (82 ml) and 70% sulphuric acid (3.15 ml) cooled at 10° C. The mixture was stirred vigorously for 20 minutes, then a solution of copper(II)nitrate trihydrate (481 g, 2 mol) in water (790 ml) was added, followed by copper(II)oxide (3 g, 19 mmol). After stirring for 3 hours, the mixture was extracted with ethyl acetate. The organic layer was washed with water and then brine, dried ($MgSO_4$) and the solvent evaporated. The resulting oil was purified by flash chromatography using petroleum ether/ether (85/15) as eluent to give 5-benzyloxy-2-fluoro-4-methylphenol as an orange oil (1.25 g, 27%).

The starting material, 5-benzyloxy-2-fluoro-4-methylaniline, was obtained by adding iron powder (2.88 g, 51 mmol), in portions, to a solution of 5-benzyloxy-2-fluoro-4-methylnitrobenzene (4.8 g, 18 mmol) in acetic acid (33 ml) and water (5.7 ml), at ambient temperature. The mixture was heated and after stirring at 100° C. for 10 minutes, it was cooled and partitioned between ethyl acetate and water. The organic layer was washed with water, aqueous saturated sodium carbonate solution and then brine, dried ($MgSO_4$) and the solvent evaporated. The residue was purified by flash chromatography using petroleum ether/ethyl acetate (8/2) as eluent to give 5-benzyloxy-2-fluoro-4-methylaniline (3.65 g, 87%).

The starting material 5-benzyloxy-2-fluoro-4-methylnitrobenzene was obtained by adding benzyl bromide (3 ml, 25 mmol) to a solution of 2-fluoro-5-hydroxy-4-methylnitrobenzene (3.92 mg, 23 mmol) in DMF (70 ml) containing potassium carbonate (9.5 g, 68 mmol). After stirring for 3 hours at 60° C., the mixture was diluted with water and adjusted to pH2. After extraction with ethyl acetate, the organic layer was washed with water and then brine, dried ($MgSO_4$) and the solvent evaporated. The solid was filtered off, washed with hexane and dried under vacuum to give 5-benzyloxy-2-fluoro-4-methylnitrobenzene (4.83 g, 80%).

The starting material 2-fluoro-5-hydroxy-4-methylnitrobenzene, was obtained by adding 2M aqueous sodium hydroxide solution (13.1 ml), dropwise, to a solution of 2-fluoro-5-methoxycarbonyloxy-4-methylnitrobenzene (6 g, 26 mmol), (prepared as described in European Patent Publication No, 307777), in methanol (70 ml) cooled at 0° C. After stirring for 30 minutes, the mixture was concentrated by evaporation. After dilution with water, the solution was adjusted to pH2 and extracted with ethyl acetate. The organic layer was washed with water and then brine, dried ($MgSO_4$) and the solvent evaporated to give 2-fluoro-5-hydroxy-4-methylnitrobenzene as a yellow solid (4 g, 90%).

EXAMPLE 21

A solution of 4-chloro-6,7-dimethoxycinnoline hydrochloride (261 mg, 1 mmol), (prepared as described for the starting material in Example 1), and 2-fluoro-5-hydroxy-4-methylaniline (170 mg, 1.2 mmol), (prepared as described for the starting material in Example 11), in 2-pentanol (5 ml) was heated at 120° C. for 3 hours. After cooling, the solid was filtered off, washed with isopropanol and ether and dried under vacuum to give 4-(2-fluoro-5-hydroxy-4-methylanilino)-6,7-dimethoxycinnoline as an hydrochloride salt (301 mg, 82%).
m.p. 251–253° C.; $^1$H NMR Spectrum: (DMSOd$_6$; CD$_3$COOD) 2.22 (s, 3H); 4.05 (s, 3H); 4.07 (s, 3H); 6.97 (d, 1H); 7.24 (d, 1H); 7.39 (s, 1H); 8.08 (s, 1H); 8.22 (d, 1H); MS–ESI m/z: 330 [MH]+;

| Elemental analysis: | Found | C 55.2 | H 4.8 | N 11.1 |
|---|---|---|---|---|
| $C_{17}H_{16}N_3O_3F$ 0.1$H_2O$ 1HCl | Requires | C 55.6 | H 4.7 | N 11.4% |

EXAMPLE 22

A solution of 4-chloro-6,7-dimethoxycinnoline hydrochloride (261 mg, 1 mmol), (prepared as described for the starting material in Example 1), and 4-chloro-2-fluoro-5-hydroxyaniline (193 mg, 1.2 mmol), (prepared as described in EP 061741), was treated in a manner similar to that described in Example 21 in order to produce 4-(4-chloro-2-fluoro-5-hydroxyanilino)-6,7-dimethoxycinnoline as an hydrochloride salt (315 mg, 82%).
m.p. 255–256° C.; $^1$H NMR Spectrum: (DMSOd$_6$; CF$_3$COOD) 4.05 (s, 3H); 4.07 (s, 3H); 7.19 (d, 1H); 7.4 (s, 1H); 7.65 (d, 1H); 8.07 (s, 1H); 8.34 (d, 1H); MS–ESI m/z: 350 [MH]+;

| Elemental analysis: | Found | C 49.5 | H 3.8 | N 10.5 |
|---|---|---|---|---|
| $C_{16}H_{13}N_3O_3ClF$ 1HCl | Requires | C 49.8 | H 3.7 | N 10.9% |

EXAMPLE 23

A solution of 4-chloro-6-methoxy-7-[2-(2-methoxyethoxy)ethoxy]cinnoline (130 mg, 0.41 mmol) and 2-fluoro-5-hydroxy-4-methylaniline (70 mg, 0.5 mmol), (prepared as described for the starting material in Example 11), in 2-pentanol (3 ml) containing 5M hydrogen chloride in isopropanol (2drops) was heated at reflux for 45 minutes. After cooling the solid was filtered off, washed with isopropanol followed by ether to give 4-(2-fluoro-5-hydroxy-4-methylanilino)-6-methoxy-7-[2-(2-methoxyethoxy)ethoxy]cinnoline as an hydrochloride salt (159 mg, 88%).

m.p. 250–256° C.; $^1$H NMR Spectrum: (DMSOd$_6$) 2.21 (s, 3H); 3.27 (s, 3H); 3.51 (dd, 2H); 3.66 (dd, 2H); 3.90 (t, 2H); 4.06 (s, 3H); 4.37 (t, 2H); 6.98 (d, 1H); 7.25 (d, 1H); 7.46 (s, 1H); 8.18 (d, 1H); 8.23 (s, 1H); 9.94 (s, 1H); 11.2 (s, 1H); MS–ESI m/z: 418 [MH]$^+$;

| Elemental analysis: | Found | C 55.2 | H 5.7 | N 8.8 |
|---|---|---|---|---|
| C$_{21}$H$_{24}$N$_3$O$_5$F 0.2H$_2$O 1HCl | Requires | C 55.1 | H 5.6 | N 9.2% |

The starting compound 4-chloro-6-methoxy-7-[2-(2-methoxyethoxy)ethoxy]-cinnoline was obtained by adding triphenylphosphine (995 mg, 3.8 mmol), followed by diethyleneglycol (271 μl, 2.2 mmol) and diethyl azodicarboxylate (598 μl, 3.8 mmol), dropwise, to a suspension of 4-chloro-7-hydroxy-6-methoxycinnoline (0.4 g, 1.9 mmol), (prepared as described for the starting material in Example 10), in methylene chloride (12 ml) under nitrogen and cooled to 10° C. After stirring for 1 hour, the solvent was evaporated and the residue purified by flash chromatography using methylene chloride/ethyl acetate (5/5 followed by 4/6) as eluent to give 4-chloro-6-methoxy-7-[2-(2-methoxyethoxy)ethoxy] cinnoline (366 mg, 91%).

EXAMPLE 24

A solution of 4,6-dichlorocinnoline (200 mg, 1 mmol) and 2-fluoro-5-hydroxy-4-methylaniline (169 mg, 1.2 mmol), (prepared as described for the starting material in Example 11), in 2-pentanol (4 ml) containing 7M isopropanolic hydrogen chloride (2 drops) was heated at reflux for 45 minutes. After cooling the solid was filtered off, washed with isopropanol followed by ether to give 6-chloro-4-(2-fluoro-5-hydroxy-4-methylanilino)cinnoline hydrochloride (326 mg, 95%).

$^1$H NMR Spectrum: (DMSOd$_6$) 2.20 (s, 3H); 6.98 (d, 1H); 7.26 (d, 1H); 8.18 (s, 2H); 8.35 (d, 1H); 9.1 (s, 1H); 9.98 (br s, 1H); MS–ESI: 304 [MH]$^+$;

| Elemental Analysis: | Found | C 53.4 | H 4.0 | N 11.9 |
|---|---|---|---|---|
| C$_{15}$H$_{11}$N$_3$OFCl 0.95HCl 0.1H$_2$O | Requires | C 53.0 | H 3.6 | N 12.4% |

The starting material was prepared as follows:

A solution of 4-hydroxy-6-chlorocinnoline (1 g, 5.5 mmol), (J. Chem. Soc. 1961, 1828), in thionyl chloride (10 ml) and DMF (0.1 ml) was heated at reflux for 20 minutes. Toluene was added and the volatiles were removed by evaporation. The solid was partitioned between ethyl acetate and water and the aqueous layer adjusted to pH7 with sodium hydrogen carbonate. The organic layer was washed with water and brine, dried (MgSO$_4$) and the volatiles removed by evaporation. The residue was purified by column chromatography eluting with methylene chloride/ether (95/5) to give 4,6-dichlorocinnoline (804 mg, 73%).

m.p. 111–113° C.; $^1$H NMR Spectrum: (CDCl$_3$) 7.85 (dd, 1H); 8.18 (d, 1H); 8.52 (d, 1H); 9.36 (s, 1H); MS–EI: 199 [M.]$^+$;

| Elemental Analysis: | Found | C 48.5 | H 2.1 | N 14.0 |
|---|---|---|---|---|
| C$_8$H$_4$N$_2$Cl$_2$ | Requires | C 48.3 | H 2.0 | N 14.1% |

EXAMPLE 25

A solution of 4-chloro-6-methoxy-7-(3-morpholinopropoxy)cinnoline hydrochloride (150 mg, 0.36 mmol), (prepared as described for the starting material in Example 12), 4-chloro-2-fluoroaniline (77 mg, 0.53 mmol) in 2-pentanol (4 ml) and 5M isopropanolic hydrogen chloride (1 ml) was heated at 120° C. for 1 hour. The mixture was allowed to cool and isopropanol was added. The resulting precipitate was collected by filtration, washed with ether and dried under vacuum to give 4-(4-chloro-2-fluoroanilino)-6-methoxy-7-(3-morpholinopropoxy)cinnoline hydrochloride (185 mg, 98%).

$^1$H NMR Spectrum: (DMSOd$_6$) 2.3–2.4 (m, 2H); 3.1–3.2 (m, 2H); 3.3–3.4 (m, 2H); 3.5–3.6 (m, 2H); 3.8–3.95 (m, 2H); 3.95–4.1 (m, 2H); 4.08 (s, 3H); 4.38 (t, 2H); 7.55 (dd, 1H); 7.57 (s, 1H); 7.71 (t, 1H); 7.80 (dd, 1H); 8.31 (d, 1H); 8.4 (s, 1H); MS–ESI: 447 [MH]$^+$;

| Elemental Analysis: | Found | C 50.0 | H 5.2 | N 10.2 |
|---|---|---|---|---|
| C$_{22}$H$_{24}$N$_4$O$_2$FCl 1.95HCl 0.5H$_2$O | Requires | C 50.1 | H 5.1 | N 10.6% |

EXAMPLE 26

A solution of 4-chloro-6-methoxy-7-(3-pyrrolidinopropoxy)cinnoline hydrochloride (130 mg, 0.32 mmol), (prepared as described for the starting material in Example 13), and 4-chloro-2-fluoroaniline (70 mg, 0.48 mmol), in 2-pentanol (4 ml) and 5M isopropanolic hydrogen chloride (1 ml) was heated at 120° C. for 2.5 hours. The solid was filtered off, washed with isopropanol and then ether and dried under vacuum to give 4-(4-chloro-2-fluoroanilino)-6-methoxy-7-(3-pyrrolidinopropoxy)cinnoline hydrochloride (110 mg, 66%).

$^1$H NMR Spectrum: (DMSOd6; CD$_3$COOD) 1.9–2.1 (m, 4H); 2.25–2.35 (m, 2H); 3.0–3.3 (br m, 2H); 3.36 (t, 2H); 3.4–3.7 (m, 2H); 4.06 (s, 3H); 4.38 (t, 2H); 7.46 (s, 1H); 7.55 (d, 1H); 7.72 (t, 1H); 7.75 (dd, 1H); 8.21 (s, 1H); 8.33 (s, 1H); MS–ESI: 431 [MH]$^+$;

| Elemental Analysis: | Found | C 51.2 | H 5.4 | N 10.3 |
|---|---|---|---|---|
| C$_{22}$H$_{24}$N$_4$O$_2$FCl 1.9HCl 1.1H$_2$O | Requires | C 50.8 | H 5.4 | N 10.8% |

EXAMPLE 27

A solution of 4-chloro-7-(2-methoxyethoxy)cinnoline (156 mg, 0.65 mmol) and 2-fluoro-5-hydroxy-4-methylaniline (111 mg, 0.78 mmol), (prepared as described for the starting material in Example 11), in 2-pentanol (8 ml) and 5M isopropanolic hydrogen chloride (1 ml) was heated at 120° C. for 2.5 hours. The solid was filtered off washed with isopropanol and then ether and dried under vacuum to give 4-(2-fluoro-5-hydroxy-4-methylanilino)-7-(2-methoxyethoxy)cinnoline hydrochloride (207 mg, 84%).

$^1$H NMR Spectrum: (DMSOd$_6$) 2.19 (s, 3H); 3.4 (s, 3H); 3.8 (t, 2H); 4.4 (t, 2H); 6.96 (d, 1H); 7.25 (d, 1H); 7.38 (s, 1H); 7.61 (d, 1H); 8.21 (s, 1H); 8.71 (d, 1H); 9.94 (s, 1H); MS–ESI: 344 [MH]$^+$;

| Elemental Analysis: | Found | C 57.1 | H 5.4 | N 11.3 |
|---|---|---|---|---|
| C$_{18}$H$_{18}$N$_3$O$_3$F 0.15H$_2$O 0.95HCl | Requires | C 56.8 | H 5.1 | N 11.0% |

The starting material was prepared as follows:

Diethyl azodicarboxylate (349 μl 2.2 mmol) was added dropwise to a suspension of 4-chloro-7-hydroxycinnnoline (200 mg, 1.1 mmol), triphenylphosphine (580 mg, 2.2 mmol) and 2-methoxyethanol (105 μl, 1.3 mmol) in methylene chloride (6 ml) cooled at 10° C. The mixture was stirred for 30 minutes and further triphenylphosphine (145 mg), 2-methoxyethanol (20 μl) and diethyl azodicarboxylate (88 μl) were added. The mixture was then allowed to warm to ambient temperature and stirred for 30 minutes. The volatiles were removed by evaporation and the residue was purified by column chromatography eluting with ethyl acetate/petroleum ether (7/3) and followed by column chromatography eluting with cyclohexane/ethyl acetate 35/65 to give 4-chloro-7-(2-methoxyethoxy)cinnoline (158 mg, 60%).

$^1$H NMR Spectrum: (CDCl$_3$) 3.5 (s, 3H); 3.88 (m, 2H); 4.36 (m, 2H); 7.58 (dd, 1H); 7.77 (d, 1H); 8.08 (d, 1H); 9.2 (s, 1H).

Aluminium trichloride (2.6 g, 19 mmol) was added in portions to a suspension of 4-chloro-7-methoxycinnoline (0.9 g, 3.8 mmol), (J. Chem. Soc. 1955, 2100), in benzene (15 ml) and the mixture was heated at reflux for 1 hour. The solvent was removed by evaporation and the residue was partitioned between ice/water and ethyl acetate. Aqueous saturated sodium chloride solution was added and the organic layer was separated. The organic layer was washed with brine, dried (MgSO$_4$) and the solvent removed by evaporation. The residue was triturated with ether, collected, filtered and dried under vacuum to give 4-chloro-7-hydroxycinnoline (368 mg, 53%).

$^1$H NMR Spectrum: (DMSOd$_6$) 7.6 (dd, 1H); 7.66 (d, 1H); 8.11 (d, 1H); 9.35 (s, 1H).

EXAMPLE 28

The following illustrate representative pharmaceutical dosage forms containing the compound of formula I, or a pharmaceutically acceptable salt thereof (hereafter compound X), for therapeutic or prophylactic use in humans:

| (a) Tablet I | mg/tablet |
|---|---|
| Compound X | 100 |
| Lactose Ph. Eur. | 182.75 |
| Croscarmellose sodium | 12.0 |
| Maize starch paste (5% w/v paste) | 2.25 |
| Magnesium stearate | 3.0 |
| (b) Tablet II | mg/tablet |
| Compound X | 50 |
| Lactose Ph. Eur. | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | mg/tablet |
| Compound X | 1.0 |
| Lactose Ph. Eur. | 93.25 |
| Croscarmellose sodium | 4.0 |
| Maize starch paste (5% w/v paste) | 0.75 |
| Magnesium stearate | 1.0 |
| (d) Capsule | mg/capsule |
| Compound X | 10 |
| Lactose Ph. Eur. | 488.5 |
| Magnesium stearate | 1.5 |
| (e) Injection I | (50 mg/ml) |
| Compound X | 5.0% v/v |
| 1 N Sodium hydroxide solution | 15.0% w/v |
| 0.1 N Hydrochloric acid (to adjust pH to 7.6) | |
| Polyethylene glycol 400 | 4.5% w/v |
| Water for injection to 100% | |
| (f) Injection II | 10 mg/ml) |
| Compound X | 1.0% w/v |
| Sodium phosphate BP | 3.6% w/v |
| 0.1 N Sodium hydroxide solution | 15.0% v/v |
| Water for injection to 100% | |
| (g) Injection III | (1 mg/ml. buffered to pH 6) |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

Note
The above formulations may be obtained by conventional procedures well known in the pharmaceutical art. The tablets (a)–(c) may be enteric coated by conventional means for example to provide a coating of cellulose acetate phthalate.

What is claimed is:
1. A cinnoline derivative of the formula I:

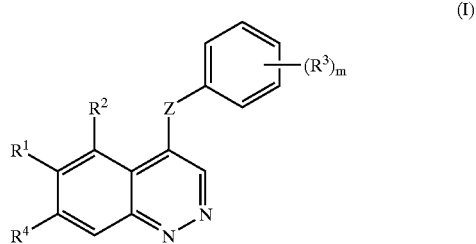

(I)

wherein:
Z represents —O—, —NH—, —S— or —CH$_2$—;
m is an integer from 1 to 5;
R$^1$ represents hydrogen, hydroxy, halogeno, nitro, cyano, trifluoromethyl, C$_{1-3}$alkyl, C$_{1-3}$alkoxy, C$_{1-3}$alkylthio or NR$^6$R$^7$, wherein R$^6$ and R$^7$, which may be the same or different, each represents hydrogen or C$_{1-3}$alkyl;
R$^2$ represents hydrogen, hydroxy, fluoro, chloro, methoxy, amino or nitro;
R$^3$ represents hydroxy, halogeno, C$_{1-3}$alkyl, C$_{1-3}$alkoxy, C$_{1-3}$alkanoyloxy, trifluoromethyl, cyano, amino or nitro;
R$^4$ is a group R$^5$—X$^1$, wherein:
X$^1$ represents —O—; and
R$^5$ is selected from one of the following four groups:
1) C$_{2-4}$alkylX$^{3a}$R$^{14a}$ (wherein X$^{3a}$ represents —O— and R$^{14a}$ represents C$_{1-3}$alkyl);
2) C$_{2-3}$alkylX$^{4a}$C$_{2-3}$alkylX$^{5a}$R$^{15a}$ (wherein X$^{4a}$ and X$^{5a}$ are each —O— and R$^{15a}$ represents hydrogen or C$_{1-3}$alkyl);
3) C$_{1-5}$alkylR$^{25a}$ (wherein R$^{25a}$ is a 5 or 6 membered saturated heterocyclic group with one or two heteroatoms, selected independently from O, S and N, which heterocyclic group is linked to C$_{1-5}$alkyl through a carbon atom and which heterocyclic group may bear one or two substituents selected from halogeno, C$_{1-4}$alkyl, C$_{1-4}$hydroxyalkyl and C$_{1-4}$alkoxy) or $C_{2-5}$alkyl$R^{26a}$ (wherein $R^{26a}$ is a 5 or 6 membered saturated heterocyclic group with one or two heteroatoms of which one is N and the other is selected independently from O, S and N, which heterocyclic group is linked to $C_{2-5}$alkyl through a nitrogen atom and which heterocyclic group may bear one or two substituents selected from halogeno, $C_{1-4}$alkyl, $C_{1-4}$hydroxyalkyl and $C_{1-4}$alkoxy); wherein the 5 or 6 membered heterocyclic ring is selected from pyrrolidinyl, piperazinyl, piperidinyl, 1,3-dioxolan-2-yl, 1,3-dioxan-2-yl, 1,3-dithiolan-2-yl, 1,3-dithian-2-yl, morpholino and thiomorpholino; and 4) $(CH_2)_{na}R^{20a}$ (wherein na is an integer from 0 to 4 and $R^{20a}$ is a phenyl group or a 5 or 6 membered aromatic heterocyclic group with 1 to 3 heteroatoms selected from O, N and S, which phenyl or aromatic heterocyclic group may carry up to 5 substituents selected from halogeno, $C_{1-4}$alkyl, $C_{1-4}$alkoxy, $C_{1-4}$hydroxyalkyl, $C_{1-4}$hydroxyalkoxy, carboxy, cyano, $CONR^{21a}R^{22a}$ and $NR^{23a}COR^{24a}$ (wherein $R^{21a}$, $R^{22a}$, $R^{23a}$ and $R^{24a}$, which may be the same or different, each represents hydrogen or $C_{1-4}$alkyl); and wherein the 5 or 6 membered aromatic heterocyclic group is selected from pyridyl, imidazolyl, thiazolyl, thienyl, pyridazinyl and triazolyl;

with the proviso that:
where m is 1, $R^3$ is meta-hydroxy;
the phenyl group bearing $(R^3)_m$ is not 3,4-dimethylphenyl; and
when the phenyl group bearing $(R^3)_m$ is 2,5-dichlorophenyl, 3,5-dichlorophenyl, 2,3-dichlorophenyl, 2,4-dichlorophenyl, 3,4-dichlorophenyl, 2,6-dichlorophenyl, 2,6-dimethylphenyl, 2-bromo-4-chlorophenyl, 4-bromo-2-chlorophenyl, 2-bromo-4-methylphenyl, 2-chloro-4-methylphenyl, 2-chloro-4-hydroxyphenyl, 3-chloro-4-hydroxyphenyl, 3,5-dichloro-4-hydroxyphenyl, 2,5-dichloro-4-hydroxyphenyl or 5-chloro-2-methylphenyl, Z is —NH—;
and salts thereof.

2. A cinnoline derivative as claimed in claim 1 wherein $R^2$ is hydrogen.

3. A cinnoline derivative as claimed in claim 1 wherein Z is —NH—.

4. A cinnoline derivative as claimed in claim 1 wherein $R^1$ is methoxy.

5. A cinnoline derivative as claimed in claim 1 wherein the phenyl group bearing $(R^3)_m$ is a 2-fluoro-5-hydroxy-4-methylphenyl, 4-chloro-2-fluoro-5-hydroxyphenyl, 4-chloro-3-hydroxyphenyl, 4-bromo-3-hydroxyphenyl, 3-hydroxy-4-methylphenyl, or a 4-bromo-2-fluoro-5-hydroxyphenyl group.

6. A cinnoline derivative as claimed in claim 1 wherein $R^5$ is selected from one of the following four groups:
1) $C_{2-4}$alkyl$X^{3a}R^{14a}$ (wherein $X^{3a}$ represents —O— and $R^{14a}$ represents $C_{1-3}$alkyl);
2) $C_{2-3}$alkyl$X^{4a}C_{2-3}$alkyl$X^{5a}R^{15a}$ (wherein $X^{4a}$ and $X^{5a}$ are each —O— and $R^{15a}$ represents hydrogen or $C_{1-3}$alkyl);
3) $C_{1-4}$alkyl$R^{25a}$ (wherein $R^{25a}$ is selected from pyrrolidinyl, piperazinyl, piperidyl, 1,3-dioxolan-2-yl, 1,3-dioxan-2-yl, 1,3-dithiolan-2-yl and 1,3-dithian-2-yl, such that $R^{25a}$ is linked to $C_{1-4}$alkyl through a carbon atom) or $C_{2-4}$alkyl$R^{26a}$ (wherein $R^{26a}$ is selected from morpholino, pyrrolidin-1-yl, piperazin-1-yl and piperidino); and 4) $(CH_2)_{na}R^{20a}$ (wherein na is an integer from 1 to 3 and $R^{20a}$ is a 5 or 6 membered aromatic heterocyclic group with 1 to 2 heteroatoms selected from O, N and S, which aromatic heterocyclic group may be substituted as hereinbefore defined, wherein the 5 or 6 membered aromatic heterocyclic group is selected from pyridyl, imidazolyl, thiazolyl, thienyl, pyridazinyl and triazolyl.

7. A cinnoline derivative as claimed in claim 1 wherein $R^5$ is selected from one of the following four groups:
1) $C_{2-3}$alkyl$X^{3a}R^{14a}$ (wherein $X^{3a}$ represents —O— and $R^{14a}$ represents $C_{1-2}$alkyl);
2) $C_{2-3}$alkyl$X^{4a}C_{2-3}$alkyl$X^{5a}R^{15a}$ (wherein $X^{4a}$ and $X^{5a}$ are each —O— and $R^{15a}$ represents hydrogen or $C_{1-2}$alkyl);
3) $C_{1-2}$alkyl$R^{25a}$ (wherein $R^{25a}$ is selected from pyrrolidinyl, piperazinyl, piperidyl, 1,3-dioxolan-2-yl, 1,3-dioxan-2-yl, 1,3-dithiolan-2-yl and 1,3-dithian-2-yl, such that $R^{25a}$ is linked to $C_{1-2}$alkyl through a carbon atom) or $C_{2-3}$alkyl$R^{26a}$ (wherein $R^{26a}$ is selected from morpholino, piperidino, piperazin-1-yl and pyrrolidin-1-yl); and
4) $(CH_2)_{na}R^{20a}$ (wherein na is an integer from 1 to 3 and $R^{20a}$ is selected from pynidyl, imidazolyl, thiazolyl, thienyl and pyridazinyl, and $R^{20a}$ may be substituted with one substituent selected from halogeno, $C_{1-2}$alkyl, $C_{1-2}$alkoxy, $C_{1-2}$hydroxyalkyl, $C_{1-2}$hydroxyalkoxy, carboxy, cyano, $CONR^{21a}R^{22a}$ and $NR^{23a}COR^{24a}$ (wherein $R^{21a}$, $R^{22a}$, $R^{23a}$ and $R^{24a}$, which may be the same or different, each represents hydrogen or $C_{1-2}$alkyl).

8. A cinnoline derivative as claimed in claim 1 wherein $R^4$ is a group $R^5$—$X^1$, wherein:
$X^1$ is —O—; and
$R^5$ is 2-methoxyethyl, 3-methoxypropyl, 2-morpholinoethyl, 3-morpholinopropyl, 2-piperidinoethyl, 3-piperidinopropyl, 2-(piperazin-1-yl)ethyl, 3-(piperazin-1-yl)propyl, 2-(pyrrolidin-1-yl)ethyl, 3-(pyrrolidin-1-yl)propyl, 2-(1,3-dioxolan-2-yl)methyl, 3-(1,3-dioxolan-2-yl)ethyl, 2-(2-methoxyethylamino)ethyl, 2-methylthiazol-4-ylmethyl, 1-methylimidazol-2-ylmethyl, 4-pyridylmethyl, 2-(4-pyridyl)ethyl or 3-(4-pyridyl)propyl.

9. A compound of the formula Ib:

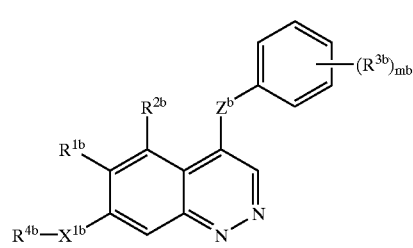

(Ib)

wherein
$R^{1b}$ is hydrogen, $C_{1-3}$alkoxy, or halogeno;
$R^{2b}$ is hydrogen;
$X^{1b}$ is —O—;
$R^{4b}$ is $C_{1-3}$alkyl, 2-($C_{1-3}$alkoxy)ethyl, benzyl, 4-pyridyl ($C_{1-3}$alkyl), morpholino($C_{1-3}$alkyl), pyrrolidino($C_{1-3}$alkyl), 2-methylthiazol-4-yl($C_{1-3}$alkyl), 1-methylimidazol-2-yl($C_{1-3}$alkyl) and 2-(($C_{1-3}$alkoxy)($C_{1-3}$alkoxy))ethyl;
$Z^b$ is —NH— or —O—;
mb is 2 or 3; and
the phenyl group bearing $(R^{3b})_{mb}$ is selected from:
3-hydroxy-4-methylphenyl, 4-chloro-2-fluorophenyl, 4-bromo-2-fluorophenyl, 4-chloro-2-fluoro-5-hydroxyphenyl, 5-acetoxy-4-chloro-2-fluorophenyl, 2-fluoro-5-bydroxy-4-methylphenyl and 4-bromo-2-fluoro-5-hydroxyphenyl;

or a salt thereof.

10. A cinnoline derivative as claimed in claim 1 selected from:

4-(4-chloro-2-fluoro-5-hydroxyanilino)-6-methoxy-7-(2-methoxyethoxy)cinnoline, 4-(4-bromo-2-fluoro-5-hydroxyanilino)-6-methoxy-7-(2-methoxyethoxy)cinnoline, 4-(2-fluoro-5-hydroxy-4-methylanilino)-6-methoxy-7-(2-methoxyethoxy)cinnoline, 4-(2-fluoro-5-hydroxy-4-methylanilino)-6-methoxy-7-(3-morpholinopropoxy)cinnoline, 4-(2-fluoro-5-hydroxy-4-methylanilino)-6-methoxy-7-[(2-methylthiazol-4-yl) methoxy]cinnoline, 4-(2-fluoro-5-hydroxy-4-methylanilino)-6-methoxy-7-(3-pyrrolidinopropoxy)cinnoline, and salts thereof.

11. A cinnoline derivative as claimed in any one of the claims 1–10 in the form of a pharmaceutically acceptable salt.

12. A process for the preparation of a cinnoline derivative of formula I or salt thereof, as defined in claim 1, which comprises:

(a) the reaction of a compound of the formula III:

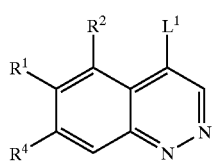

(III)

(wherein $R^1$, $R^2$ and $R^4$ are as defined in claim 1 and $L^1$ is a displaceable moiety), with a compound of the formula IV:

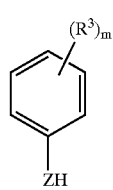

(IV)

(wherein Z, $R^3$ and m are as defined in claim 1) whereby to obtain compounds of the formula I and salts thereof;

(b) for the preparation of compounds of formula I and salts thereof in which the group of formula IIa:

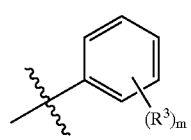

(IIa)

(wherein $R^3$ and m are as defined in claim 1) represents a phenyl group carrying one or more hydroxy groups, the deprotection of a compound of formula V:

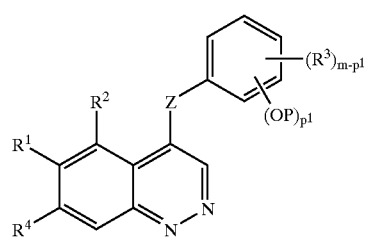

(V)

wherein $R^1$, $R^2$, $R^3$, $R^4$, Z and m are as defined in claim 1, P represents a phenolic hydroxy protecting group and $p^1$ is an integer from 1 to 5 equal to the number of protected hydroxy groups and such that $m-p^1$ is equal to the number of $R^3$ substituents which are not protected hydroxy;

(c) for the preparation of those compounds of formula I and salts thereof wherein the substituent $R^4$ represents $R^5$—$X^1$ in which $R^5$ is as defined in claim 1 and $X^1$ is —O—, the reaction of a compound of the formula VI:

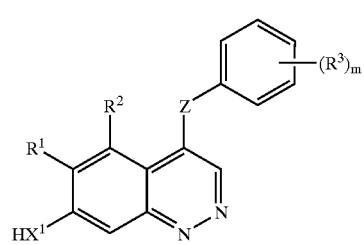

(VI)

wherein $X^1$ is as defined herein, and $R^1$, $R^2$, Z, $R^3$ and m are as defined in claim 1 with a compound of formula VII:

$R^5$—$L^1$ (VII)

wherein $R^5$ is as defined in claim 1 and $L^1$ is a displaceable moiety;

(d) for the preparation of those compounds of the formula I and salts thereof wherein the substituent $R^4$ represents $R^5$—$X^1$ the reaction of a compound of the formula VIII:

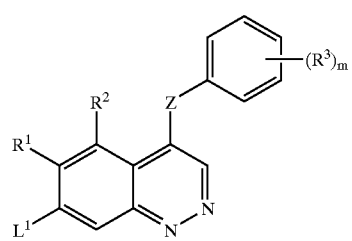

(VIII)

with a compound of the formula IX:

$R^5$—$X^1$—H (IX)

(wherein $R^1$, $R^2$, $R^5$, Z, $X^1$, $R^3$ and m are as defined in claim 1, and $L^1$ is a displaceable moiety;

(e) for the preparation of those compounds of the formula I and salts thereof wherein $R^4$ represents $R^5$—$X^1$ in which $X^1$ is as defined in claim 1 and $R^5$ is $C_{2-3}$alkyl$R^{64}$, wherein $R^{64}$ is selected from one of the following three groups:

1) $X^{10}C_{1-3}$alkyl, wherein $X^{10}$ represents —O—;
2) $X^{11}C_{2-3}$alkyl$X^{5a}R^{15a}$, wherein $X^{11}$ is —O— and $X^{5a}$ and $R^{15a}$ are as defined in claim 1; and
3) an aromatic heterocyclic group selected from imidazolyl, which aromatic heterocyclic group is linked to the $C_{2-3}$alkyl moiety via a nitrogen atom of the heterocyclic ring, and which aromatic heterocyclic group may carry up to 4 substituents selected from halogeno, $C_{1-4}$alkyl, $C_{1-4}$alkoxy, $C_{1-4}$hydroxyalkyl; or a 5 or 6 membered saturated heterocyclic group with one or two heteroatoms, of which one is nitrogen and the other one may be selected independently from O, S and N, which saturated heterocyclic group is linked to the $C_{2-3}$alkyl moiety via a nitrogen atom of the heterocyclic group, and which saturated heterocyclic group may bear one or two substituents selected from halogeno, $C_{1-4}$alkyl, $C_{1-4}$hydroxyalkyl and $C_{1-4}$alkoxy, wherein the 5 or 6 membered heterocyclic ring is selected from pyrrolidinyl, piperazinyl, piperidinyl, 1,3-dioxolan-2-yl, 1,3-dioxan-2-yl, 1,3-dithiolan-2-yl, 1,3-dithian-2-yl, morpholino and thiomorpholino;

by reacting a compound of the formula X:

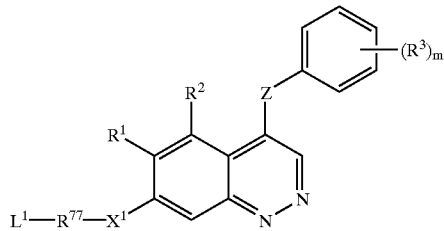

(X)

(wherein $X^1$, $R^1$, $R^2$, Z, $R^3$ and m are as defined in claim 1, $L^1$ is a displaceable moiety and $R^{77}$ is $C_{2-3}$alkyl) with a compound of the formula XI:

$R^{64}$—H (XI)

(wherein $R^{64}$ is as defined herein);

and when a salt of a cinnoline derivative of formula I is required, reaction of the compound obtained from any of the above routes with an acid or base whereby the desired salt is obtained.

13. A pharmaceutical composition which comprises as active ingredient a cinnoline derivative of formula I or a pharmaceutically acceptable salt thereof as claimed in any one of claims 1–10 in association with a pharmaceutically acceptable excipient or carrier.

\* \* \* \* \*